(12) United States Patent
Das et al.

(10) Patent No.: US 8,294,974 B2
(45) Date of Patent: Oct. 23, 2012

(54) ELECTROCHROMIC MATERIAL AND ELECTROCHROMIC DEVICE INCLUDING THE SAME

(75) Inventors: Rupasree Ragini Das, Suwon-si (KR); Ji-Min Lee, Hwaseong-si (KR); Chang-Ho Noh, Suwon-si (KR); Seog-Jin Jeon, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 54 days.

(21) Appl. No.: 13/040,065

(22) Filed: Mar. 3, 2011

(65) Prior Publication Data

US 2011/0235150 A1 Sep. 29, 2011

(30) Foreign Application Priority Data

Mar. 26, 2010 (KR) .................. 10-2010-0027343

(51) Int. Cl.
*G02F 1/15* (2006.01)
(52) U.S. Cl. ......... 359/265; 359/273; 359/274; 252/586
(58) Field of Classification Search .......... 359/265–275; 252/586
See application file for complete search history.

(56) References Cited

U.S. PATENT DOCUMENTS

| 7,106,489 B2* | 9/2006 | Berneth et al. ............. 359/273 |
| 7,242,542 B2* | 7/2007 | Shimizu et al. ............. 252/586 |
| 7,570,412 B2* | 8/2009 | Shibuya et al. ............. 359/265 |
| 2005/0179012 A1 | 8/2005 | Kwon et al. |
| 2006/0110638 A1 | 5/2006 | Corr et al. |

FOREIGN PATENT DOCUMENTS

| JP | 2007031708 A | 2/2007 |
| JP | 2009048142 A | 3/2009 |
| WO | 2004067673 A1 | 8/2004 |

\* cited by examiner

*Primary Examiner* — Evelyn A. Lester
(74) *Attorney, Agent, or Firm* — Cantor Colburn LLP

(57) ABSTRACT

Disclosed is an electrochromic material including a compound represented by Chemical Formula 1 and an electrochromic device including the electrochromic material.

Chemical Formula 1

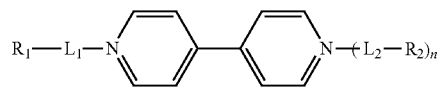

In Chemical Formula 1, $R_1$, $R_2$, $L_1$, and $L_2$ are as defined in the detailed description.

12 Claims, 51 Drawing Sheets
(32 of 51 Drawing Sheet(s) Filed in Color)

ELECTROCHROMIC MATERIAL AND ELECTROCHROMIC DEVICE INCLUDING THE SAME

CROSS-REFERENCE TO RELATED APPLICATION

This application claims priority to Korean Patent Application No. 10-2010-0027343 filed on Mar. 26, 2010, and all the benefits accruing therefrom under 35 U.S.C. 119, the contents of which are herein in the entirety incorporated by reference.

BACKGROUND

1. Field

This disclosure relates to an electrochromic material and an electrochromic device including the same.

2. Description of the Related Art

Electrochromism refers to a phenomenon in which a color reversibly changes with the direction of an electric field when a voltage is applied. A material having such property, that is, a material whose optical characteristic may reversibly change through an electrochemical redox reaction, is called an electrochromic material. An electrochromic material may not show color until an electric field is applied, or conversely, may show color when no electric field is applied and lose the color when an electric field is applied.

Electrochromic materials have been used to manufacture electrochromic devices that changes light transmission characteristics versus the voltage applied.

Electrochromic devices based on variable light transmission characteristics controlled by applied electric fields include, for example, smart windows. Electrochromic materials have also been applied to display devices such as electronic paper, due to the excellent portability and light weight afforded to devices which operate by electrochromism.

SUMMARY

One aspect of the present invention provides a novel electrochromic material.

Another aspect of the present invention provides an electrochromic device including the electrochromic material.

According to one embodiment, an electrochromic material including at least one compound represented by the following Chemical Formula 1 is provided.

Chemical Formula 1

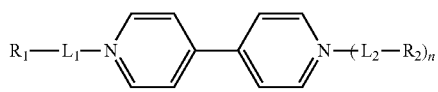

In Chemical Formula 1, $R_1$ is a substituted or unsubstituted imidazole, a substituted or unsubstituted oxazole, a substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group, or a combination comprising at least one of the foregoing groups, $R_2$ is a substituted or unsubstituted imidazole, a substituted or unsubstituted oxazole, a substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group, a phosphonium acid group; a carboxylic acid group; a sulfonic acid group; a hydroxy group; a substituted or unsubstituted C1 to C30 alkyl group, a substituted or unsubstituted C3 to C30 cycloalkyl group, a substituted or unsubstituted C6 to C30 aryl group, or a substituted or unsubstituted C2 to C30 heteroaryl group substituted with a phosphonium acid group, a carboxylic acid group, a sulfonic acid group, or a hydroxy group; or a combination comprising at least one of the foregoing groups, $L_1$ and $L_2$ are each independently a single bond, a substituted or unsubstituted C1 to C30 alkylene group, a substituted or unsubstituted C3 to C30 cycloalkylene group, a substituted or unsubstituted C2 to C30 heterocycloalkylene group, a substituted or unsubstituted C6 to C30 arylene group, a substituted or unsubstituted C7 to C30 aralkylene group, a substituted or unsubstituted C2 to C30 heteroarylene group, a substituted or unsubstituted C3 to C30 heteroaralkylene group, a substituted or unsubstituted heterocycloalkylene group, a substituted or unsubstituted heterocycloalkenylene group, or a combination comprising at least one of the foregoing groups, and n is 0 or 1.

According to another embodiment, an electrochromic device includes a first electrode and a second electrode facing each other, an electrochromic material on either one of the first electrode and the second electrode, and an electrolyte layer located between opposing surfaces of the first electrode and the second electrode, and the electrochromic material includes a compound represented by Chemical Formula 1.

$R_1$ may be one of the following Chemical Formula 2:

Chemical Formula 2

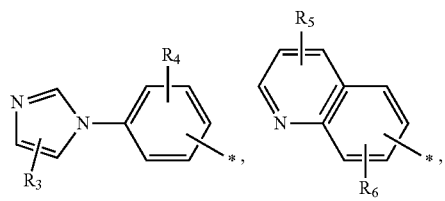

-continued

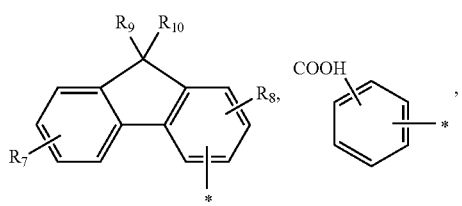

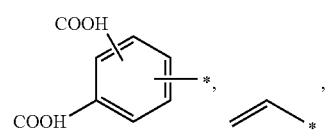

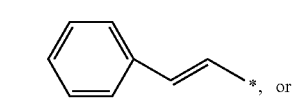

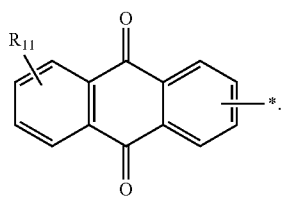

In Chemical Formula 2, $R_3$ to $R_{11}$ are each independently a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C7 to C30 aralkyl group, a substituted or unsubstituted C2 to C30 heteroaryl group, a substituted or unsubstituted C3 to C30 heteroaralkyl group, or a combination comprising at least one of the foregoing groups.

$R_2$ may include a group selected from the following Chemical Formulae 2 and 3.

Chemical Formula 2

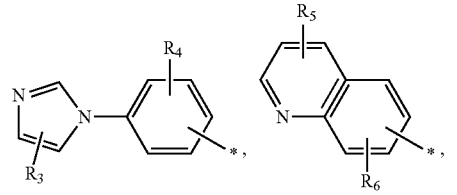

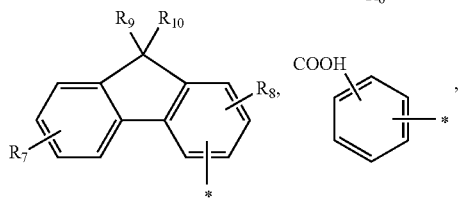

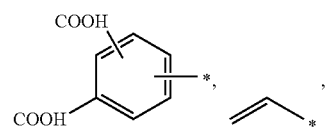

-continued

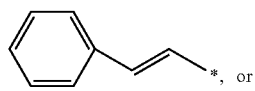

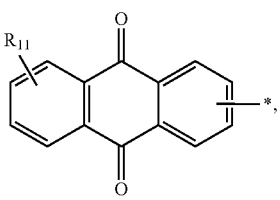

Chemical Formula 3

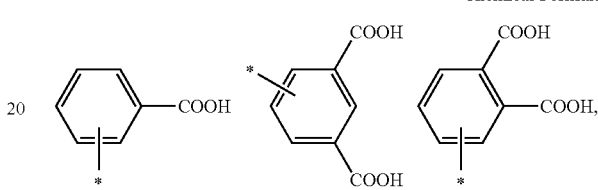

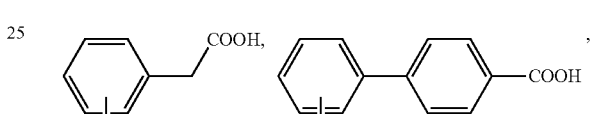

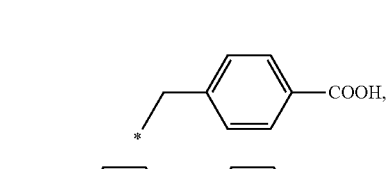

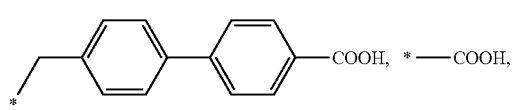

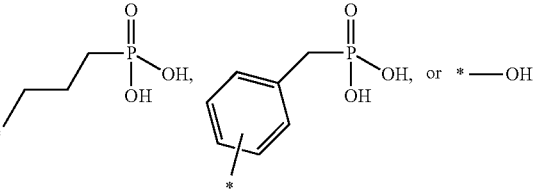

In Chemical Formula 2, $R_3$ to $R_{11}$ are each independently a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C7 to C30 aralkyl group, a substituted or unsubstituted C2 to C30 heteroaryl group, a substituted or unsubstituted C3 to C30 heteroaralkyl group, or a combination comprising at least one of the foregoing groups.

The electrochromic material may display different colors at different applied voltage ranges.

The electrochromic material may display green within a first voltage range, and red within a second voltage range.

The electrochromic material may include at least one compound represented by the following Chemical Formulae 1A to 1X.

Chemical Formula 1A
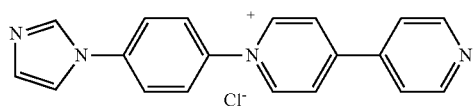
Chemical Formula 1B
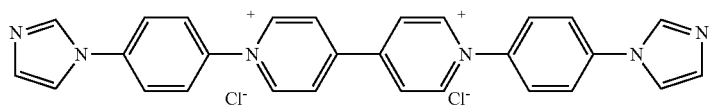
Chemical Formula 1C
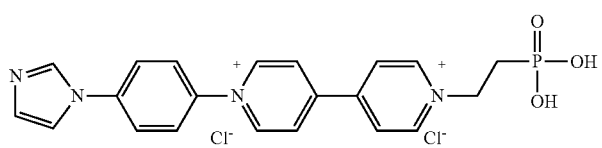
Chemical Formula 1D
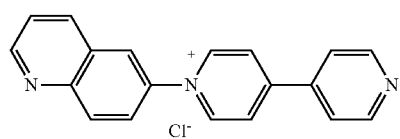
Chemical Formula 1E
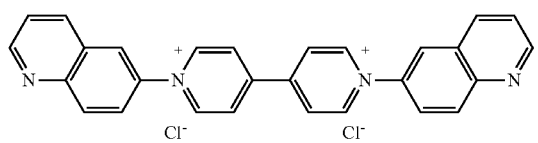
Chemical Formula 1F
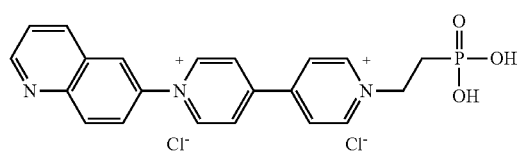
Chemical Formula 1G
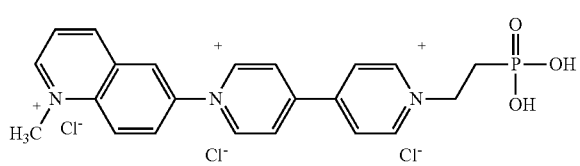
Chemical Formula 1H
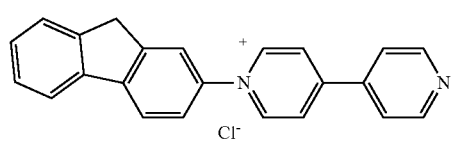
Chemical Formula 1I
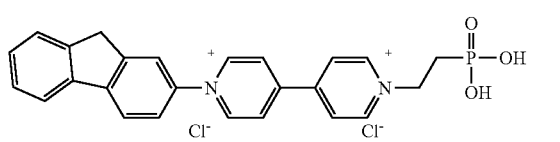
Chemical Formula 1J
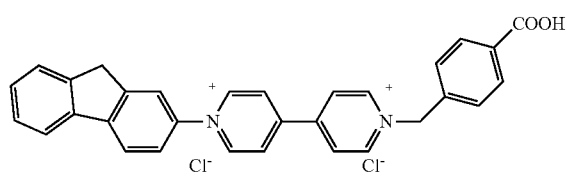
Chemical Formula 1K
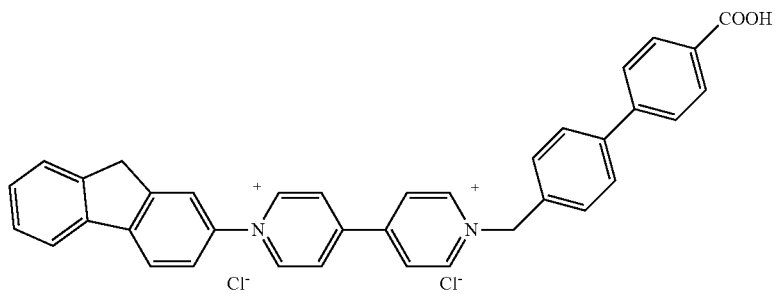
Chemical Formula 1L
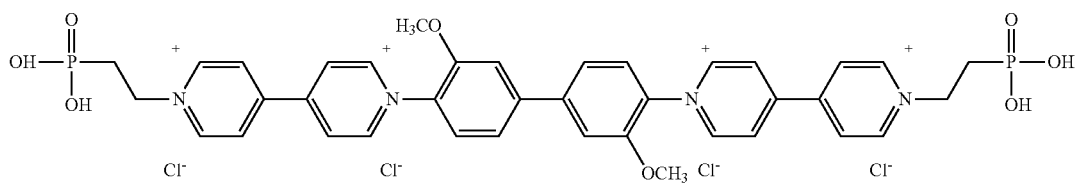

-continued

Chemical Formula 1M

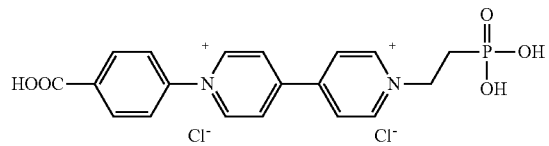

Chemical Formula 1N

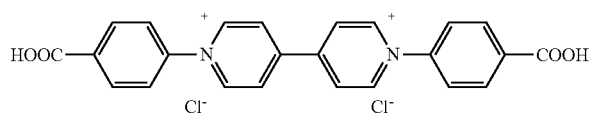

Chemical Formula 1O

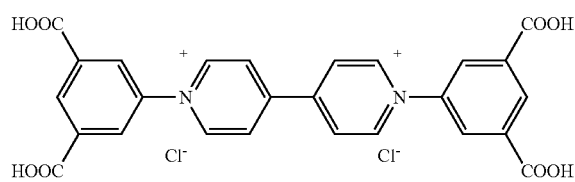

Chemical Formula 1P

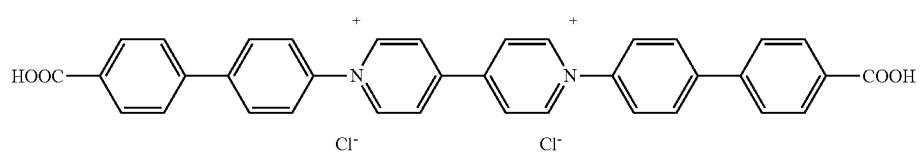

Chemical Formula 1Q

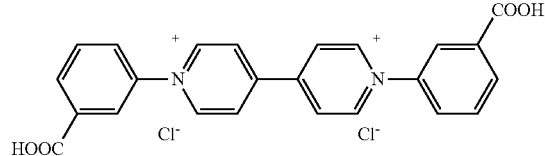

Chemical Formula 1R

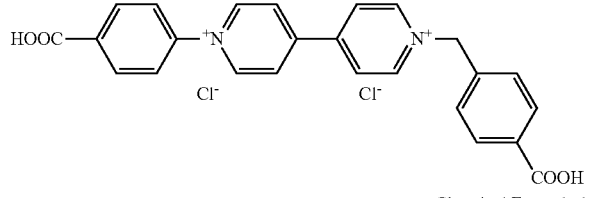

Chemical Formula 1S

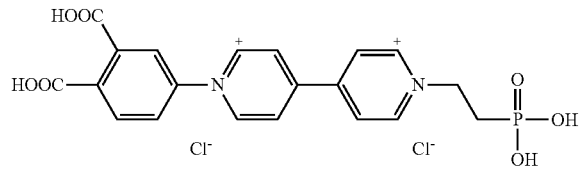

Chemical Formula 1T

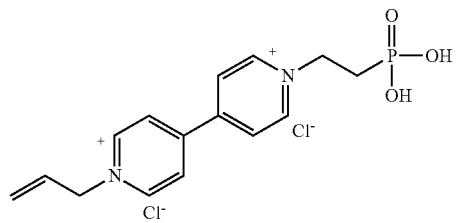

Chemical Formula 1U

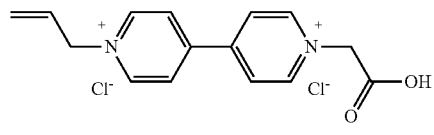

Chemical Formula 1V

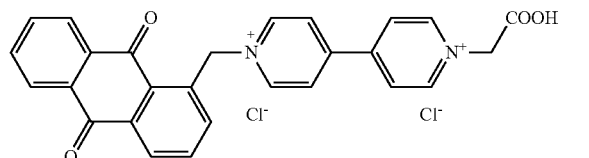

Chemical Formula 1W

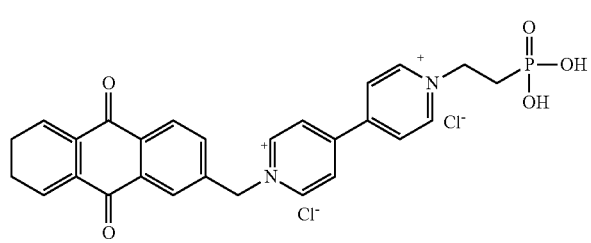

Chemical Formula 1X

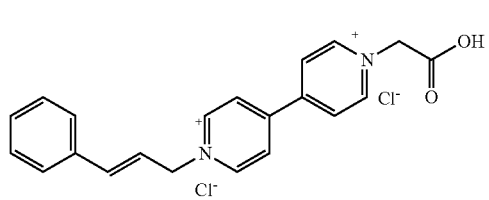

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
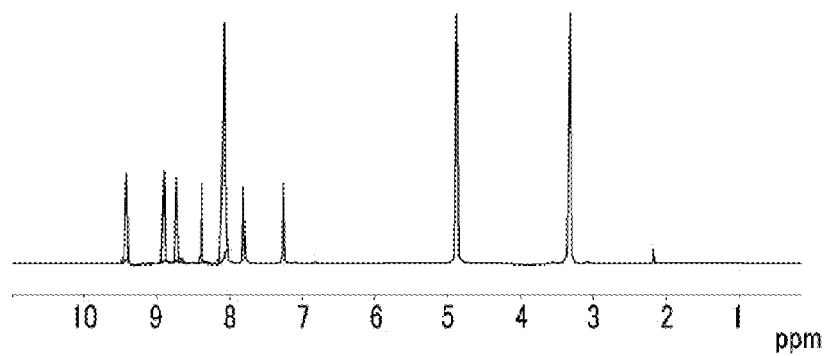
FIGS. 1A, 1B, and 1C are respectively a $^1$H NMR spectrum, a photograph showing the color within a first voltage range, and a photograph showing the color within a second voltage range for the electrochromic material according to Example 1.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

As used herein, "Alkyl" refers to a straight or branched chain saturated aliphatic hydrocarbon having the specified number of carbon atoms. "Alkenyl" is a straight or branched chain hydrocarbon that comprises at least one carbon-carbon double bond. "Alkoxy" refers to an alkyl moiety that is linked via an oxygen (i.e., —O-alkyl). The term "alkylene" refers to a straight, branched or cyclic divalent aliphatic hydrocarbon group. The term "alkenylene" refers to a straight, branched or cyclic divalent aliphatic hydrocarbon group containing a double bond. As used herein "aryl," means a cyclic moiety in which all ring members are carbon and at least one ring is aromatic. More than one ring may be present, and any additional rings may be independently aromatic, saturated or partially unsaturated, and may be fused, pendant, spirocyclic or a combination thereof. An "aralkyl" group is an aryl group linked via an alkylene moiety. The specified number of carbon atoms (e.g., C7 to C30) refers to the total number of carbon atoms present in both the aryl and the alkylene moieties. Representative aralkyl groups include, for example, benzyl groups. An "aralkylene" group is an arylene group linked by two or more alkylene moieties. As used herein, the term "arylene" refers to a divalent radical formed by the removal of two hydrogen atoms from one or more rings of an aromatic hydrocarbon, wherein the hydrogen atoms may be removed from the same or different rings (preferably different rings), each of which rings may be aromatic or nonaromatic. "Aryloxy" refers to an aryl moiety that is linked via an oxygen (i.e., —O-aryl). "Cycloalkylene" refers to a divalent radical formed by the removal of two hydrogen atoms from one or more rings of a cycloalkyl group (a nonaromatic hydrocarbon that comprises at least one ring). A "heteroalkyl" group is an alkyl group that comprises at least one heteroatom covalently bonded to one or more carbon atoms of the alkyl group. A "heteroaryl" group is a monovalent carbocyclic ring system that includes one or more aromatic rings, in which at least one ring member (e.g., one, two or three ring members) is a heteroatom. "Heteroarylene" refers to a divalent radical formed by the removal of two hydrogen atoms from one or more rings of a heteroaryl moiety, wherein the hydrogen atoms may be removed from the same or different rings (preferably the same ring), each of which rings may be aromatic or nonaromatic. As used herein, "combination" is inclusive of blends, mixtures, alloys, reaction products, and the like. A "heteroaralkyl" group is a heteroaryl group linked via an alkylene moiety. A "heteroaralkylene" group is a heteroarylene group linked via two or more alkylene moieties. A "heterocycloalkylene" group is a heteroatom-containing cycloalkylene group. "Cyclo" refers to a moiety having a ring structure, where multiple rings, if present, may be pendant, Spiro or fused.

When a definition is not otherwise provided, the terms "alkyl group", "alkenyl group", "alkynyl group", "alkylene group", "alkenylene group", "cycloalkylene group", "cycloalkenylene group", and "alkoxy group", refer to a C1 to C30 alkyl group, a C2 to C30 alkenyl group, a C2 to C30 alkylene group, a C2 to C30 alkenylene group, a C3 to C30 cycloalkylene group, a C3 to C30 cycloalkenylene group, and a C1 to C30 alkoxy group, respectively, and "aryl group", "arylene group", and "aryloxy group", refer to a C6 to C30 aryl group, a C6 to C30 arylene group, and a C6 to C30 aryloxy group, respectively.

When a definition is not otherwise provided, the terms "heteroarylene group" and "heteroaralkylene group" refer to a heteroarylene and a heteroaralkylene including a heteroatom of N, O, S, or P in an arylene ring. The terms "heterocycloalkylene group" and "heterocycloalkenylene group" refer to a heterocycloalkylene group and a heterocycloalkenylene group including at least one heteroatom of an N, O, S, or P heterocycloalkylene group, and heterocycloalkenylene group.

As used herein, when a definition is not otherwise provided, the term "substituted" refers to one substituted with a substituent selected from a halogen (F, Cl, Br, I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group, or a salt thereof, a sulfonic acid group or a salt thereof, a phosphoric acid group or a salt thereof, a C1 to C20 alkyl group, a C2 to C16 alkynyl group, a C6 to C20 aryl group, a C7 to C13 arylalkyl group, a C1 to C4 oxyalkyl group, a C1 to C20 heteroalkyl group, a C3 to C20 heteroarylalkyl group, a C3 to C20 cycloalkyl group, a C3 to C15 cycloalkenyl group, a C6 to C15 cycloalkynyl group, a C2 to C20 heterocycloalkyl group, and a combination thereof, instead of hydrogen. Also, where "phthalic acid" is referred to, it will be understood that unless otherwise specified, "a phthalic acid" refers generally to o-phthalic acid, m-phthalic acid (also referred to as isophthalic acid), p-phthalic acid (also referred to as terephthalic acid), or a combination of two or more of these phthalic acids.

As used herein and throughout the specification, in a structure where a group (e.g., CH₃, F, R₁, etc.) is not shown at the terminus of a bond, the asterisks (*) represent the point of attachment of the group ($R_1$ or $R_2$) to another structure.

Hereinafter, the electrochromic material according to one embodiment is described.

The electrochromic material may be a single electrochromic compound or a mixed electrochromic compound including two or more electrochromic compounds.

The electrochromic material according to one embodiment is represented by the following Chemical Formula 1.

Chemical Formula 1

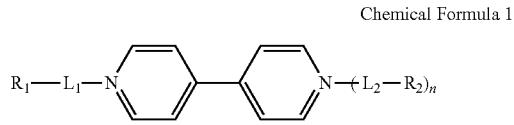

In Chemical Formula 1, $R_1$ is a substituted or unsubstituted imidazole, a substituted or unsubstituted oxazole, a substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group, or a combination comprising at least one of the foregoing groups. It will be appreciated that where "a fluorine containing group" is indicated, the group may be fluorine, a C1 to C30 fluoroalkyl group, a C2 to C30 fluoroalkenyl group, a C6 to C30 fluoroaryl group, or a C7 to C30 fluoroaralkyl group, where at least one fluorine atom may be present. Exemplary fluorine containing groups may include fluorine, trifluoromethyl, 1,1,1-trifluoroethyl, perfluoroethyl, perfluorobutyl, trifluoromethylphenyl, 3,5-bis(trifluoromethyl)phenyl, trifluoromethylbenzyl, 3,5-bis(trifluoromethyl)benzyl, and the like.

$R_2$ is a substituted or unsubstituted imidazole, a substituted or unsubstituted oxazole, a substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group; a phosphonium acid group; a carboxylic acid group; a sulfonic acid group; a hydroxy group; a substituted or unsubstituted C1 to C30 alkyl group, a substituted or unsubstituted C3 to C30 cycloalkyl group, a substituted or unsubstituted C6 to C30 aryl group, or a substituted or unsubstituted C2 to C30 heteroaryl group substituted with a phosphonium acid group, a carboxylic acid group, a sulfonic acid group, or a hydroxy group; or a combination comprising at least one of the foregoing groups.

$L_1$ and $L_2$ are each independently a single bond, a substituted or unsubstituted C1 to C30 alkylene group, a substituted or unsubstituted C3 to C30 cycloalkylene group, a substituted or unsubstituted C2 to C30 heterocycloalkylene group, a substituted or unsubstituted C6 to C30 arylene group, a substituted or unsubstituted C7 to C30 aralkylene group, a substituted or unsubstituted C2 to C30 heteroarylene group, a substituted or unsubstituted C3 to C30 heteroaralkylene group, a substituted or unsubstituted heterocycloalkylene group, a substituted or unsubstituted heterocycloalkenylene group, or a combination comprising at least one of the foregoing.

n is 0 or 1.

In Chemical Formula 1, $R_1$ may be selected from the groups of the following Chemical Formula 2.

Chemical Formula 2

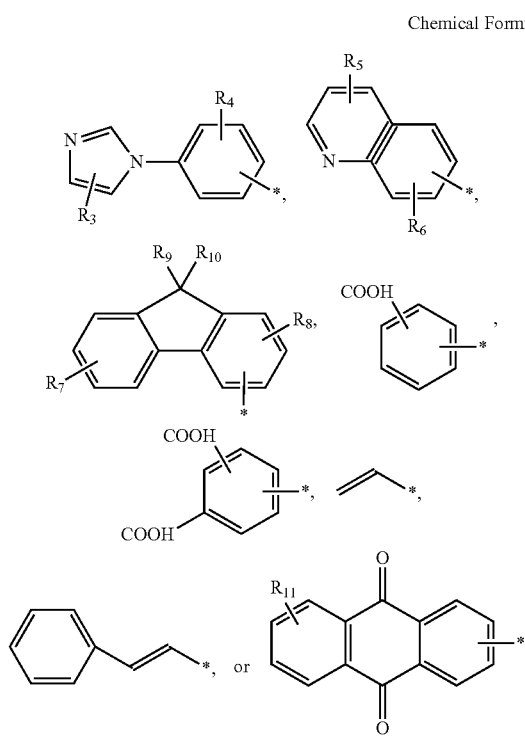

In Chemical Formula 2, $R_3$ to $R_{11}$ are each independently a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C7 to C30 aralkyl group, a substituted or unsubstituted C2 to C30 heteroaryl group, a substituted or unsubstituted C3 to C30 heteroaralkyl group, In Chemical Formula 1, $R_2$ may be one of the groups represented by the following Chemical Formulae 2 and 3.

Chemical Formula 2

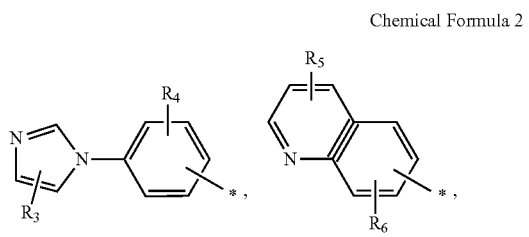

-continued

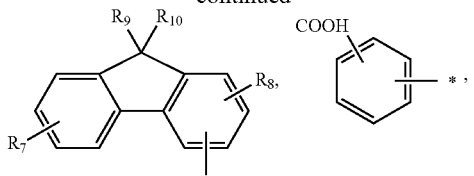

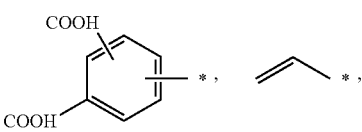

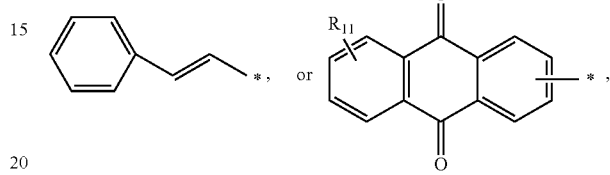

where, in Chemical Formula 2, $R_3$ to $R_{11}$ are as described above;

Chemical Formula 3

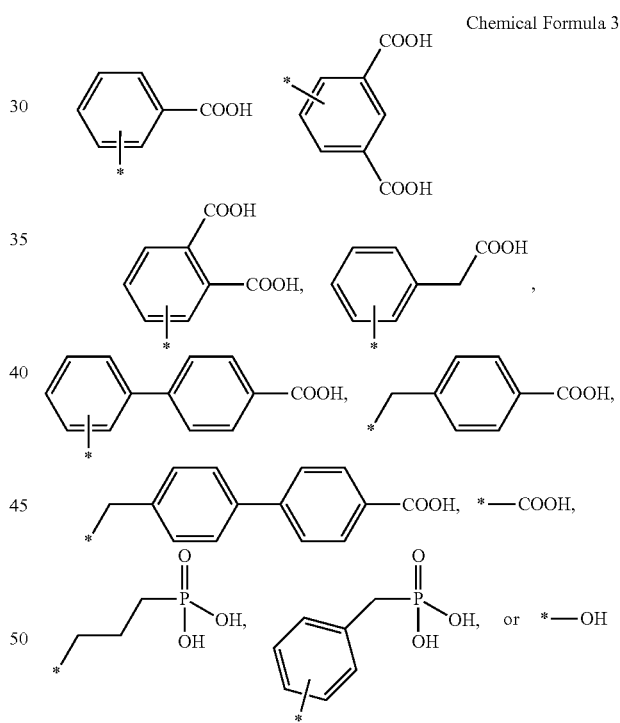

The electrochromic material is a multicolor electrochromic material that displays different colors at different voltage ranges. The electrochromic material may display different colors depending on different voltage ranges by an oxidation-reduction reaction. For example, an electrochromic material may display green within a first voltage range, and red within a second voltage range. Preferably, the second voltage range may be higher than the first voltage range.

As shown in Chemical Formula 1, the electrochromic material according to the present embodiment includes a viologen moiety and a substituent bound to one side or both sides of the viologen.

A viologen is a quaternary salt derivative of a 4,4'-bipyridyl compound, in which color reversibly changes by oxidation and reduction of the viologen rings.

A substituent bound to either one or both ends of the viologen moiety may control electron mobility and thus adjust oxidation and reduction states (potential) of the compound.

In Reaction Scheme 1, (A) shows an oxidation state that does not display a color, while (B) show a first reduction state displaying a color and (C) shows a second reduction state displaying a color. Herein, the first and second reduction states respectively display a different color; for example, the step (B) may display green and the step (C) may display red.

Reaction Scheme 1

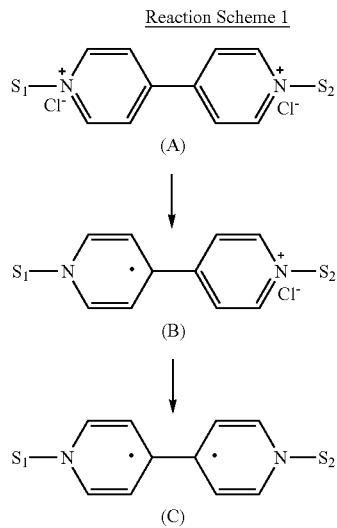

According to the embodiment, an electrochromic material may in this way be a multicolor electrochromic material displaying two or more colors by adjusting the reduction state of the viologen moiety by adding or removing electrons.

Hereinafter, an electrochromic device using the electrochromic material is described referring to FIG. 22.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present. Also as used herein, "facing" means where surfaces of two layers, films, regions, or substrates are opposite to and coplanar with each other, where the two surfaces may be on (i.e., with another layer intervening) or directly on one another.

Figure 22:
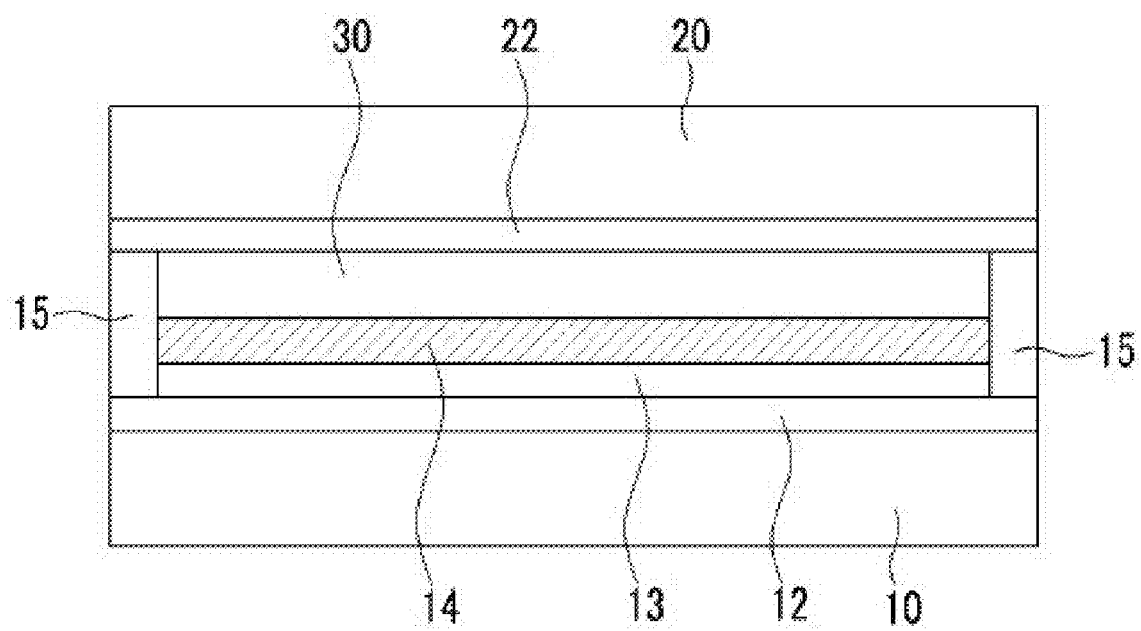
FIG. 22 is a cross-sectional view of an electrochromic device according to one embodiment.

FIG. 22 is the schematic cross-sectional view of an electrochromic device according to one embodiment.

Referring to FIG. 22, the electrochromic device according to one embodiment includes a pair of substrates 10 and 20 facing each other, and first and second electrodes 12 and 22 positioned on the substrates 10 and 20, respectively.

The substrates 10 and 20 may be formed of a transparent material such as, for example, glass or plastic. Examples of the plastic include one or more materials selected from the group consisting of polyacrylate, polyethylene etherphthalate, polyethylene naphthalate, polycarbonate, polyarylate, polyetherimide, polyethersulfone, polyimide, and any combination thereof. Herein and throughout the specification, a combination, such as a combination of plastics, may be an intimate admixture or blend, or may be a multilayered structure in which discrete layers, e.g., of the plastic(s), are included.

The first electrode 12 includes a transparent conductive material, for example, an inorganic conductive material including indium tin oxide ("ITO") or fluorine-doped tin oxide ("FTO"), or an organic conductive material such as polyacetylene, polyphenylene-vinylene, polyaniline, polypyrrole, polythiophene, or derivatives of these organic conductive materials. Combinations comprising at least one of the foregoing conductive materials may be used.

The second electrode 22 may be formed of a transparent conductive material, for example, indium tin oxide (ITO), fluorine-doped tin oxide (FTO), antimony-doped tin oxide ("ATO"), or a translucent or opaque conductive material such as a metal including as aluminum (Al) or an alloy thereof, or a combination thereof.

On the first electrode 12, an electrochromic layer 14 including the electrochromic material is provided. An auxiliary layer 13 may be positioned between the first electrode 12 and the electrochromic layer 14 to improve adherence of the electrochromic layer 14 to the substrate 10. The auxiliary layer 13 may include, for example, titanium oxide ($TiO_2$), aluminum oxide ($Al_2O_3$), and the like, and may be omitted as needed.

A reflector (not shown) may be positioned between the second electrode 22 and the substrate 20.

The substrates 10 and 20 are held at a fixed distance from one another by spacers 15, and an electrolyte 30 is included to fill the gap between the substrates 10 and 20. The electrolyte 30 includes an oxidation-reduction material for reacting electrochemically with the electrochromic material, and may be a liquid electrolyte or a solid polymer electrolyte. Liquid electrolytes may include, for example, a solution of a lithium salt such as LiOH or $LiClO_4$, a potassium salt such as KOH, or a sodium salt such as NaOH and dissolved in an organic or aqueous-based solvent, but is not limited thereto. The solid electrolyte may include, for example, poly(2-acrylamino-2-methylpropane sulfonic acid), polyvinyl pyrrolidine, or polyalkylene ethers such as polyethylene oxide, polypropylene oxide, or copolymers thereof, but is not limited thereto.

The following examples illustrate this disclosure in more detail. However, it is understood that this disclosure is not limited by these examples.

EXAMPLE 1

Synthesis of Chemical Formula 1A Compound

Chemical Formula 1A

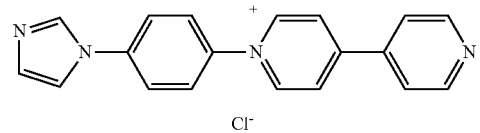

1 mmol (0.159 g) of N-(4-amino)phenylimidazole and 2 mmol (0.716 g) of 4-(2,4-dinitrophenyl)-4,4-dipyridyl chloride are dissolved in 100 ml of ethanol. The mixture is heated at reflux for 2 days. Then, a yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven, to provide the compound of Chemical Formula 1A. The yield is about 70%.

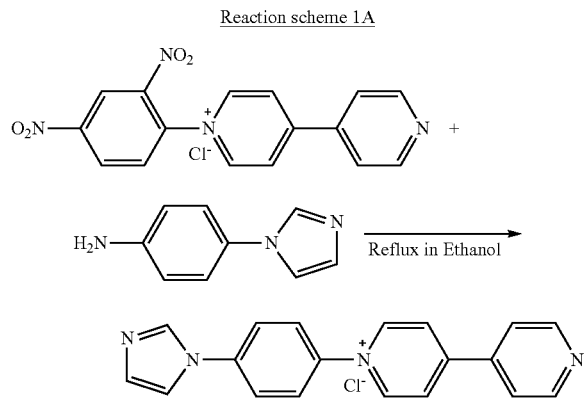

Reaction scheme 1A

The structure of the compound represented by chemical formula 1A is identified by its $^1$H NMR spectrum (Refer to FIG. 1A).

The chemical shift is measured in deuterated dimethylsulfoxide (DMSO-$d_6$) solution and is referenced to tetramethylsilane ("TMS"). $^1$H-NMR (DMSO-$d_6$/TMS) δ (ppm): 9.57 (2H, d, pyridine proton), 8.93 (2H, d, pyridine proton), 8.83 (2H, d, pyridine proton), 8.58 (1H, d), 8.18 (2H, d, pyridine proton), 8.18 (2H, d, pyridine proton), 8.16-8.09 (4H, m, phenyl proton), 8.00 (1H, d), 7.24 (1H, s).

Fabrication of Electrochromic Device

The electrochromic material prepared according to the method mentioned above and 0.05 mmol of $LiClO_4$ as an electrolyte are dissolved in 100 ml gamma-butyroacetone, to prepare an electrochromic solution. Next, ITO and ATO electrodes are respectively formed on two sheets of glass as substrates, and titanium oxide ($TiO_2$) is coated to a thickness of 10 micrometer on the ITO electrode by screen print method. The glass substrates are positioned so that the electrodes are separated by a spacer to leave a predetermined gap between the electrodes, and the electrodes are sealed in place using the spacer. Then, the electrochromic solution is injected between the glass substrates, to complete the electrochromic device.

Electrochromic Characteristic Identification

A voltage of 0V to 2.2V is applied to the electrochromic device, and the following electrochromic characteristics are observed.

Figure 1B:
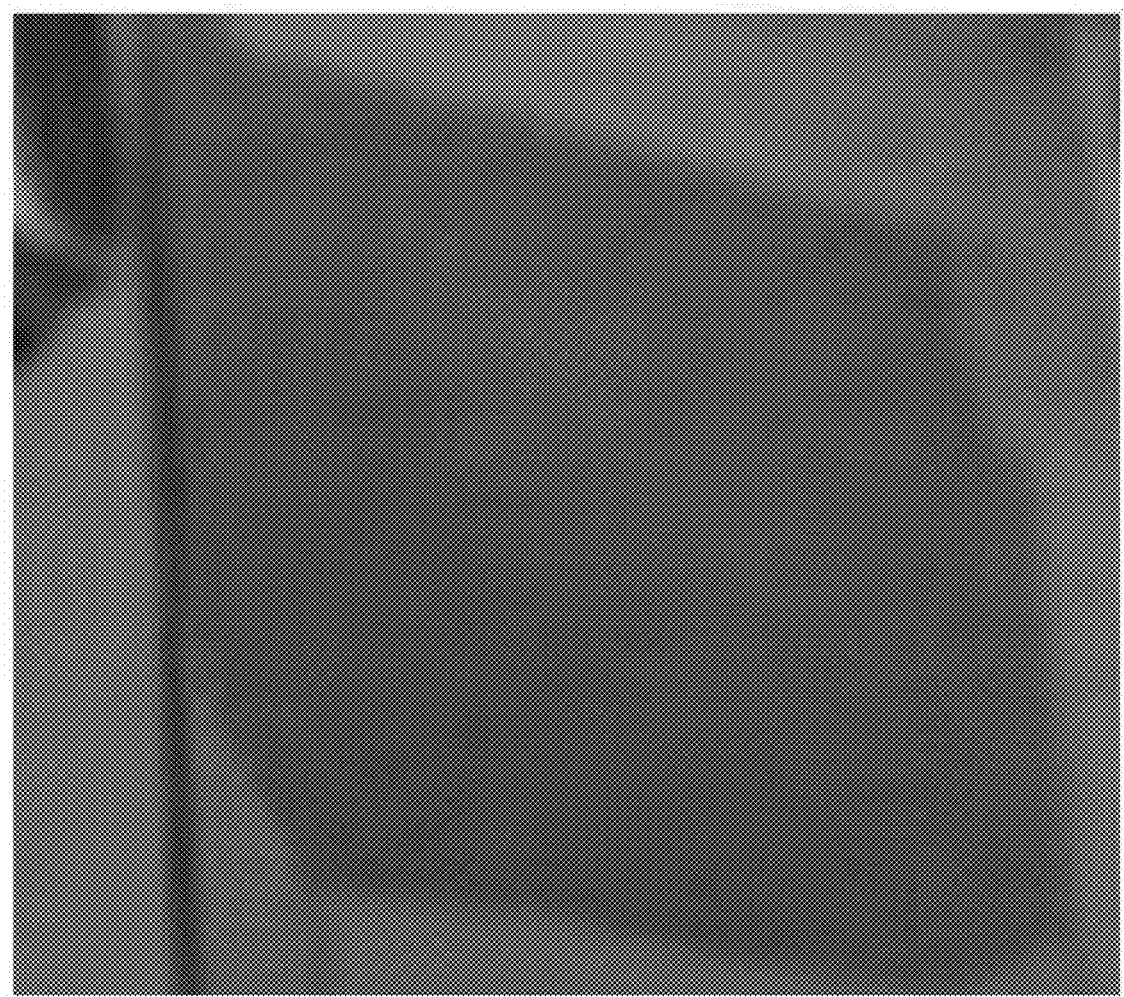
Figure 1C:
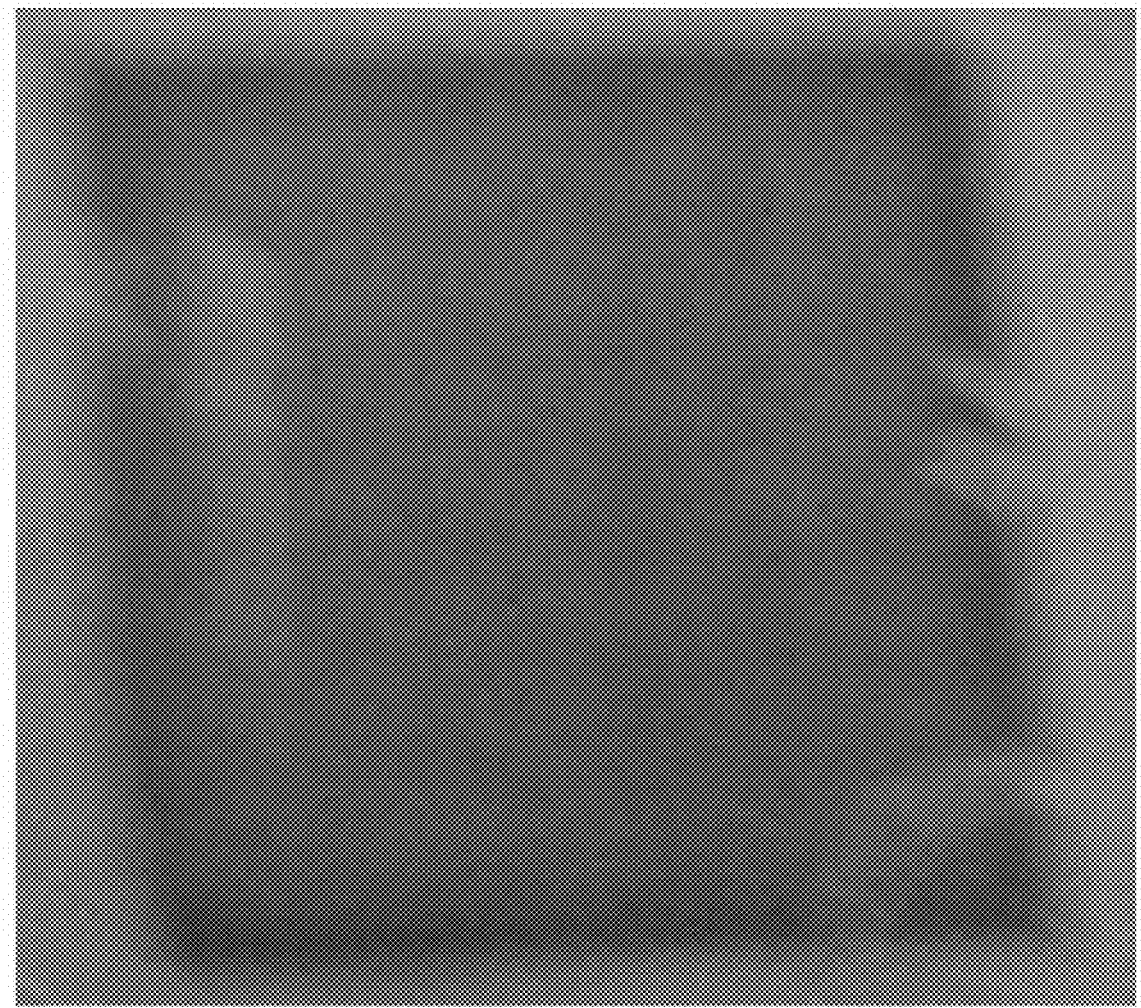
Figure 2A:
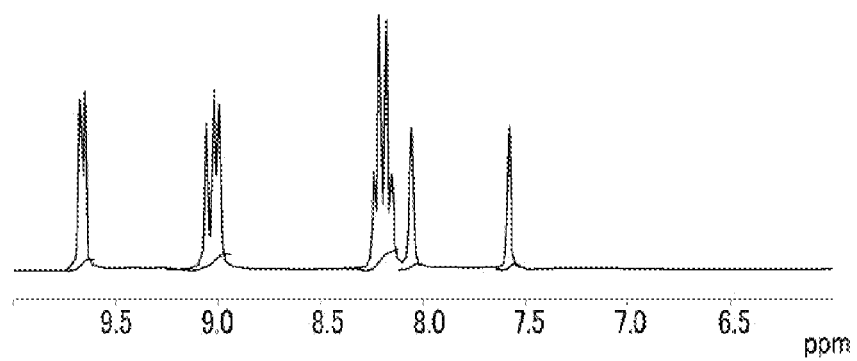
FIGS. 2A, 2B, and 2C are respectively a $^1$H NMR spectrum, a photograph showing the color within a first voltage range, and a photograph showing the color within a second voltage range for the electrochromic material according to Example 2.
Figure 2B:
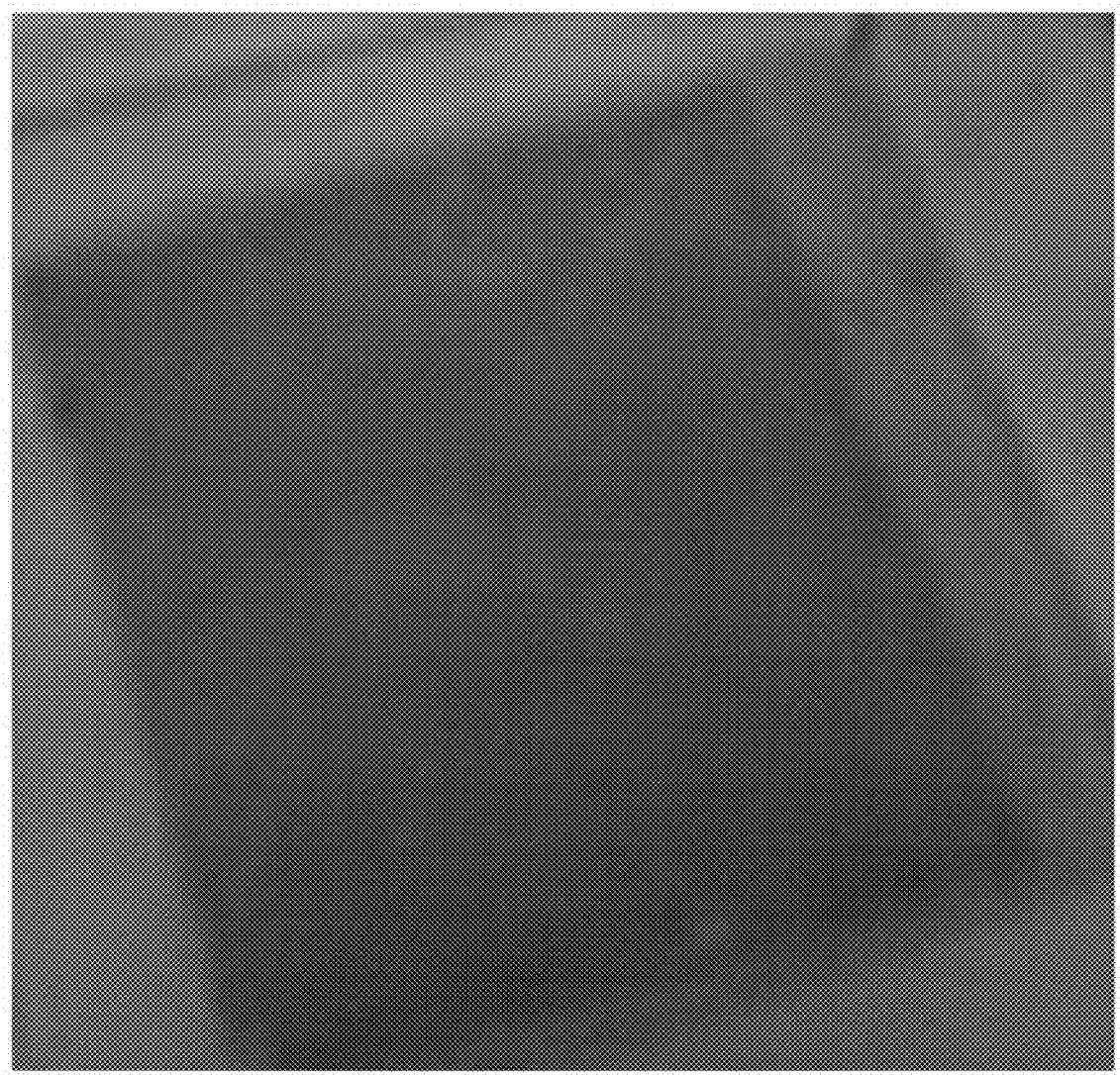
Figure 2C:
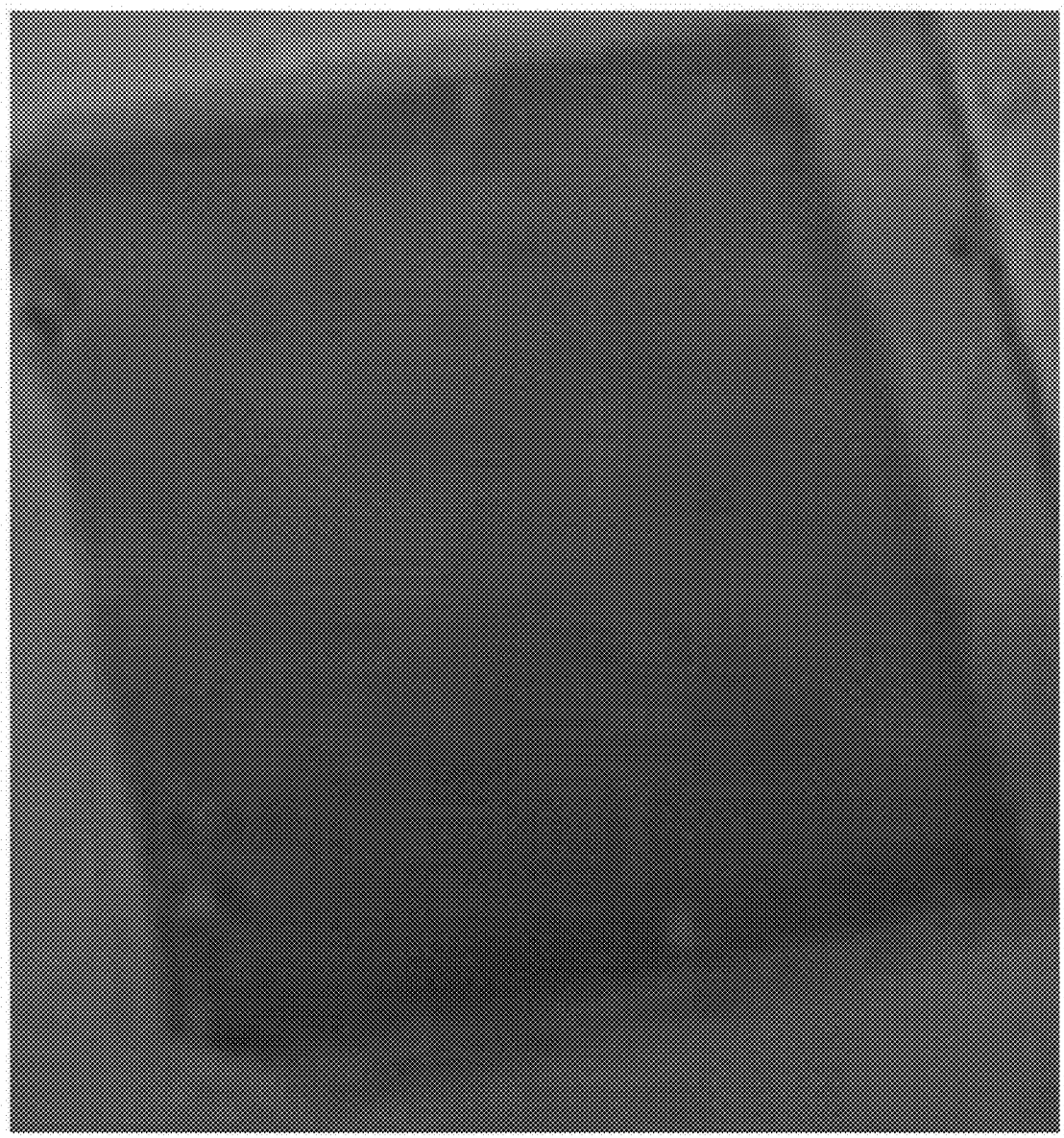

Referring to FIGS. 1B and 1C, the electrochromic device according to Example 1 has an operating voltage of about 0.8V, a potential window displaying green from about 0.8V to about 1.5V (FIG. 2B), and a potential window displaying red from about 1.6V to about 2.3V (FIG. 2C). The operating voltage refers to a voltage where electrochromism starts, and the potential window refers to a voltage range that maintains the same color.

The electrochromic device according to Example 1 displays different colors at different voltage ranges.

EXAMPLE 2

Synthesis of Chemical Formula 1B Compound

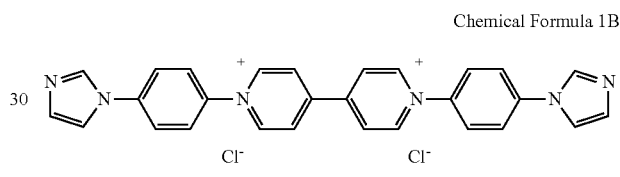

Chemical Formula 1B 10 mmol (1.590 g) of N-(4-amino)phenylimidazole and 1 mmol (0.560 g) of 4,4-bis-(2,4-dinitrophenyl)-4,4-dipyridyl dichloride are dissolved in 100 ml of ethanol. The mixture is heated at reflux for five days.

Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven, to provide the compound of Chemical Formula 1B. The yield is about 50%.

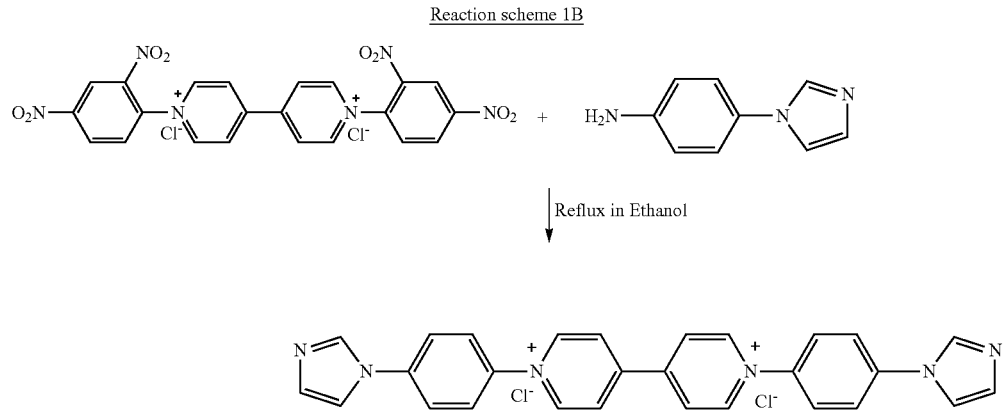

Reaction scheme 1B

The structure of the symmetric compound represented by chemical formula 1B is identified by its $^1$H NMR spectrum (Refer to FIG. 2A).

The chemical shift is measured in $D_2O$ solution and is referenced to sodium 2,2-dimethyl-2-silapentane-5-sulfonate ($^1$H-NMR ($D_2O$) δ (ppm): 9.66 (2H, d, pyridine proton), 9.05 (1H, s), 9.01 (2H, d, pyridine proton), 8.19 (q, 4H), 8.05 (1H, s), 7.57 (1H, s).

Fabrication of Electrochromic Device and Electrochromic Characteristic Identification An electrochromic device is fabricated according to the same method as in Example 1, except that the electrochromic material according to Example 2 is used. A voltage of 0V to 2.2V is applied to the electrochromic device, and the following electrochromic characteristics are observed.

Referring to FIGS. 2B and 2C, the electrochromic device according to Example 2 has an operating voltage of about 0.8V, a potential window displaying green of from about 0.8V to about 1.5V, and a potential window displaying red of from about 1.5V to about 1.8V.

EXAMPLE 3

Synthesis of Chemical Formula 1C Compound

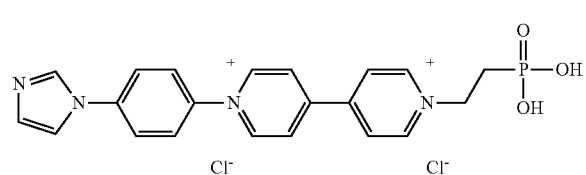

Chemical Formula 1C 1 mmol (0.334 g) of the Chemical Formula 1A compound and 15 mmol (3.225 g) of 1-bromoethyl phosphonate are dissolved in 300 ml of acetonitrile. The mixture is heated at reflux for five days.

Subsequently, the yellow residue is collected by filtration and dissolved in a minimum amount of methanol. Then, acetone is added thereto until a precipitate is produced. The precipitate is collected by filtration, rinsed with acetone several times, and dried. The yield is about 70%.

The thus-obtained compound is hydrolyzed in 50 ml of 37% (w/w) aqueous concentrated hydrochloric acid and the solvent is removed. Acetone is added to the resultant yellow solid followed by collection of the solid by filtration and dissolving it in a minimum amount of methanol. Next, acetone is added for reprecipitation, and it is then collected by filtration and dried, to provide a compound represented by Chemical Formula 1C. The yield is about 80%.

Reaction scheme 1C

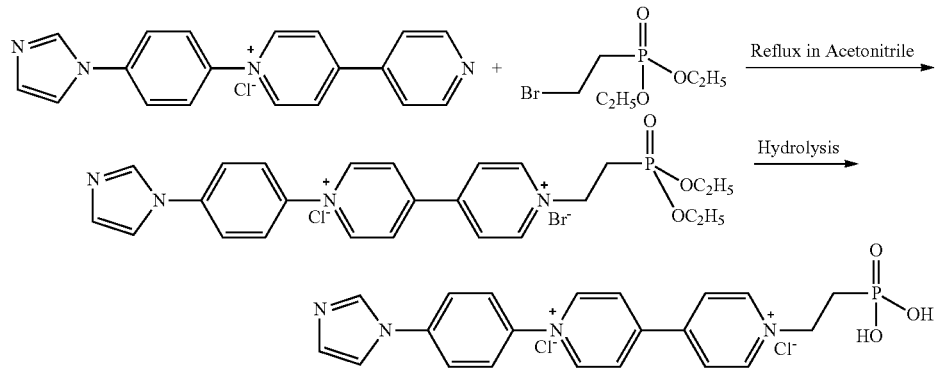

The structure of the compound represented by chemical formula 1C is identified by its $^1$H NMR spectrum.

Fabrication of Electrochromic Device and Electrochromic Characteristic Identification An electrochromic device is fabricated according to the same method as in Example 1, except that the electrochromic material according to Example 3 is used. A voltage of 0V to 2.2V is applied to the electrochromic device, and the following electrochromic characteristics are obtained.

Figure 3A:
FIGS. 3A and 3B are respectively a photograph showing the color within a first voltage range, and a photograph showing the color within a second voltage range for the electrochromic material according to Example 3.
Figure 3B:
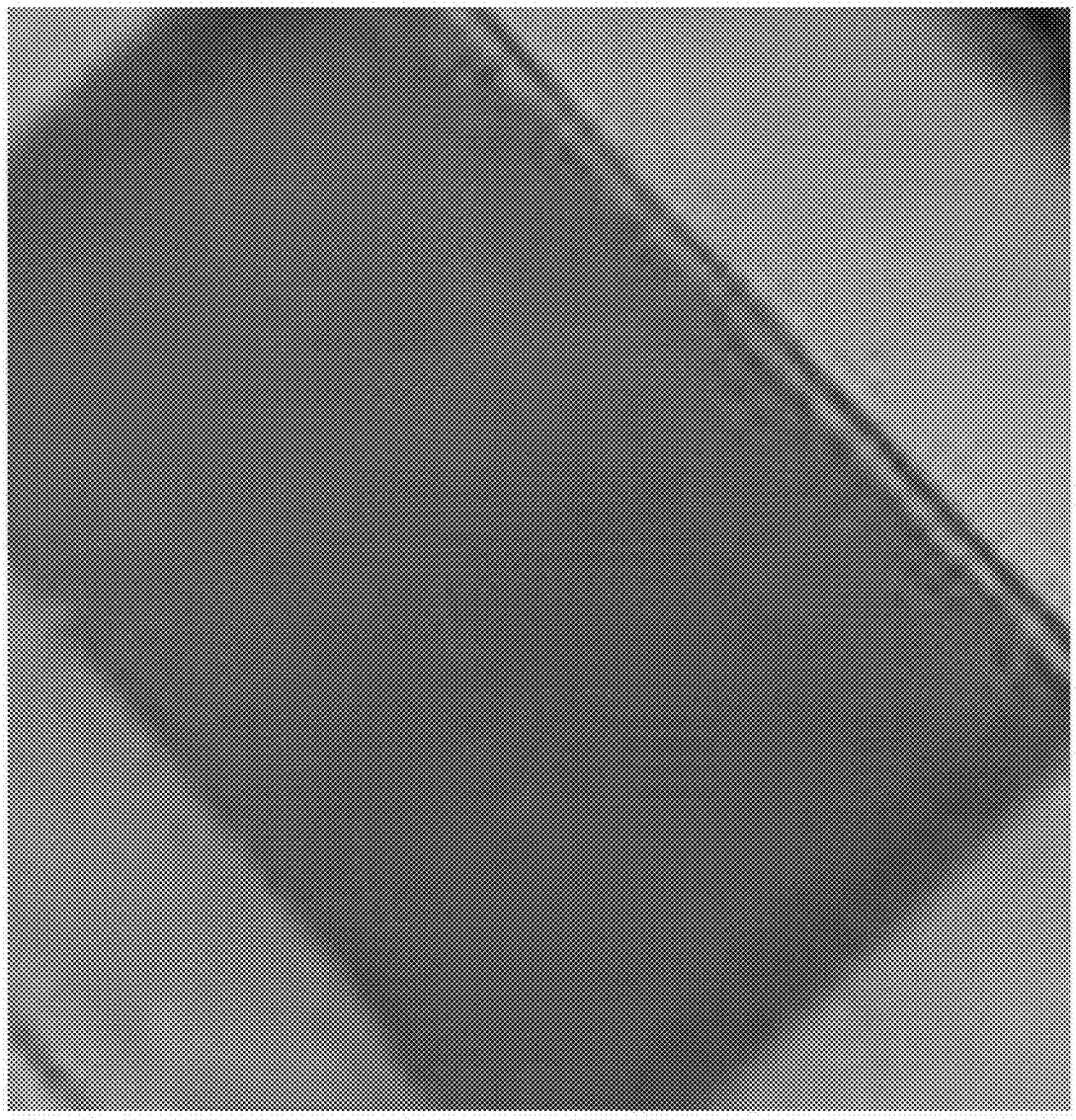

Referring to FIGS. 3A and 3B, the electrochromic device according to Example 3 has an operating voltage of about 0.8V, a potential window displaying green from about 0.8V to about 1.1V (FIG. 3A), and a potential window displaying red from about 1.5V to about 1.8V (FIG. 3B).

Figure 3C:
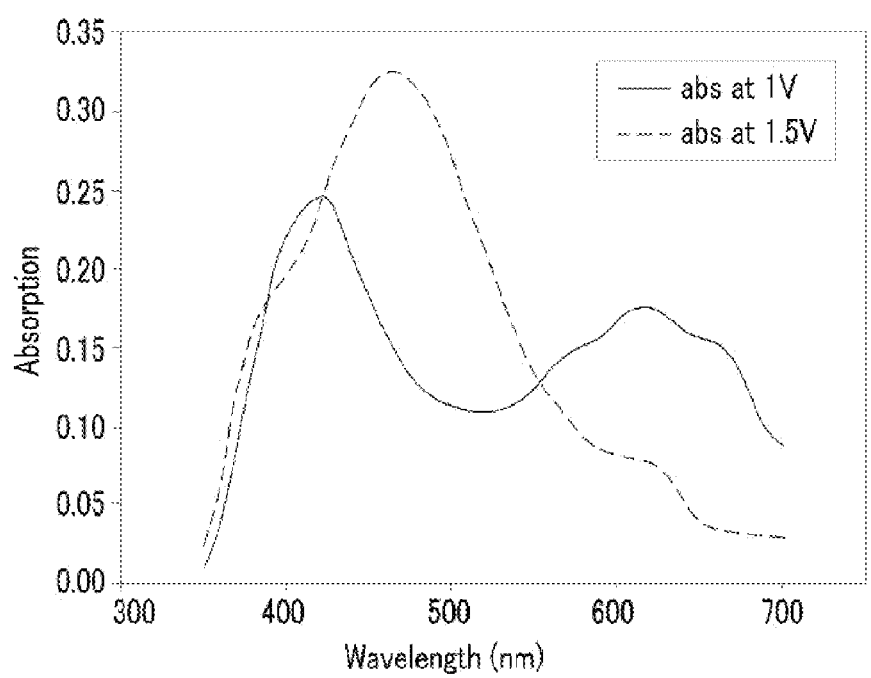
FIG. 3C is a plot of absorbance versus wavelength (in nanometers, m) at voltages of about 1V and about 1.5V.
Figure 3D:
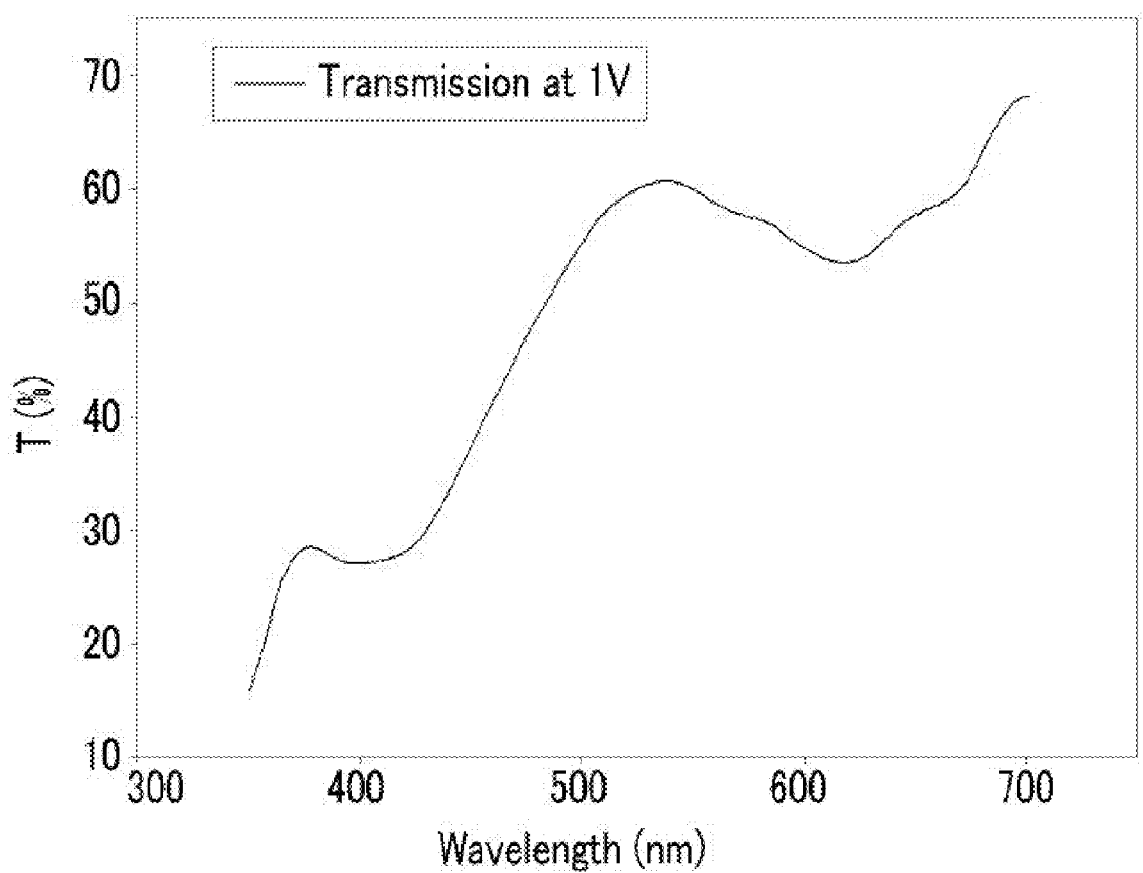
FIGS. 3D and 3E are respectively plots of transmittance versus wavelength (nm) at voltages of about 1V and about 1.5V.
Figure 3E:
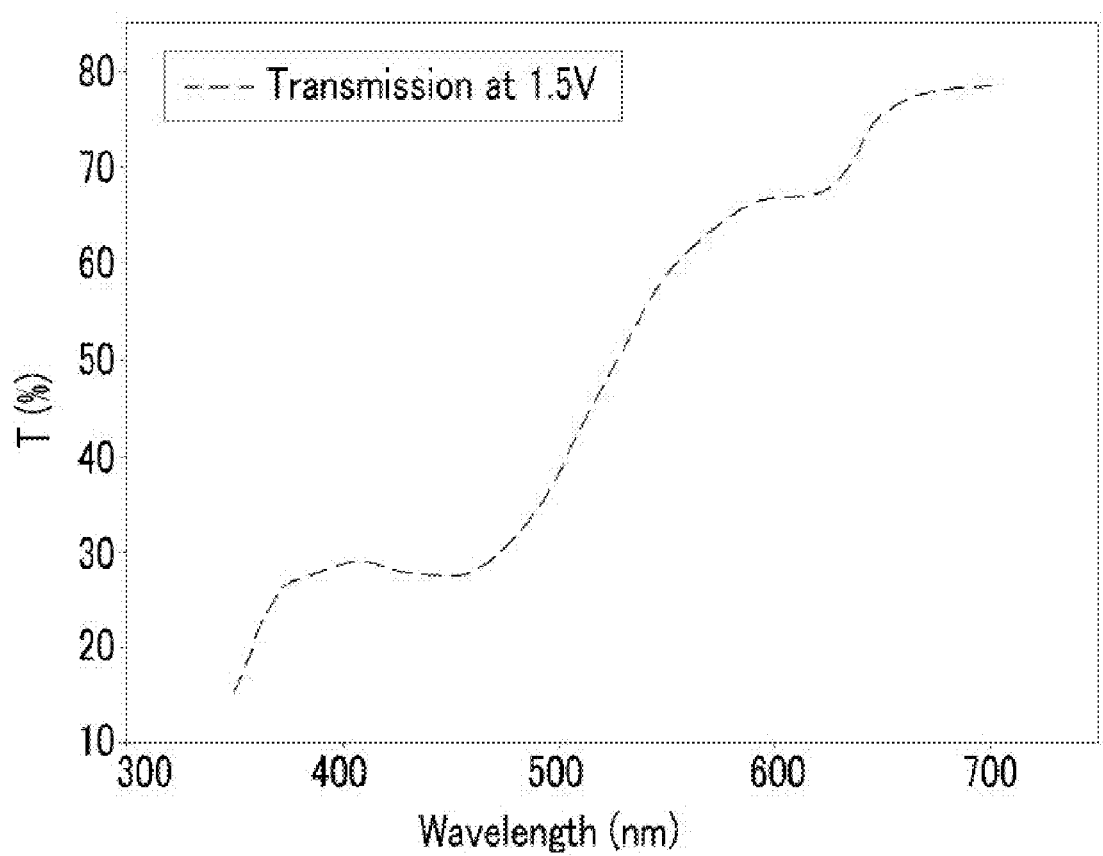

FIG. 3C is a plot of absorbance versus wavelength (in nm) for Chemical Formula 1C at a voltage of about 1V and about 1.5V, and FIGS. 3D and 3E are each respectively plots of transmittance versus wavelength (in nm) at a voltage of about 1V and about 1.5V.

Referring to FIGS. 3C to 3E, the absorption/transmission wavelength at about 1V and the absorption/transmission wavelength at about 1.5V are seen to be different. At about 1V, the green wavelength region (ca. 500-540 nm) has low absorbance and high transmittance, whereas at about 1.5V, the red wavelength region (>600 nm) has low absorbance and high transmittance.

EXAMPLE 4

Synthesis of Chemical Formula 1D Compound

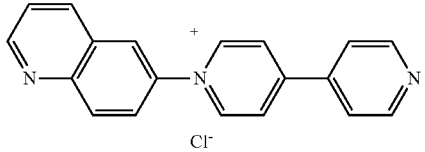

Chemical Formula 1D 1 mmol (0.144 g) of 6-aminoquinoline and 2 mmol (0.716 g) of 4-(2,4-dinitrophenyl)-4,4-dipyridyl chloride are dissolved in 100 ml of ethanol. The mixture is heated at reflux for 2 days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven, to provide the compound of Chemical Formula 1D. The yield is about 80%.

Reaction scheme 1D

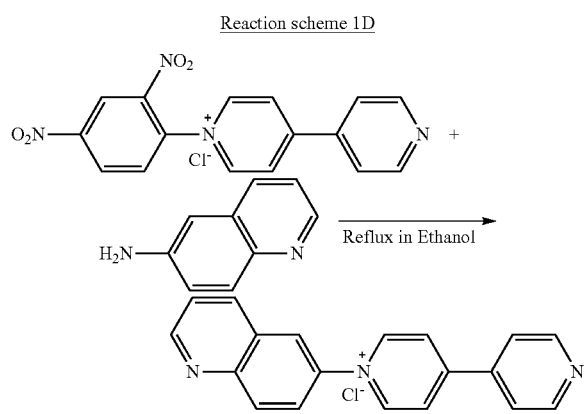

Figure 4:
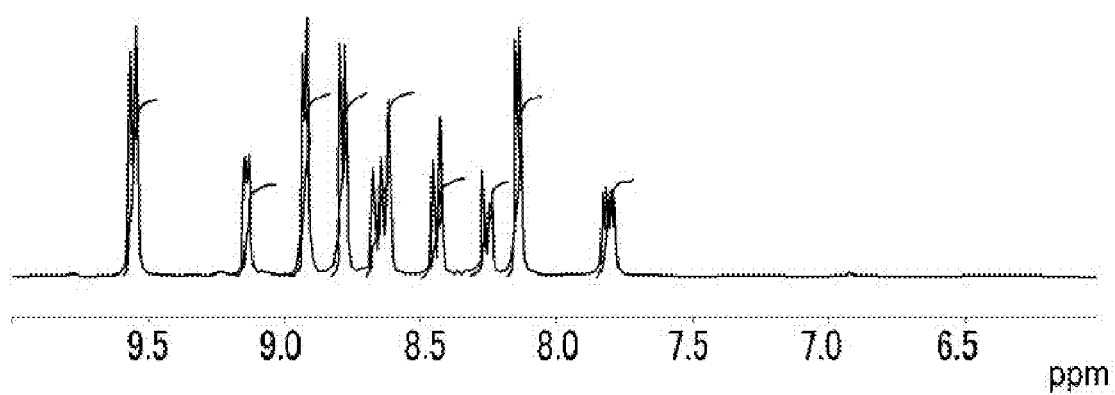
FIG. 4 is a $^1$H NMR spectrum of a electrochromic material according to Example 4.

The structure of the compound represented by chemical formula 1D is identified by its $^1$H NMR spectrum (Refer to FIG. 4).

The chemical shift is measured in $CD_3OD$ solution and is referenced to TMS. $^1$H-NMR ($CD_3OD$/TMS) δ (ppm): 9.55 (2H, d, pyridine proton), 9.13 (1H, s), 8.83 (2H, d, pyridine proton), 8.92 (2H, d, pyridine proton), 8.78 (2H, d), 8.70-8.58 (3H, m), 8.44 (1H, d), 8.25 (1H, d), 8.14 (2H, d, pyridine proton), 7.86-7.76 (q, 1H).

Fabrication of Electrochromic Device and Electrochromic Characteristic Identification.

An electrochromic device is fabricated according to the same method as in Example 1, except that the electrochromic material according to Example 4 is used. A voltage of 0 V to 2.2 V is applied to the electrochromic device, and the following electrochromic characteristics are observed.

The electrochromic device according to Example 4 has an operating voltage of about 0.8V, a potential window displaying light green from about 0.8V to about 1.5V, and a potential window displaying dark green from about 1.8V to about 2.2V.

EXAMPLE 5

Synthesis of Chemical Formula 1E Compound

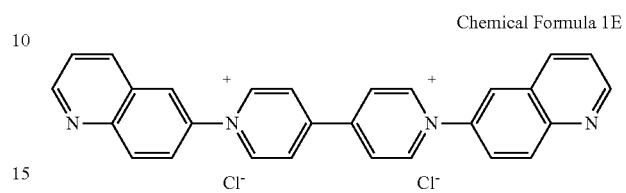

10 mmol (1.440 g) of 6-aminoquinoline and 1 mmol (0.560 g) of 4,4-bis-(2,4-dinitrophenyl)-4,4-dipyridyl dichloride are dissolved in 100 ml of ethanol. The mixture is heated at reflux for five days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven, to provide the compound of Chemical Formula 1E. The yield is about 40%.

Reaction scheme 1E

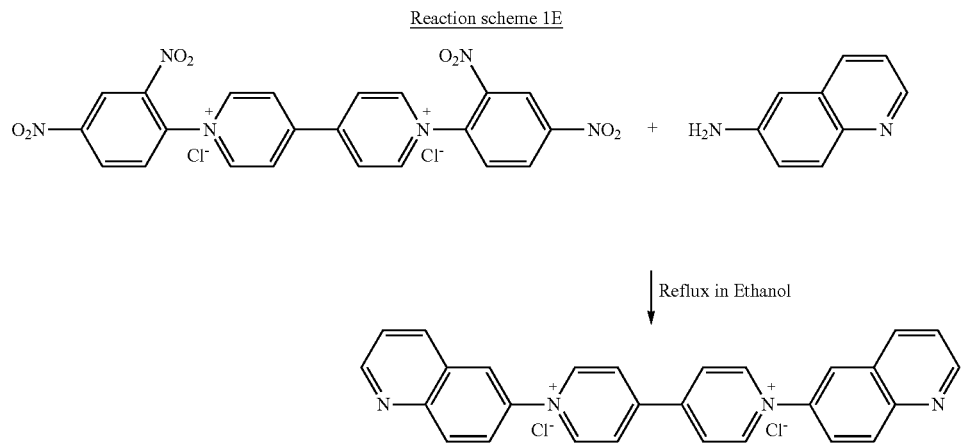

Figure 5:
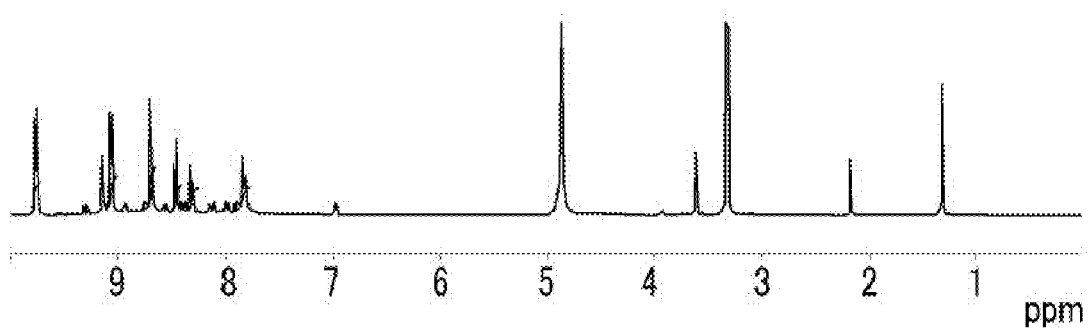
FIG. 5 is a $^1$H NMR spectrum of the electrochromic material according to Example 5.

The structure of the symmetric compound represented by chemical formula 1E is identified by its $^1$H NMR spectrum (Refer to FIG. 5).

The chemical shift is measured in $CD_3OD$ solution and is referenced to TMS. $^1$H-NMR ($CD_3OD$/TMS) δ (ppm): 9.77 (2H, d, pyridine proton), 9.15 (1H, s), 9.06 (2H, d, pyridine proton), 8.69 (2H, d), 8.47 (1H, d), 8.31 (1H, d), 7.86-7.79 (1H, q).

Fabrication of Electrochromic Device and Electrochromic Characteristic Identification An electrochromic device is fabricated according to the same method as in Example 1, except that the electrochromic material according to Example 5 is used. A voltage of 0V to 2.2V is applied to the electrochromic device and the following electrochromic characteristics are observed.

The electrochromic device according to Example 5 has an operating voltage of about 0.8V, a potential window displaying light green from about 0.8V to about 1.7V, and a potential window displaying dark green from about 1.8V to about 2.2V.

EXAMPLE 6

Synthesis of Chemical Formula 1F Compound

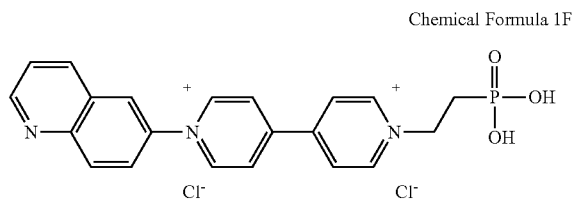

Chemical Formula 1F 1 mmol (0.320 g) of the Chemical Formula 1D compound and 15 mmol (3.225 g) of 1-bromoethyl phosphonate are dissolved in 300 ml of acetonitrile. The mixture is heated at reflux for 5 days. Subsequently, the yellow residue is collected by filtration and the resultant is dissolved in methanol. Then, acetone is added thereto until a compound is precipitated. The precipitate is collected by filtration, rinsed with acetone several times, and dried. The yield is about 70%.

The thus-obtained compound is hydrolyzed in 50 ml of 37% (w/w) concentrated aqueous hydrochloric acid and then the solvent is removed. Acetone is added to the resultant yellow solid followed by collection by filtration and dissolving in methanol. Next, acetone is added to the solution for reprecipitation, and the precipitate is then collected by filtration and dried, to provide a compound represented by Chemical Formula 1F. The yield is about 80%.

Reaction scheme 1F

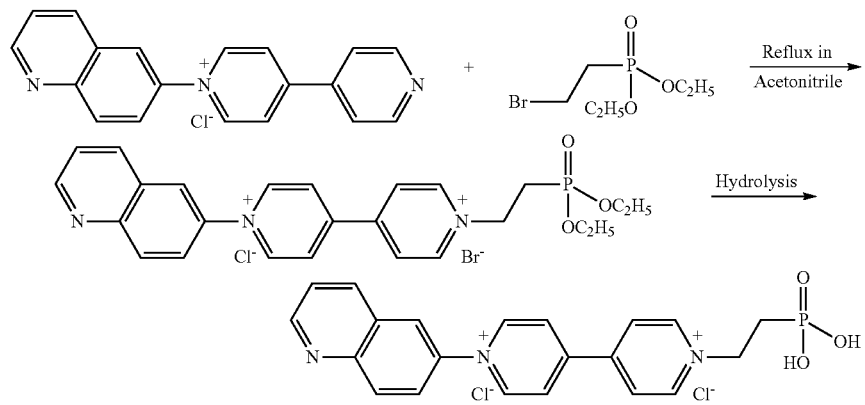

Figure 6A:
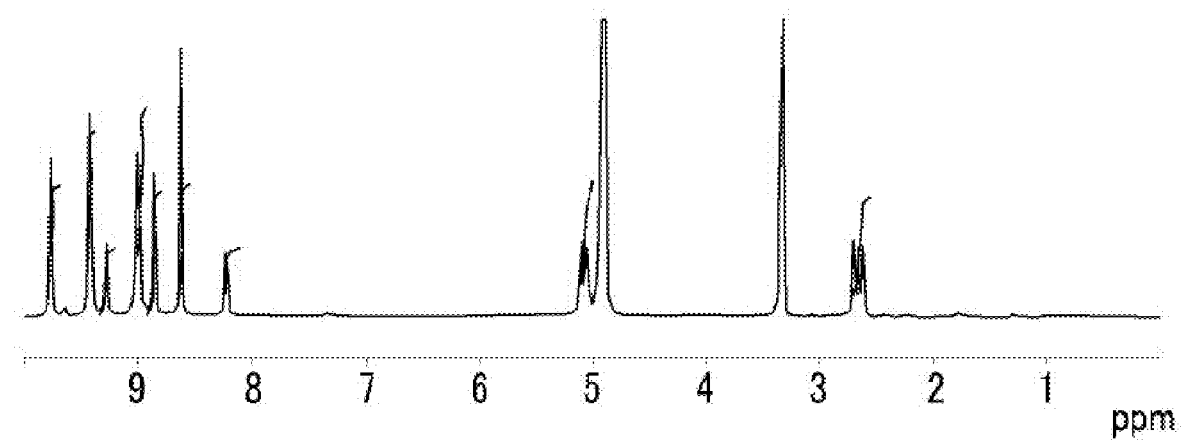
FIG. 6A is a $^1$H NMR spectrum of the electrochromic material according to Example 6.

The structure of the compound represented by chemical formula 1F is identified by its $^1$H NMR spectrum (Refer to FIG. 6A).

The chemical shift is measured in $CD_3OD$ solution and is referenced to TMS. $^1$H-NMR ($CD_3OD$/TMS) δ (ppm): 9.76 (2H, d, pyridine proton), 9.49-9.39 (3H, m, includes pyridine proton), 9.29 (1H, d), 9.07-8.95 (3H, m, includes pyridine proton), 8.86 (2H, d), 8.62 (2H,$), 8.27-8.19 (1H, q), 5.16-5.01 (2H, quintet, methylene proton of phosphonic acid group), 2.74-2.58 (2H, quintet, methylene proton of phosphonic acid group).

Fabrication of Electrochromic Device and Electrochromic Characteristic Identification An electrochromic device is fabricated according to the same method as in Example 1, except that the electrochromic material according to Example 6 is used. A voltage of 0V to 2.2V is applied to the electrochromic device, and the following electrochromic characteristics are observed.

The electrochromic device according to Example 6 has an operating voltage of about 0.8V, a potential window displaying light green from about 0.8 to about 1.5V, and a potential window displaying dark green from about 1.8 to about 2.2V.

Figure 6B:
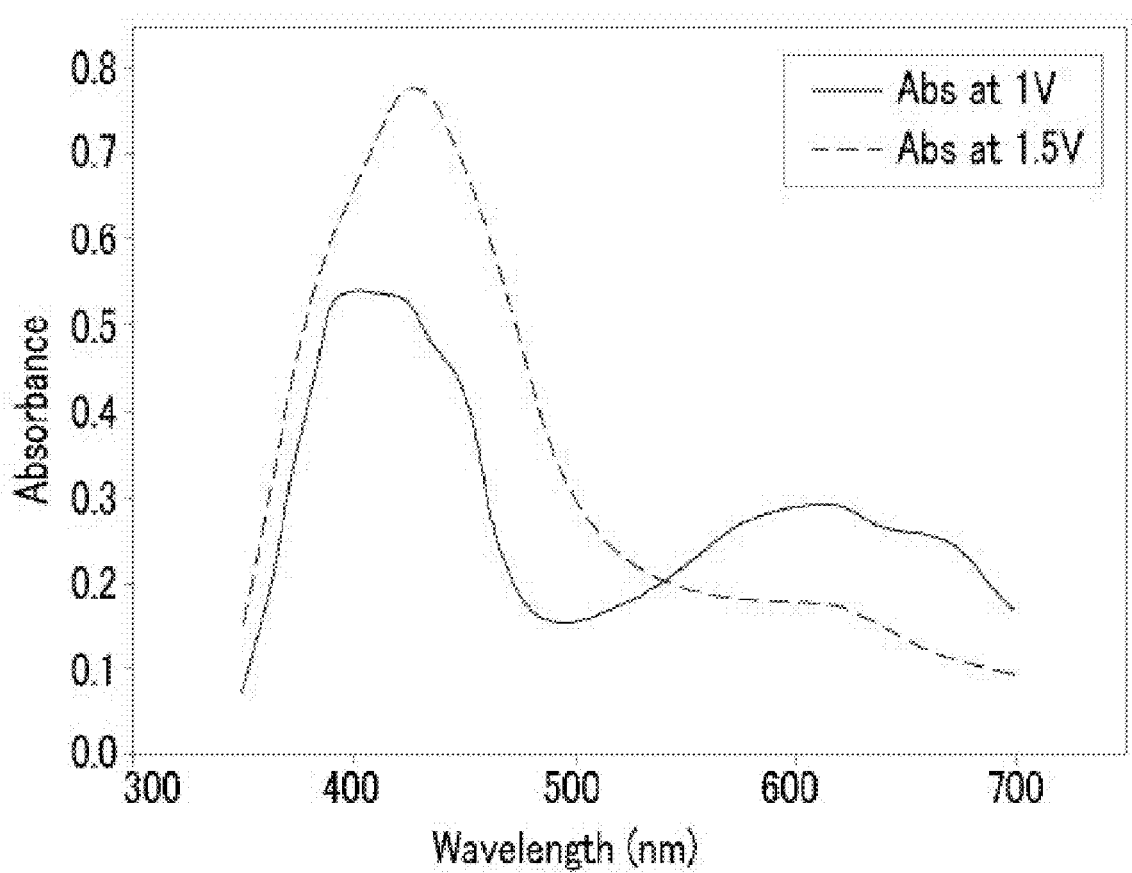
FIG. 6B is a plot of absorbance versus wavelength (nm) for the electrochromic material of Example 6 at voltages of about 1V and about 1.5V.
Figure 6C:
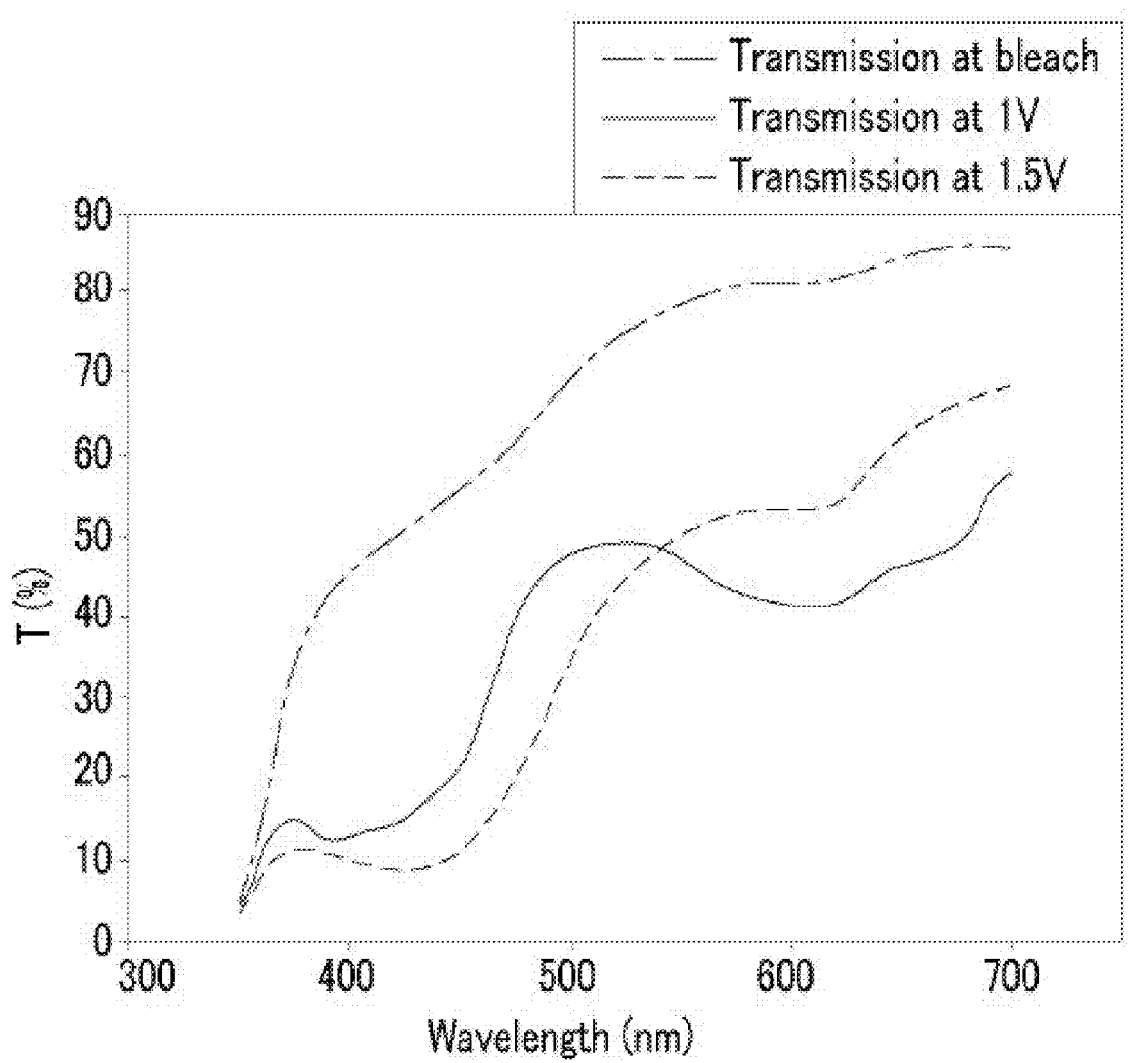
FIG. 6C is a plot of transmittance versus wavelength (nm) of the electrochromic material of Example 6 at voltages of 0V, about 1 V, and about 1.5V.

FIG. 6B is a plot of absorbance versus wavelength of the electrochromic material of Example 6 at about 1V and about 1.5V, and FIG. 6C is a plot of transmittance versus wavelength (in nm) of the electrochromic material of Example 6 at about 0V, about 1V, and about 1.5V.

Referring to FIGS. 6B and 6C, the absorption/transmission wavelength at about 1V and the absorption/transmission wavelength at about 1.5V are seen to be different. At about 1V, the light green wavelength region (about 480-500 nm) has low absorbance and high transmittance (FIG. 6B), while on the contrary, at about 1.5V, the dark green wavelength region (about 550-580 nm) has low absorbance and high transmittance (FIG. 6C).

EXAMPLE 7

Synthesis of Chemical Formula 1G Compound

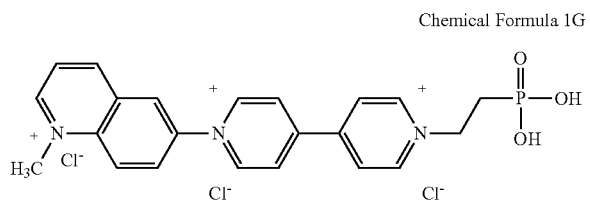

Chemical Formula 1G 1 mmol (0.535 g) of the ethyl ester of the compound of Chemical Formula 1F and 15 mmol (2.115 g) of methyl iodide are added to 200 ml of a 1:1 mixture of tetrahydrofuran and methanol, and then the resultant is heated to 75° C. for five days. Subsequently, the yellow residue is collected by filtration and resultant is dissolved in a minimum quantity of methanol. Then, acetone is added thereto until a compound is precipitated. The precipitate is collected by filtration, rinsed with acetone several times, and dried. The yield is about 60%.

The obtained compound is hydrolyzed in 50 ml of 37% (w/w) concentrated aqueous hydrochloric acid and then the solvent is removed. Acetone is added to the resultant yellow solid followed by collection of the solid by filtration and dissolving it in a minimum amount of methanol. Next, acetone is added to the solution for reprecipitation, and it is then collected by filtration and dried, to provide a compound represented by Chemical Formula 1G. The yield is about 75%.

Reaction scheme 1G

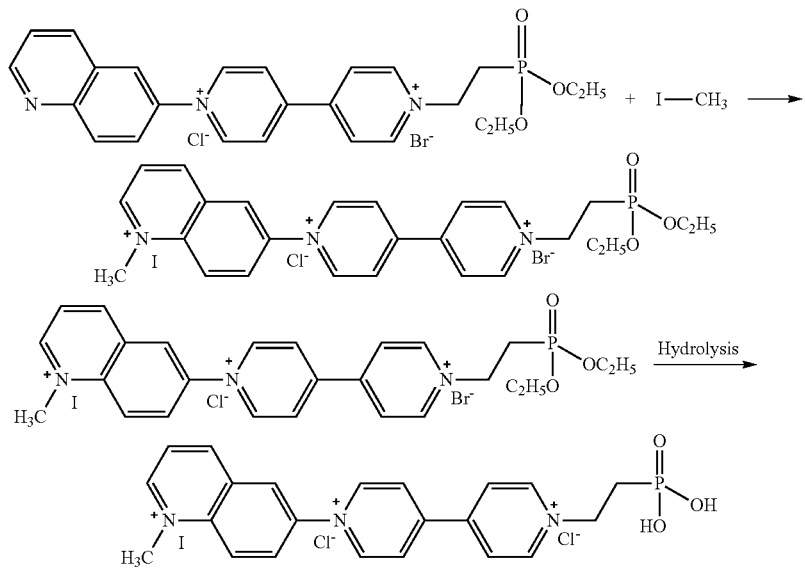

Figure 7:
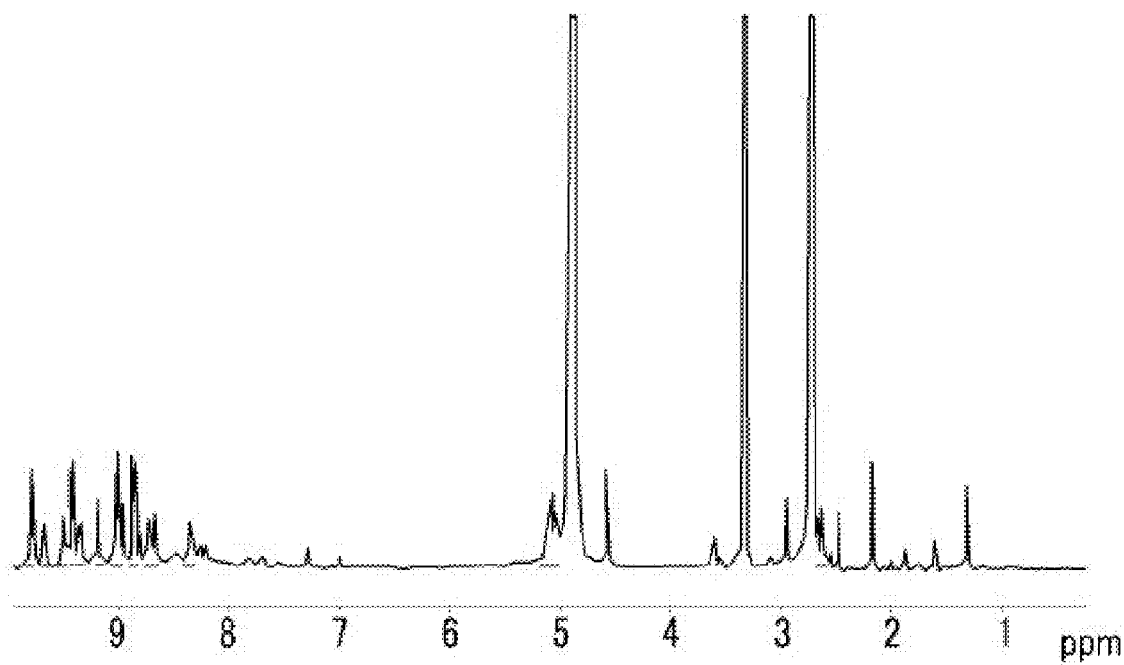
FIG. 7 is a $^1$H NMR spectrum of the electrochromic material according to Example 7.

The structure of the compound represented by chemical formula 1G is identified by its $^1$H NMR spectrum (Refer to FIG. 7).

The chemical shift is measured in $CD_3OD$ solution and is referenced to TMS. $^1$H-NMR ($CD_3OD$/TMS) δ (ppm): 9.76 (2H, d, pyridine proton), 9.47-9.32 (3H, m, includes pyridine proton), 9.29 (1H, d), 9.02-8.92 (3H, m, includes pyridine proton), 8.84 (2H, d, pyridine proton), 8.59 (2H,$), 8.21-8.05 (1H, q), 6.20-6.23 (3H, quintet $CH_3$ proton) 5.13-4.96 (2H, quintet, methylene proton of phosphonic acid group), 2.73-2.51 (2H, quintet, methylene proton of phosphonic acid group).

Fabrication of Electrochromic Device and Electrochromic Characteristic Identification An electrochromic device is fabricated according to the same method as in Example 1, except that the electrochromic material according to Example 7 is used. A voltage of 0V to 2.2V is applied to the electrochromic device, and the following electrochromic characteristics are observed.

The electrochromic device according to Example 7 has an operating voltage of about 0.8V, a potential window displaying light green from about 0.8 to about 1.5V, and a potential window displaying dark green from about 1.8 to about 2.2 V.

EXAMPLE 8

Synthesis of Chemical Formula 1H

Chemical Formula 1H

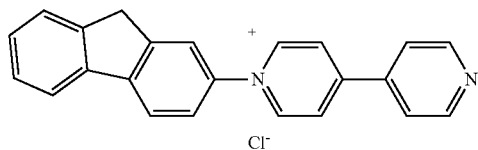

1 mmol (0.181 g) of 2-aminofluorene and 1 mmol (0.560 g) of 4,4-bis-(2,4-dinitrophenyl)-4,4-dipyridyl dichloride are dissolved in 100 ml of ethanol. The mixture is heated at reflux for 2 days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven, to provide the compound of Chemical Formula 1H. The yield is about 60%.

Reaction Scheme 1H

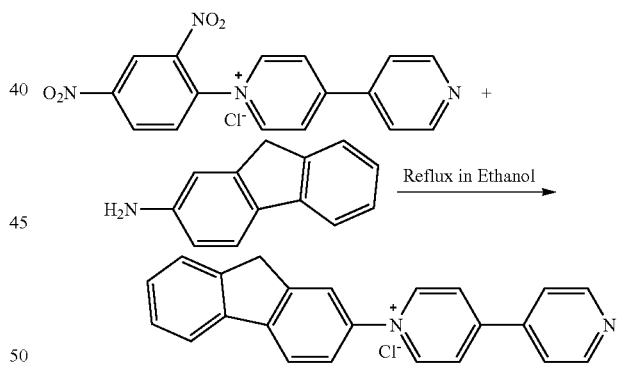

Figure 8:
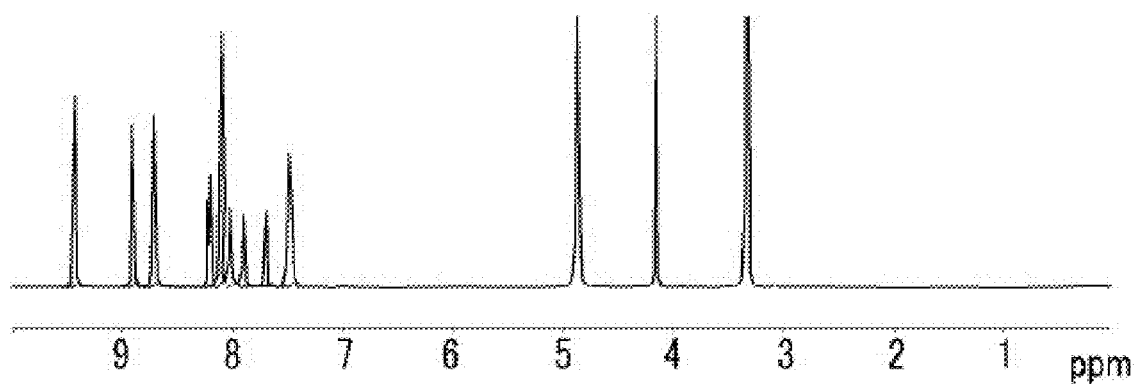
FIG. 8 is a $^1$H NMR spectrum of the electrochromic material according to Example 8.

The structure of the compound represented by chemical formula 1H is identified by its $^1$H NMR spectrum (Refer to FIG. 8).

The chemical shift is measured in $CD_3OD$ solution and is referenced to TMS. $^1$H-NMR ($CD_3OD$/TMS) δ (ppm): 9.43 (2H, d, pyridine proton), 8.91 (2H, d, pyridine proton), 8.70 (2H, d, pyridine proton), 8.22 (1H, d), 8.11 (3H, d, includes pyridine proton), 8.02 (1H, d), 7.89 (1H, d), 7.7 (1H, d), 7.48 (2H, quintet), 4.15 (2H, s).

Fabrication of Electrochromic Device and Electrochromic Characteristic Identification An electrochromic device is fabricated according to the same method as in Example 1, except that the electrochromic material according to Example 8 is used. A voltage of 0V to 2.2V is applied to the electrochromic device, and the following electrochromic characteristics are observed.

The electrochromic device according to Example 8 has an operating voltage of about 0.8V, a potential window displaying green from about 0.8 to about 1.1V, and a potential window displaying red from about 1.3 to about 2.0V.

EXAMPLE 9

Synthesis of Chemical Formula 1I Compound

Chemical Formula 1I

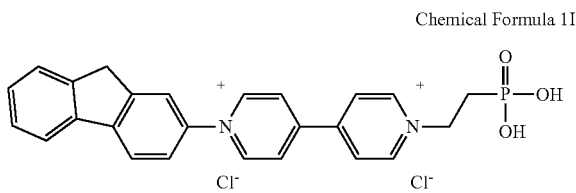

1 mmol (0.356 g) of the Chemical Formula 1H compound and 15 mmol (3.225 g) of 1-bromoethyl phosphonate are dissolved in a mixed solvent of acetonitrile and dimethylsulfoxide. The mixture is heated at reflux for 5 days. Subsequently, the yellow residue is collected by filtration and resultant is dissolved in a minimum amount of methanol. Then, acetone is added thereto until a compound is precipitated. The precipitate is collected by filtration, rinsed with acetone several times, and dried. The yield is about 50%.

The thus-obtained compound is hydrolyzed in 50 ml of 37% (w/w) concentrated aqueous hydrochloric acid and then the solvent is removed. Acetone is added to the resultant yellow solid followed by collection of the solid by filtration and dissolving it in a minimum amount of methanol. Next, acetone is added to the solution for reprecipitation, and it is then collected by filtration and dried, to provide a compound represented by Chemical Formula 1I. The yield is about 80%.

Figure 9A:
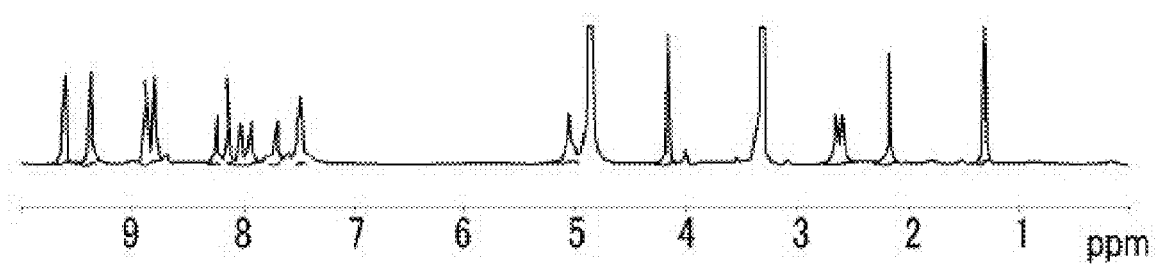
FIGS. 9A, 9B, and 9C are respectively a $^1$H NMR spectrum, a photograph showing the color within a first voltage range, and a photograph showing the color within a second voltage range for the electrochromic material according to Example 9.

The structure of the compound represented by chemical formula 1I is identified by its $^1$H NMR spectrum (Refer to FIG. 9A).

The chemical shift is measured in $CD_3OD$ solution and is referenced to TMS. $^1$H-NMR ($CD_3OD$/TMS) δ (ppm): 9.61 (2H, d, pyridine proton), 9.38 (2H, d, pyridine proton), 8.87 (2H, d, pyridine proton), 8.80 (2H, d, pyridine proton), 8.23 (1H, d), 8.13 (2H,$), 8.03 (1H, d), 7.93 (1H, d), 7.7 (1H, d), 7.49 (2H, t), 5.14-4.96 (2H, quintet, methylene proton of phosphonic acid group), 4.16 (2H, s), 2.75-2.20 (2H, quintet, methylene proton of phosphonic acid group).

Fabrication of Electrochromic Device and Electrochromic Characteristic Identification An electrochromic device is fabricated according to the same method as in Example 1, except that the electrochromic material according to Example 9 is used. A voltage of 0V to 2.2V is applied to the electrochromic device, and the following electrochromic characteristics are observed.

Figure 9B:
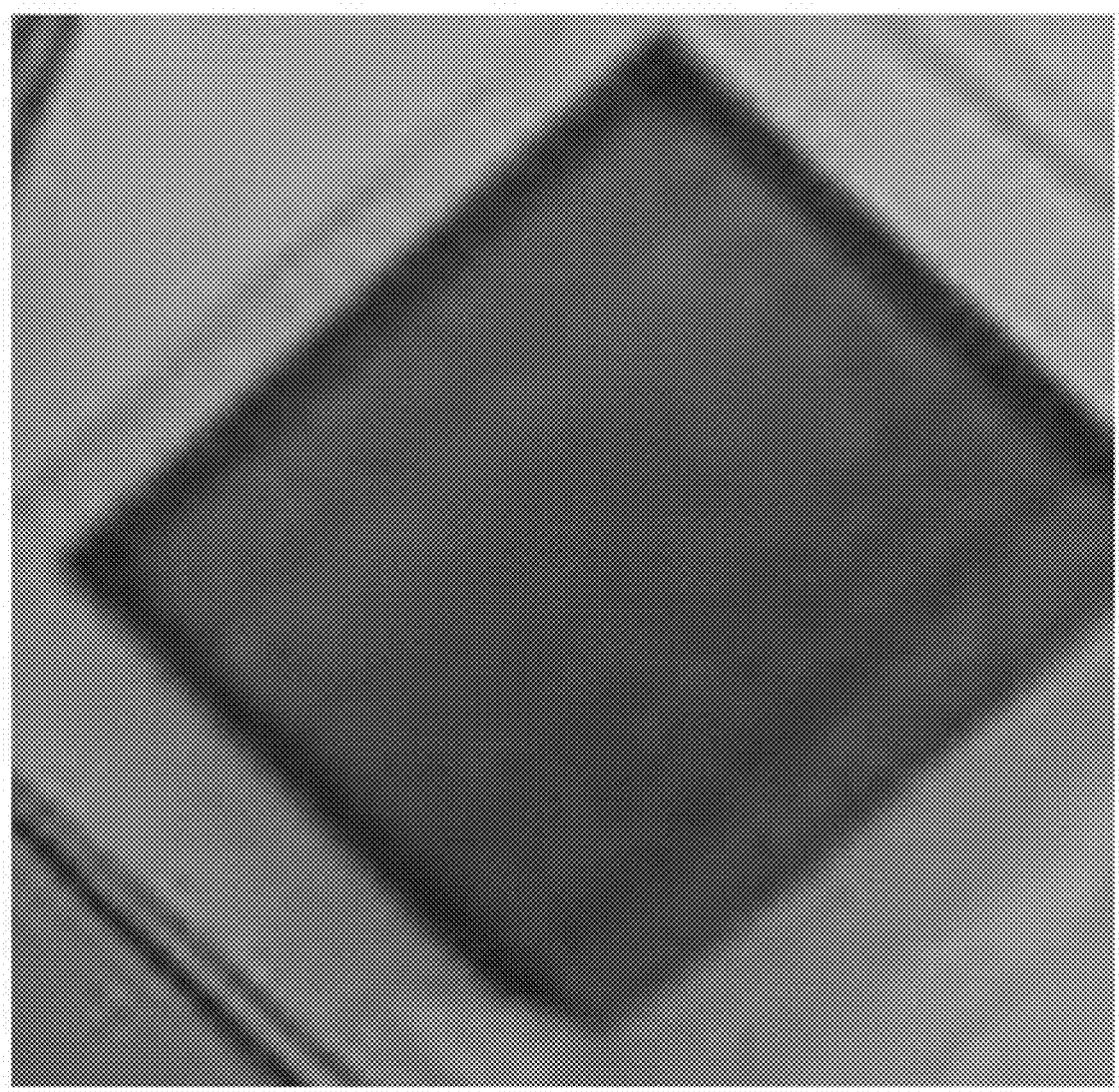
Figure 9C:
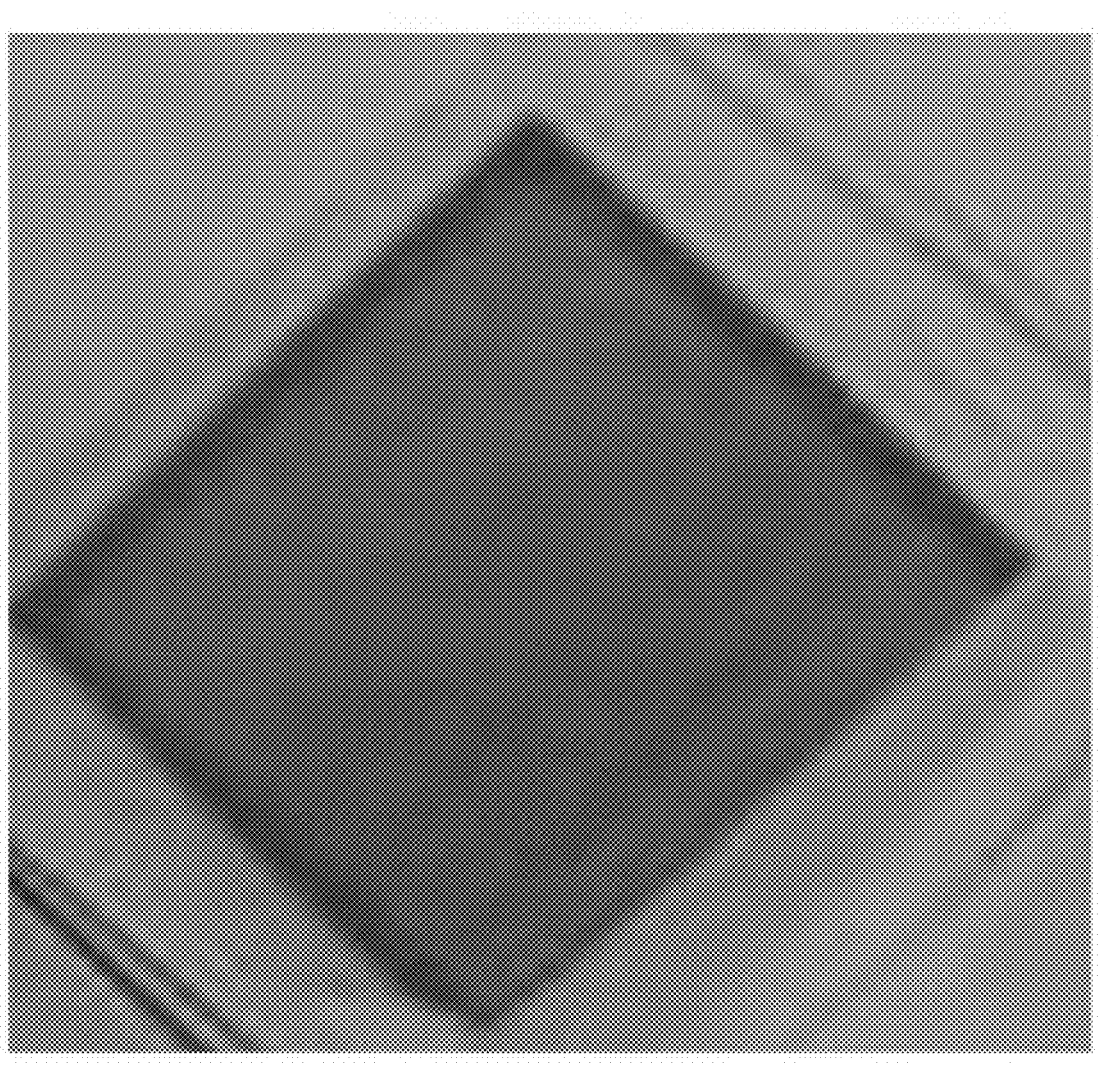

Referring to FIGS. 9B and 9C, the electrochromic device according to Example 9 has an operating voltage of about 0.8V, a potential window displaying green from about 0.8 to about 1.1V (FIG. 9B), and a potential window displaying red from about 1.5 to about 1.8V (FIG. 9C).

EXAMPLE 10

Synthesis of Chemical Formula 1J Compound

Chemical Formula 1J

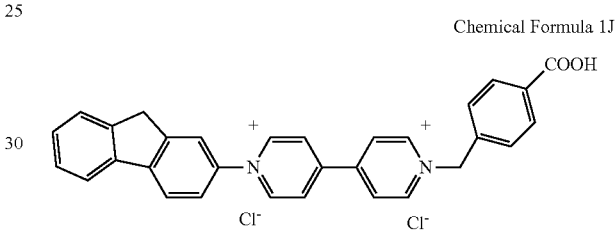

1 mmol (0.356 g) of the Chemical Formula 1H compound and 1 mmol (2.9 g) of 4-bromomethylbenzonitrile are dissolved in 200 ml of a 1:1 mixture of acetonitrile and dimethylsulfoxide. The mixture is heated at reflux for five days. Subsequently, a yellow residue is collected by filtration and the resultant is dissolved in a minimum amount of methanol. Then, acetone is added thereto until the nitrile compound is Reaction scheme 1I

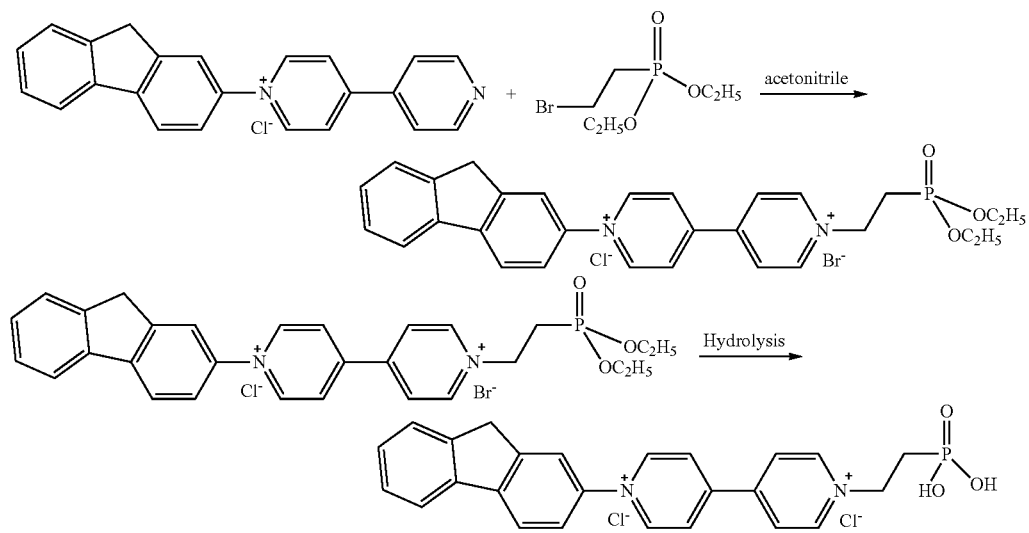

precipitated. The precipitate is collected by filtration, rinsed with acetone several times, and dried. The yield is about 60%.

The obtained compound is hydrolyzed in 50 ml of 37% (w/w) concentrated aqueous hydrochloric acid and then the solvent is removed. Acetone is added to the resultant yellow solid followed by collection of the solid by filtration and dissolving it in a minimum amount of methanol. Next, acetone is added to the solution for reprecipitation, and the precipitate is then collected by filtration and dried, to provide a compound represented by Chemical Formula 1J.

The yield is about 80%.

(4H, dd, pyridine proton), 8.80 (2H, d), 8.23 (1H, d), 8.14 (1H, d), 8.03 (1H, d), 7.90-7.86 (3H, m), 7.78 (2H, d), 7.71 (1H, d), 7.49 (2H, t). 6.13 (2H, s, methylene proton), 4.16 (2H, s).

Fabrication of Electrochromic Device and Electrochromic Characteristic Identification An electrochromic device is fabricated according to the same method as in Example 1, except that the electrochromic material according to Example 10 is used. A voltage of 0V to 2.2V is applied to the electrochromic device, and the following electrochromic characteristics are observed.

Reaction scheme 1J

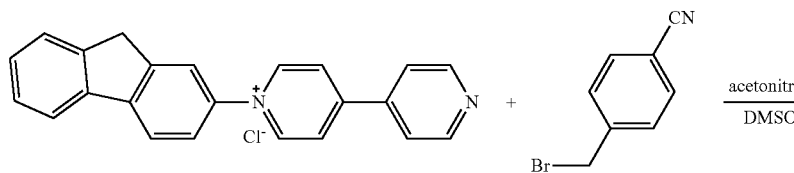

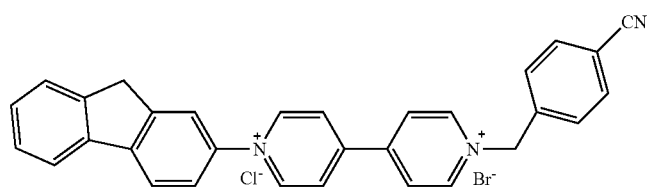

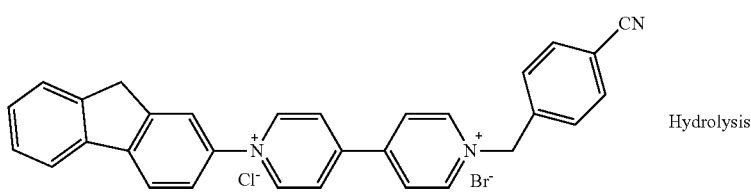

Hydrolysis

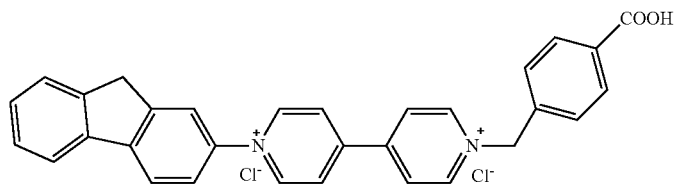

Figure 10A:
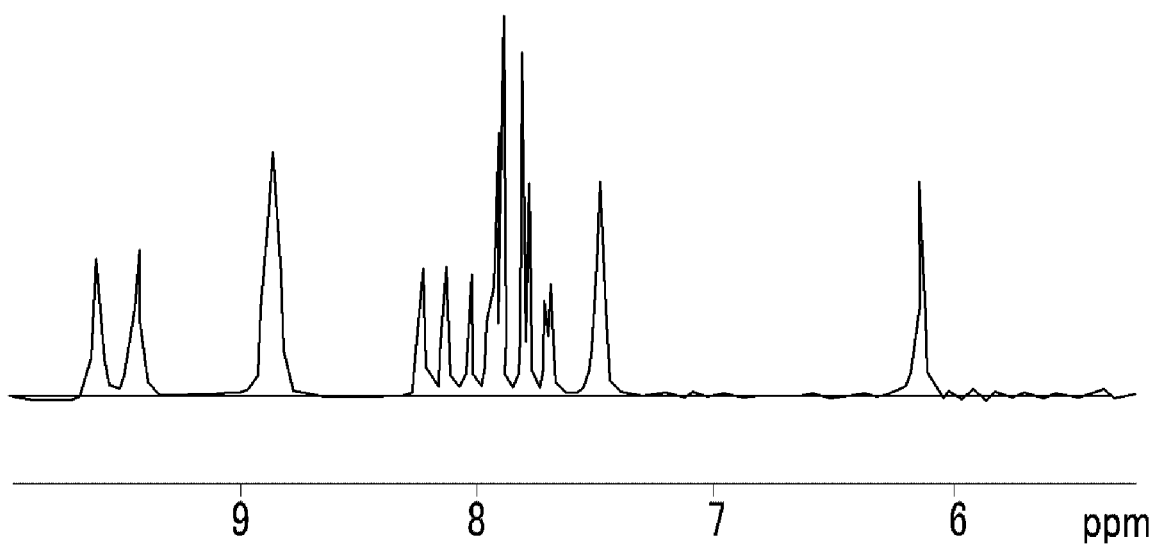
FIGS. 10A, 10B, and 10C are respectively a $^1$H NMR spectrum, a photograph showing the color within a first voltage range, and a photograph showing the color within a second voltage range for the electrochromic material according to Example 10.

The structure of the compound represented by chemical formula 1J is identified by its $^1$H NMR spectrum (Refer to FIG. 10A).

The chemical shift is measured in $CD_3OD$ solution and is referenced to TMS. $^1$H-NMR ($CD_3OD$/TMS) δ (ppm): 9.60 (2H, d, pyridine proton), 9.43 (2H, d, pyridine proton), 8.86

Figure 10B:
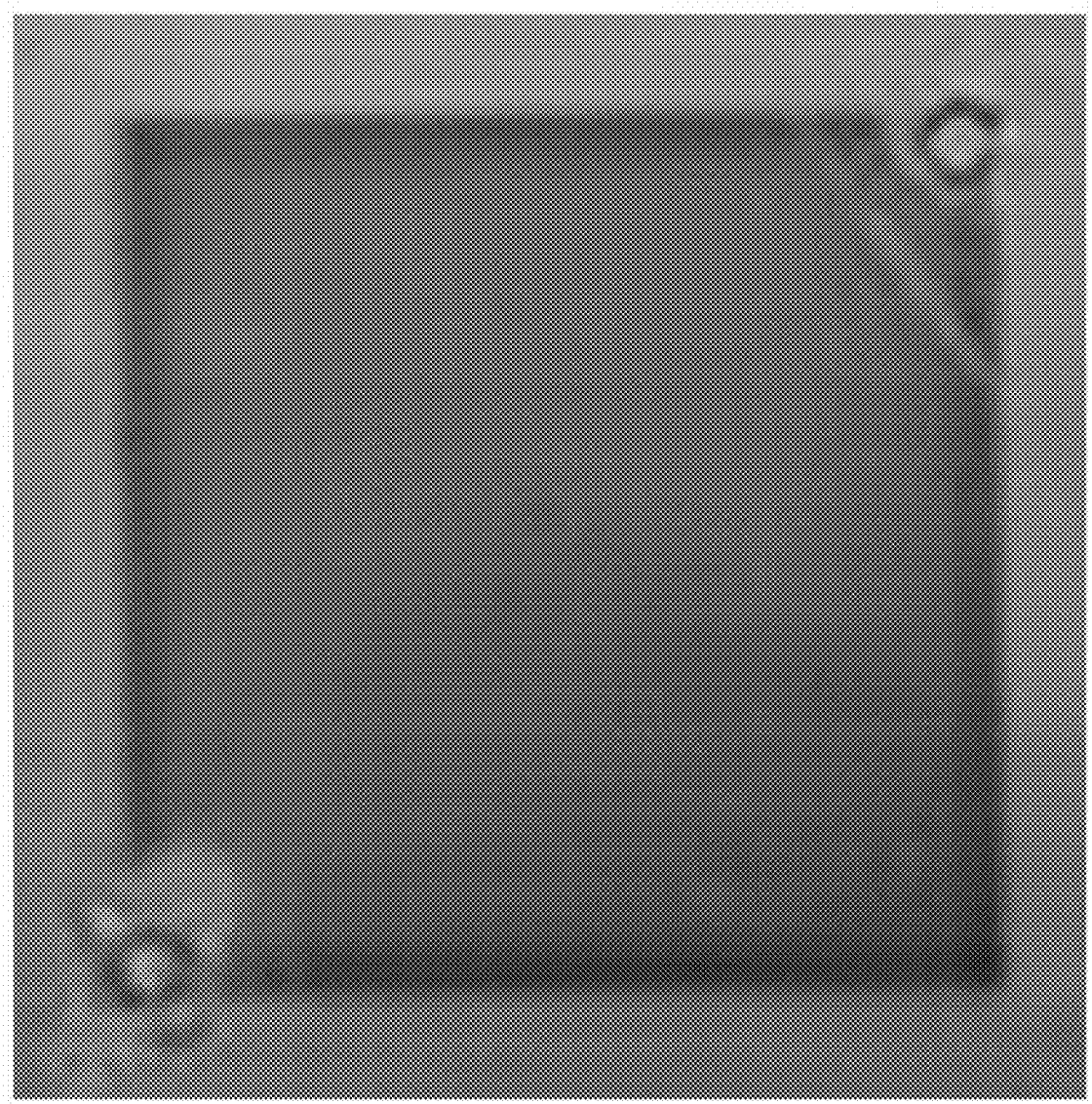
Figure 10C:
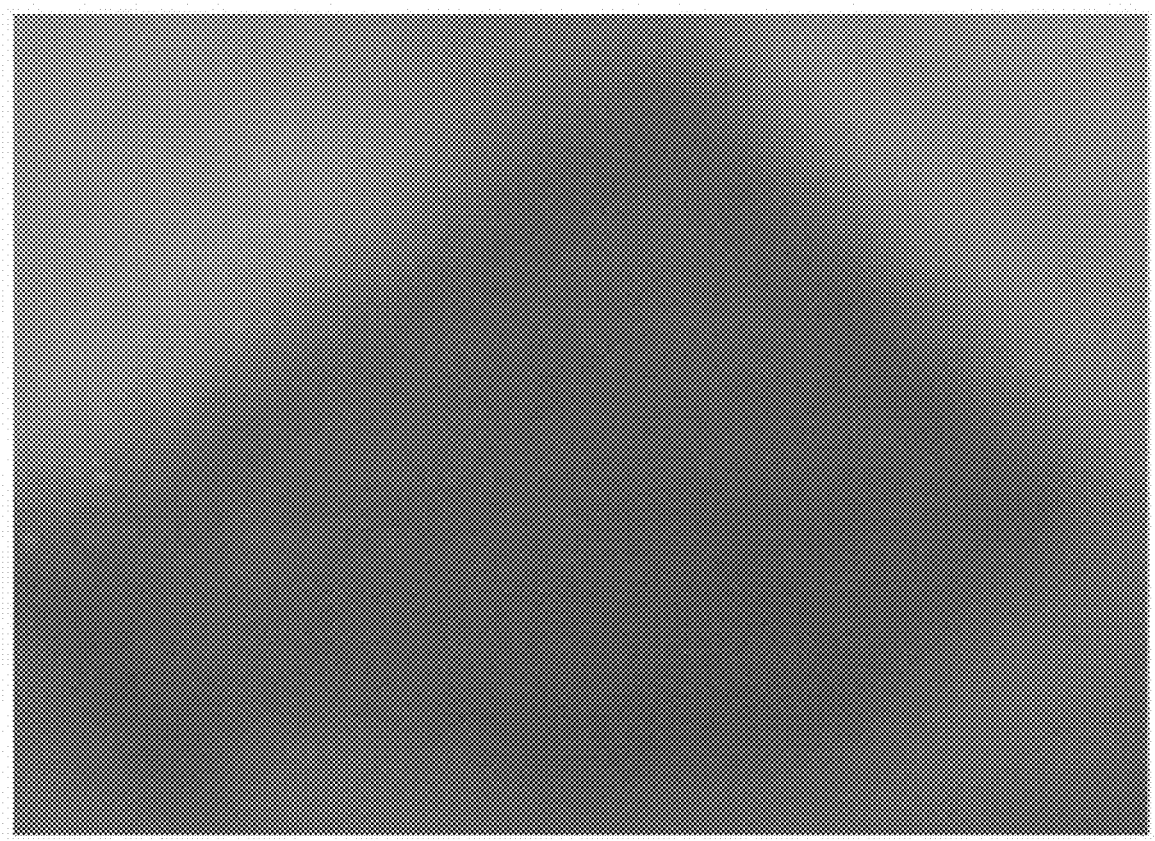

Referring to FIGS. 10B and 10C, the electrochromic device according to Example 10 has an operating voltage of about 0.8V, a potential window displaying green from about 0.8 to about 1.3V (FIG. 10B), and a potential window displaying red from about 1.5 to about 2.0 V (FIG. 10C).

EXAMPLE 11

Synthesis of Chemical Formula 1K Compound

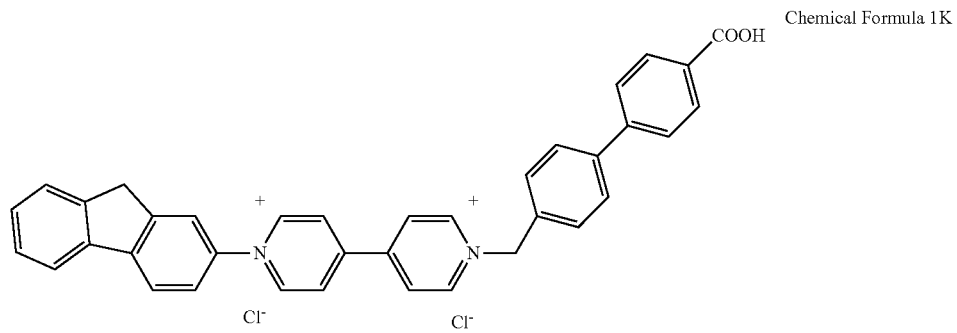

Chemical Formula 1K 1 mmol (0.356 g) of the Chemical Formula 1H compound and 15 mmol (2.9 g) of 4-bromomethyl-2-biphenylcarbonitrile are dissolved in 200 ml of a 1:1 mixture of acetonitrile and dimethylsulfoxide. The mixture is heated at reflux for 5 days. Subsequently, the yellow residue is collected by filtration and the resultant is dissolved in a minimum amount of methanol. Then, acetone is added thereto until a nitrile compound is precipitated. The precipitate is collected by filtration, rinsed with acetone several times, and dried. The yield is about 50%.

The obtained compound is hydrolyzed in 50 ml of 37% (w/w) concentrated aqueous hydrochloric acid and then the solvent is removed. Acetone is added to the resultant yellow solid followed by collection by filtration and dissolving it in a minimum amount of methanol. Next, acetone is added for reprecipitation, and it is then collected by filtration and dried, to provide a compound represented by Chemical Formula 1K. The yield is about 80%.

Reaction scheme 1K

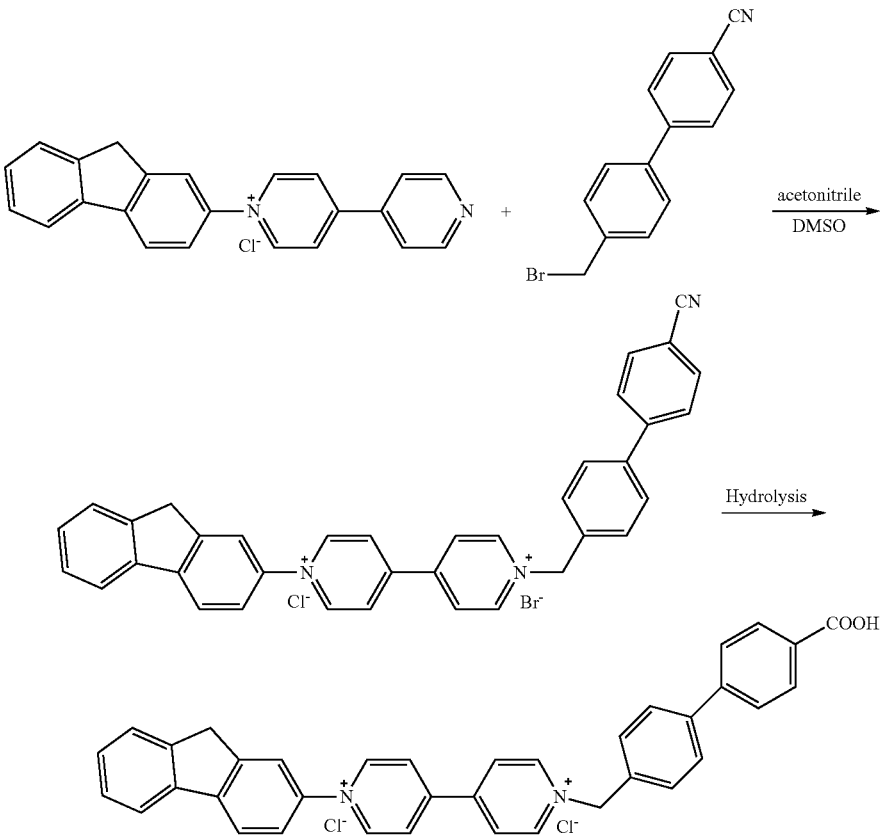

Figure 11A:
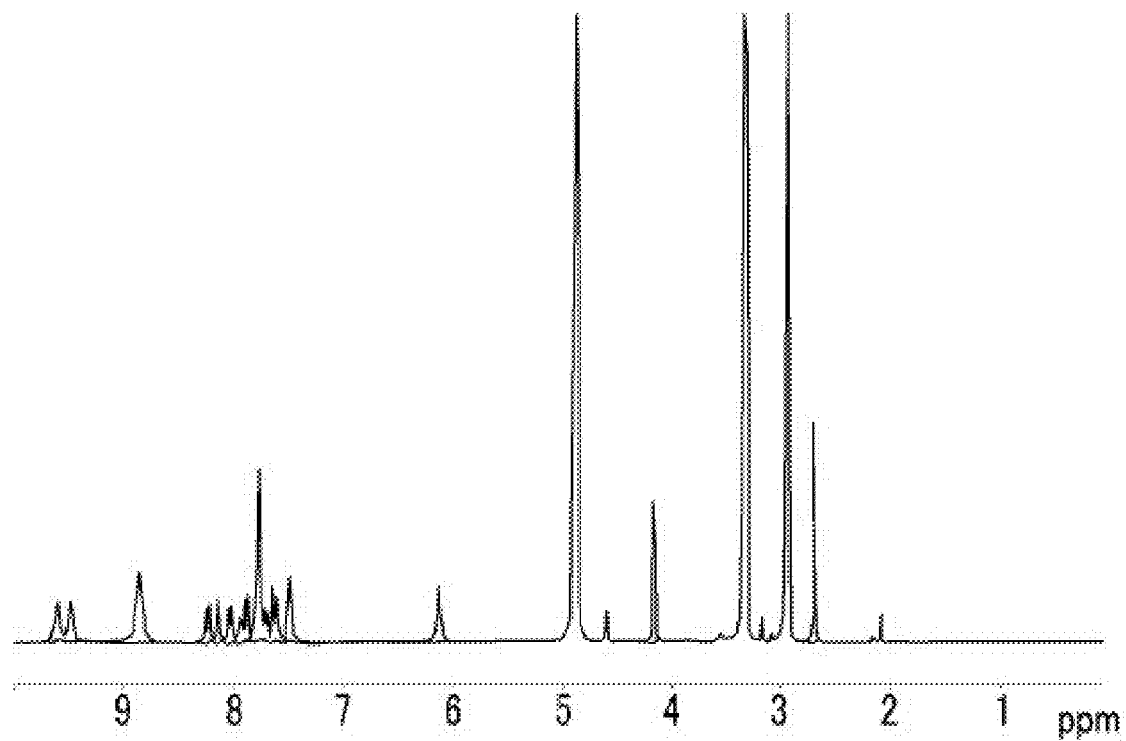
FIGS. 11A, 11B, and 11C are respectively a $^1$H NMR spectrum, a photograph showing the color within a first voltage range, and a photograph showing the color within a second voltage range for the electrochromic material according to Example 11.

The structure of the compound represented by chemical formula 1K is identified by its ¹H NMR spectrum (Refer to FIG. 11A).

The chemical shift is measured in DMSO solution and is referenced to TMS. ¹H-NMR (DMSO/TMS) δ (ppm): 9.60 (2H, d, pyridine proton), 9.48 (2H, d, pyridine proton), 8.86 (4H, dd, pyridine proton), 8.23 (1H, d), 8.14 (1H, d), 8.02 (1H, d), 7.93 (1H, d), 7.88 (2H, d), 7.84-7.66 (5H, m), 7.62 (2H, dd), 7.49 (2H, t). 6.12 (2H, s, methylene proton), 4.16 (2H, s).

Fabrication of Electrochromic Device and Electrochromic Characteristic Identification An electrochromic device is fabricated according to the same method as in Example 1, except that the electrochromic material according to Example 11 is used. A voltage of 0V to 2.2V is applied to the electrochromic device, and the following electrochromic characteristics are observed.

Figure 11B:
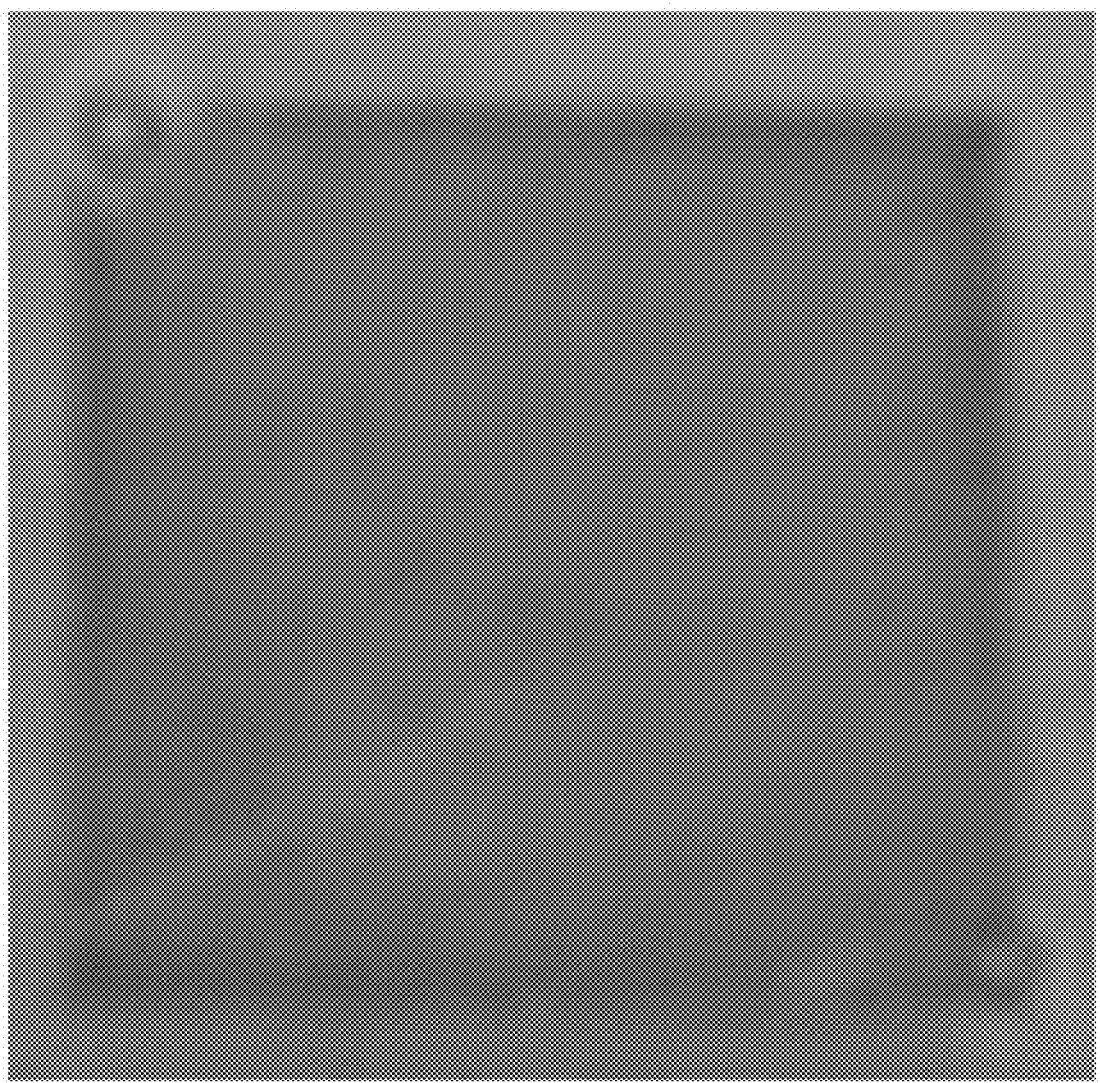
Figure 11C:

Referring to FIGS. 11B and 11C, the electrochromic device according to Example 11 has an operating voltage of about 0.8V, a potential window displaying green from about 0.8 to about 1.3V (FIG. 11B), and a potential window displaying red from about 1.5 to about 2.2V (FIG. 11C).

EXAMPLE 12

Synthesis of Chemical Formula 1L Compound

Chemical Formula 1L

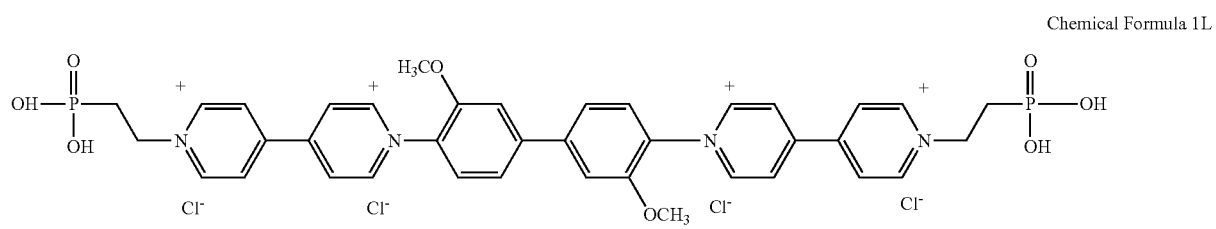

1 mmol (0.244 g) of o-dianisidine and 1 mmol (0.574 g) of 4-(2,4-dinitrophenyl)-4-diethyl ethyl phosphonate-4,4-dipyridyl chloride bromide are dissolved in 100 ml of ethanol. The mixture is heated at reflux for 2 days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven, to provide the compound of Chemical Formula 1 L. The yield is about 70%.

Reaction scheme 1L

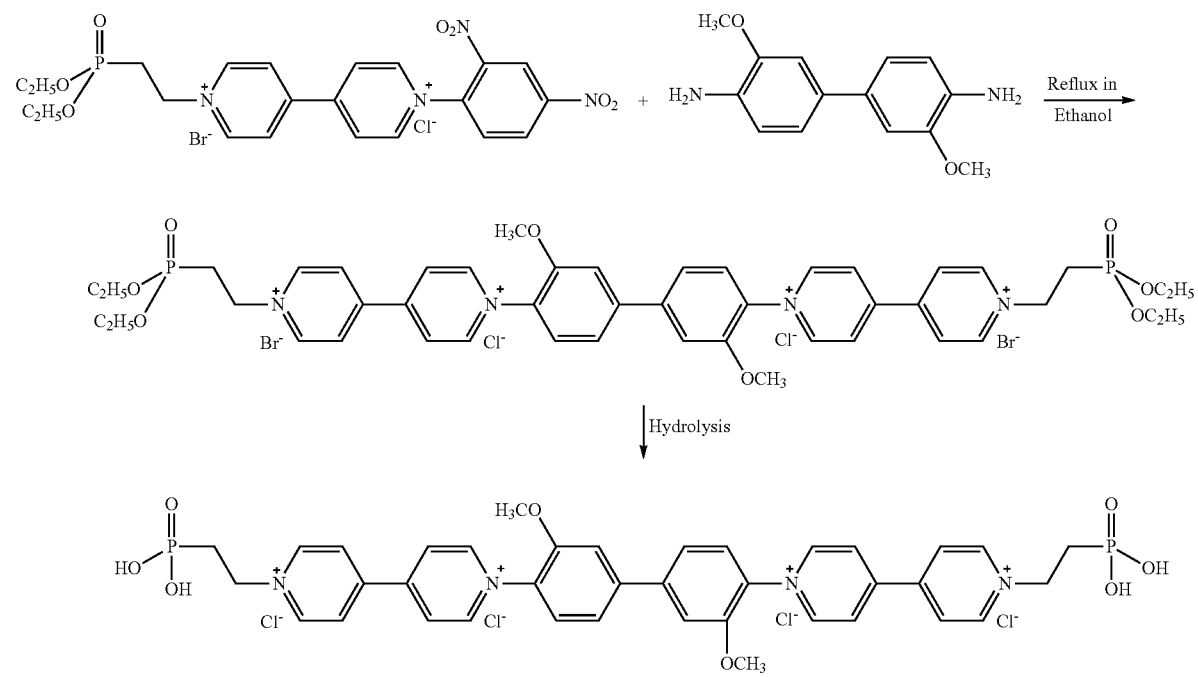

Figure 12A:
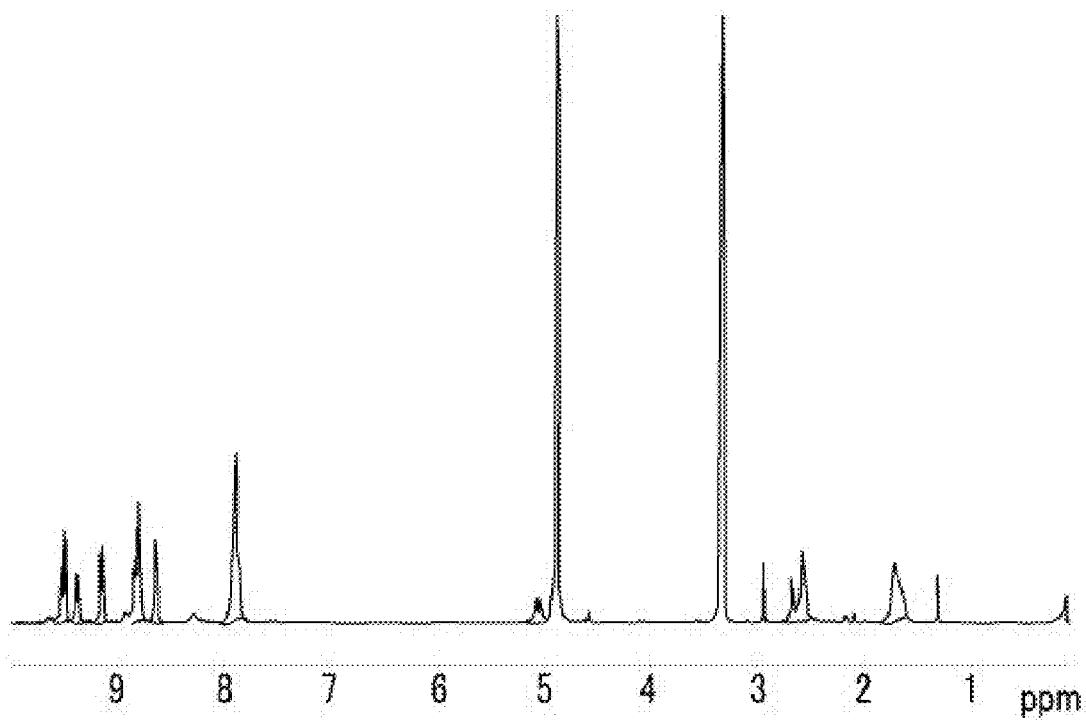
FIGS. 12A, 12B, and 12C are respectively a $^1$H NMR spectrum, a photograph showing the color within a first voltage range, and a photograph showing the color within a second voltage range for the electrochromic material according to Example 12.

The structure of the symmetric compound represented by chemical formula 1L is identified by its $^1$H NMR spectrum (Refer to FIG. 12A).

The chemical shift is measured in DMSO-d$_6$ solution and is referenced to TMS. $^1$H-NMR (DMSO-d$_6$/TMS) δ (ppm): 9.46 (2H, d, pyridine proton), 8.94 (2H, d, pyridine proton), 8.82 (2H, dd, pyridine proton), 8.18 (2H, d, pyridine proton), 7.99 (1H, d), 7.81 (2H, d).

Fabrication of Electrochromic Device and Electrochromic Characteristic Identification An electrochromic device is fabricated according to the same method as in Example 1, except that the electrochromic material according to Example 12 is used. A voltage of 0V to 2.2V is applied to the electrochromic device, and the following electrochromic characteristics are observed.

Figure 12B:
Figure 12C:
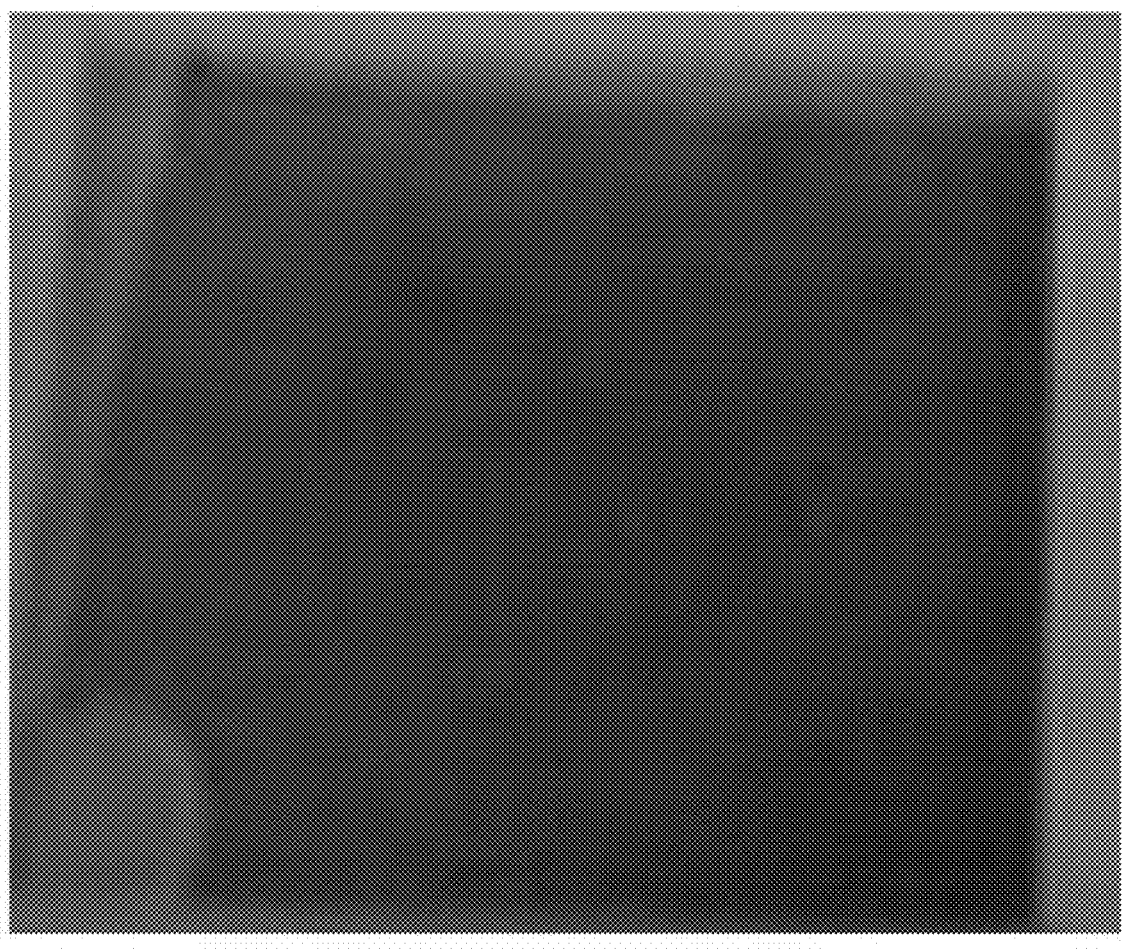

Referring to FIGS. 12B and 12C, the electrochromic device according to Example 12 has an operating voltage of about 0.8V, a potential window displaying green from about 0.8 to about 1.3V (FIG. 12B), and a potential window displaying red from about 1.4 to about 2.1V (FIG. 12C).

EXAMPLE 13

Synthesis of Chemical Formula 1M Compound

Chemical Formula 1M

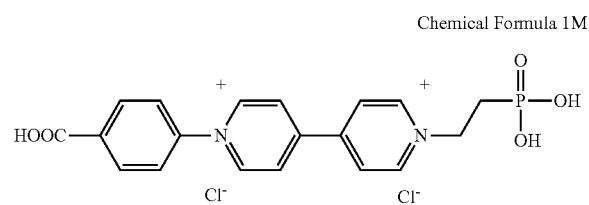

20 mmol (3.620 g) of 4-aminobenzonitrile and 1 mmol (0.574 g) of 4-(2,4-dinitrophenyl)-4-diethyl ethyl phosphonate-4,4-dipyridyl chloride bromide are dissolved in 100 ml of ethanol. The mixture is heated at reflux for two days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven, to provide the phosphonate compound. The yield is about 50%.

The obtained compound is hydrolyzed in 50ml of 37% (w/w) concentrated aqueous hydrochloric acid and then the solvent is removed. Acetone is added to the resultant yellow solid followed by collection by filtration and dissolving it in methanol. Next, acetone is added to the solution for reprecipitation, and it is then collected by filtration and dried, to provide a compound represented by Chemical Formula 1M. The yield is about 70%.

\Reaction scheme 1M

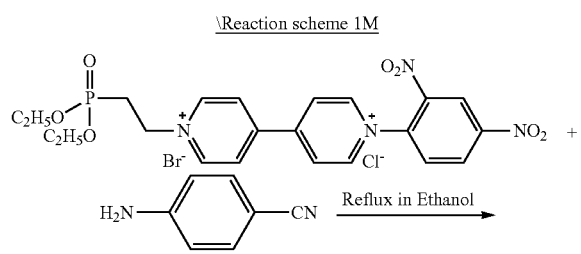

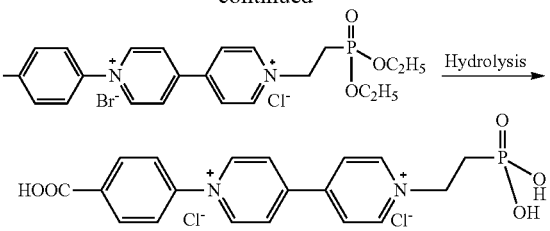

Figure 13A:
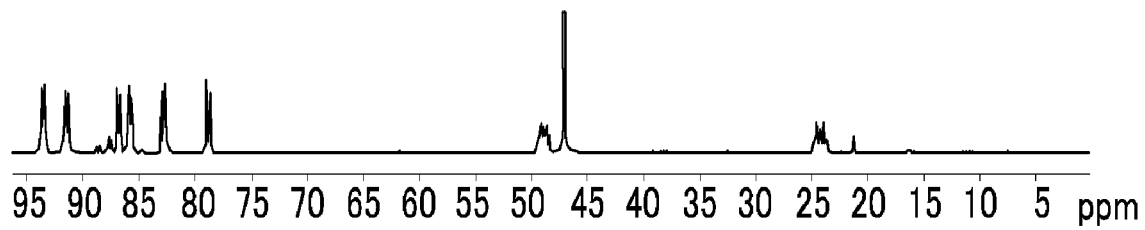
FIGS. 13A, 13B, and 13C are respectively a $^1$H NMR spectrum, a photograph showing the color within a first voltage range, and a photograph showing the color within a second voltage range for the electrochromic material according to Example 13.

The structure of the compound represented by chemical formula 1M is identified by its $^1$H NMR spectrum (Refer to FIG. 13A).

The chemical shift is measured in CD$_3$OD solution and is referenced to TMS. $^1$H-NMR (CD$_3$OD/TMS) δ (ppm): 9.36 (2H, d, pyridine proton), 9.15 (2H, d, pyridine proton), 8.69 (2H, dd, pyridine proton), 8.57 (2H, d, pyridine proton), 8.27 (1H, d), 7.88 (2H, d), 4.97-4.80 (2H, quintet methylene proton of phosphonic acid group), 2.5-2.34 (2H, quintet, methylene proton of phosphonic acid group).

Fabrication of Electrochromic Device and Electrochromic Characteristic Identification An electrochromic device is fabricated according to the same method as in Example 1, except that the electrochromic material according to Example 13 is used. A voltage of 0V to 2.2V is applied to the electrochromic device, and the following electrochromic characteristics are observed.

Figure 13B:
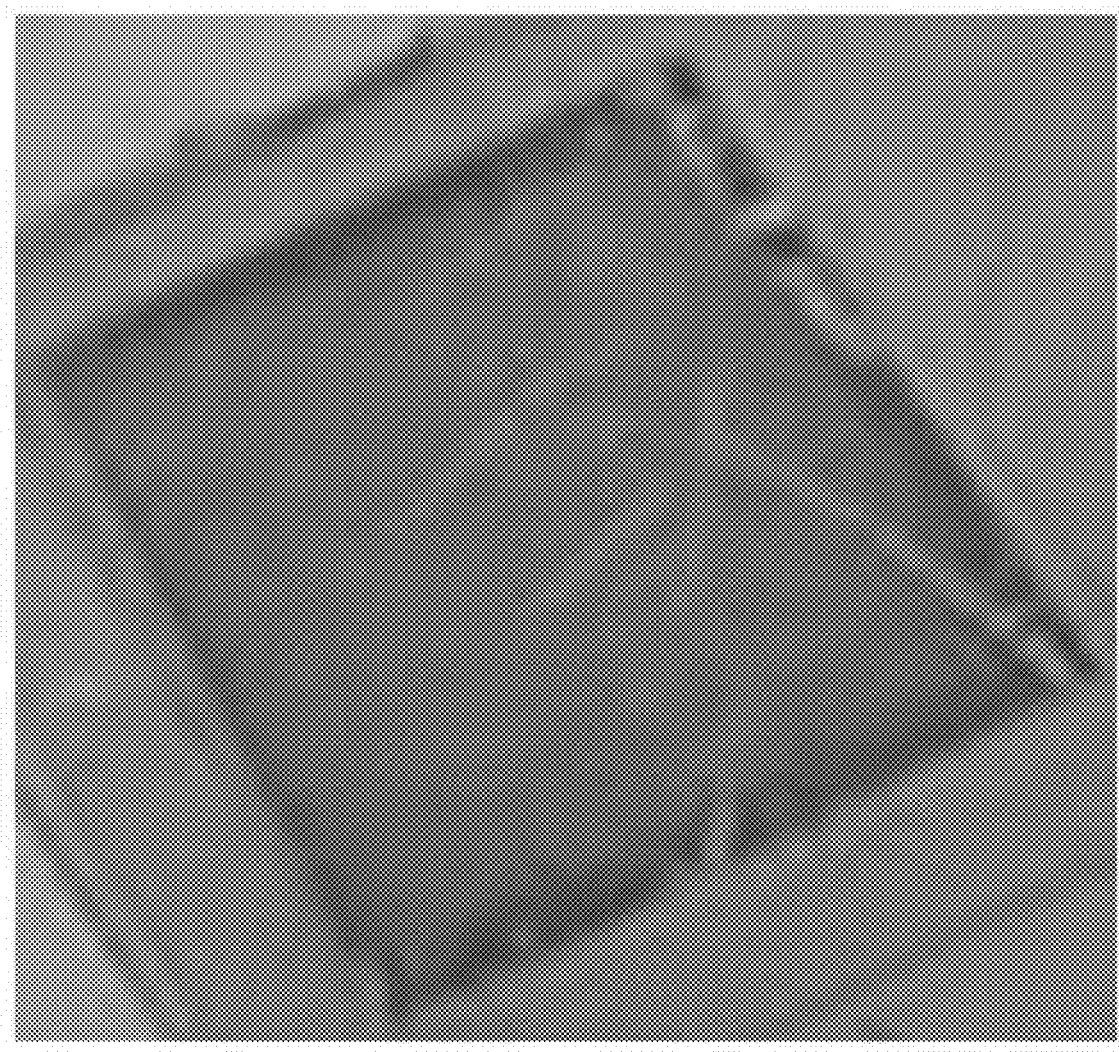
Figure 13C:
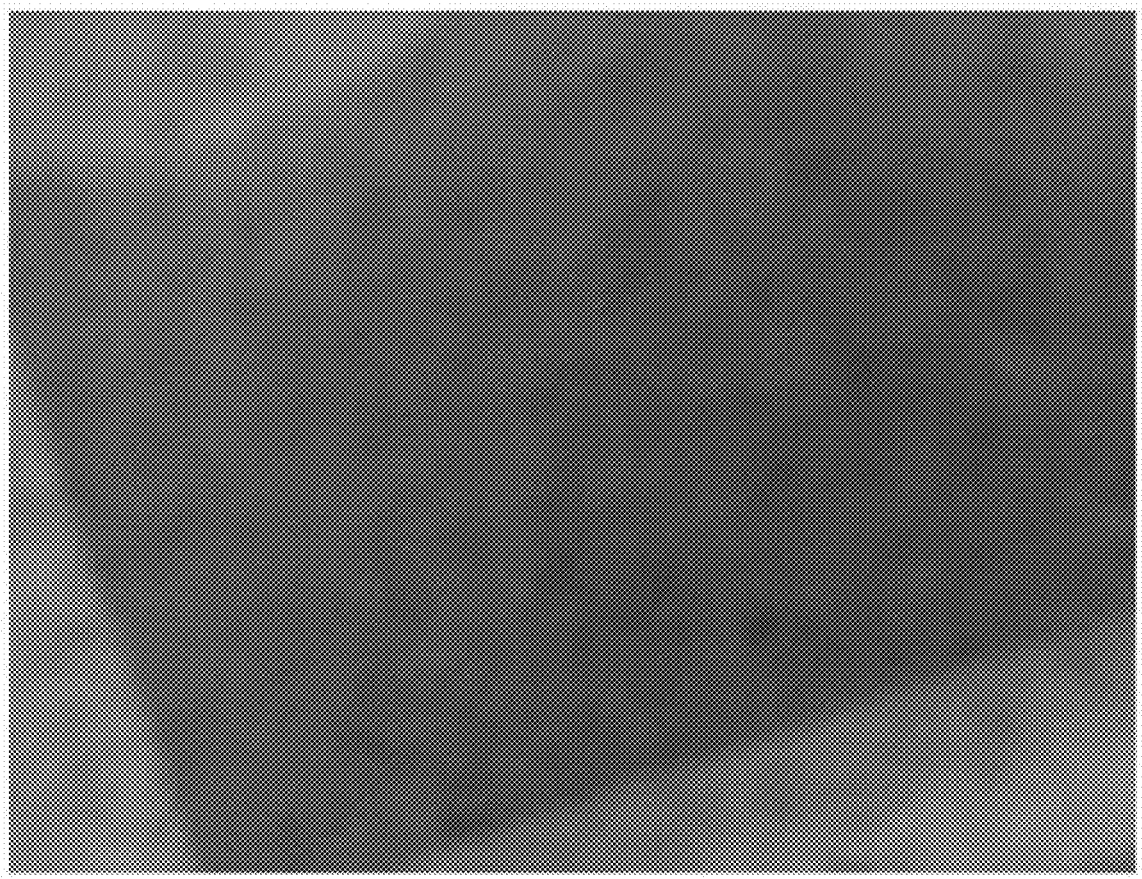

Referring to FIGS. 13B and 13C, the electrochromic device according to Example 13 has an operating voltage of about 0.8V, a potential window displaying green from about 0.8V to about 1.1V (FIG. 13B), and a potential window displaying red from about 1.3V to about 2.3V (FIG. 13C).

EXAMPLE 14

Synthesis of Chemical Formula 1N Compound

Chemical Formula 1N

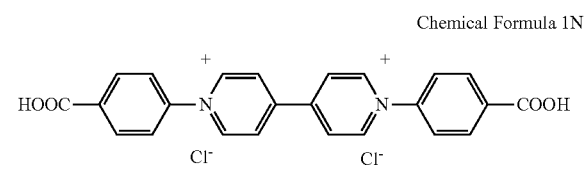

50 mmol (5.9 g) of 4-aminobenzonitrile and 1 mmol (0.560 g) of 4,4-bis-(2,4-dinitrophenyl)-4,4-pyridyl dichloride are dissolved in 100 ml of ethanol. The mixture is heated at reflux for 5 days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven. The yield is about 50%.

The obtained compound is hydrolyzed in 50 ml of 37% (w/w) concentrated aqueous hydrochloric acid and then the solvent is removed. Acetone is added to the resultant yellow solid followed by collection of the solid by filtration and dissolving it in a minimum amount of methanol. Next, acetone is added to the solution for reprecipitation, and it is then collected by filtration and dried, to provide a compound represented by Chemical Formula 1N. The yield is about 80%.

Reaction scheme 1N

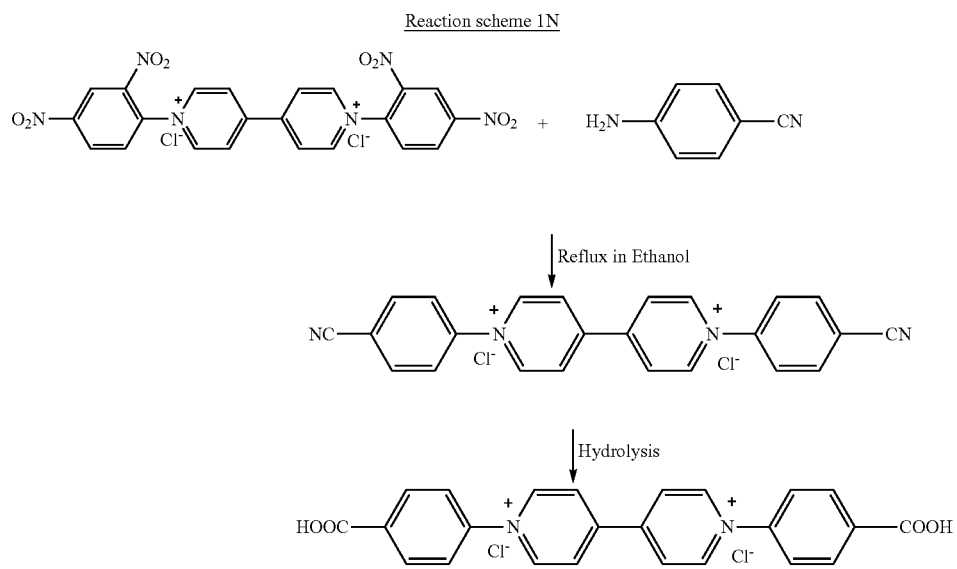

Figure 14A:
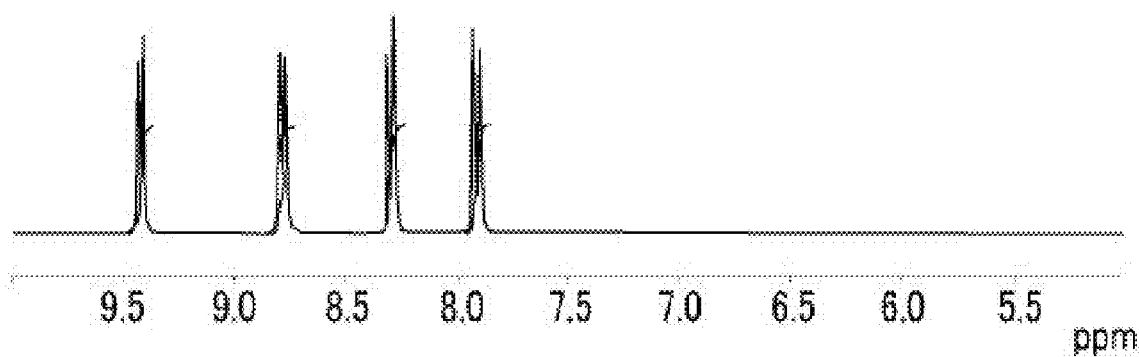
FIGS. 14A, 14B, and 14C are respectively a $^1$H NMR spectrum, a photograph showing the color within a first voltage range, and a photograph showing the color within a second voltage range for the electrochromic material according to Example 14.

The structure of the symmetric compound represented by chemical formula 1N is identified by its $^1$H NMR spectrum (Refer to FIG. 14A).

The chemical shift is measured in $CD_3OD$ solution and is referenced to TMS. $^1$H-NMR ($CD_3OD$/TMS) δ (ppm): 9.42 (2H, d, pyridine proton), 8.77 (2H, d, pyridine proton), 8.29 (2H, dd), 7.89 (2H, d).

Fabrication of Electrochromic Device and Electrochromic Characteristic Identification An electrochromic device is fabricated according to the same method as in Example 1, except that the electrochromic material according to Example 14 is used. A voltage of 0V to 2.2V is applied to the electrochromic device, and the following electrochromic characteristics are observed.

Figure 14B:
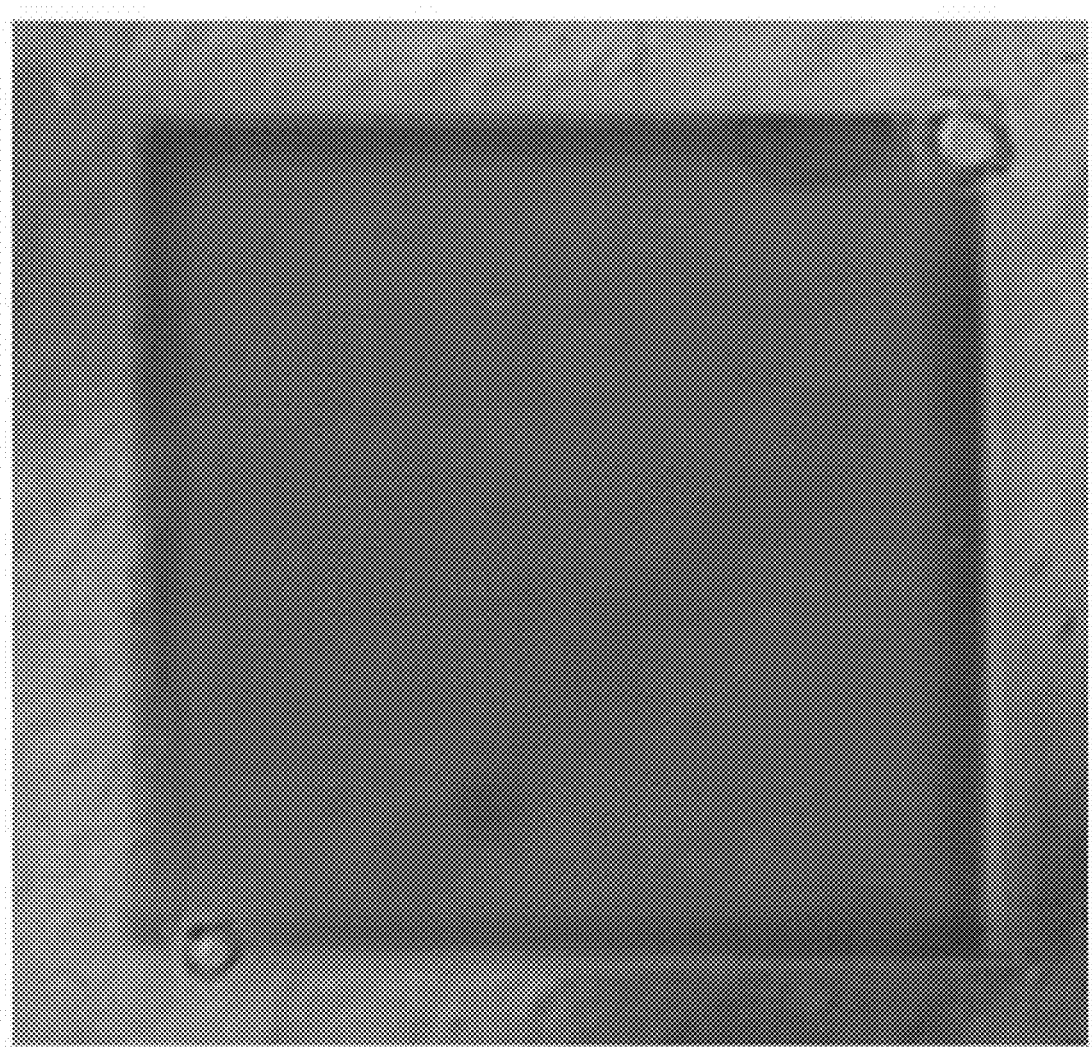
Figure 14C:
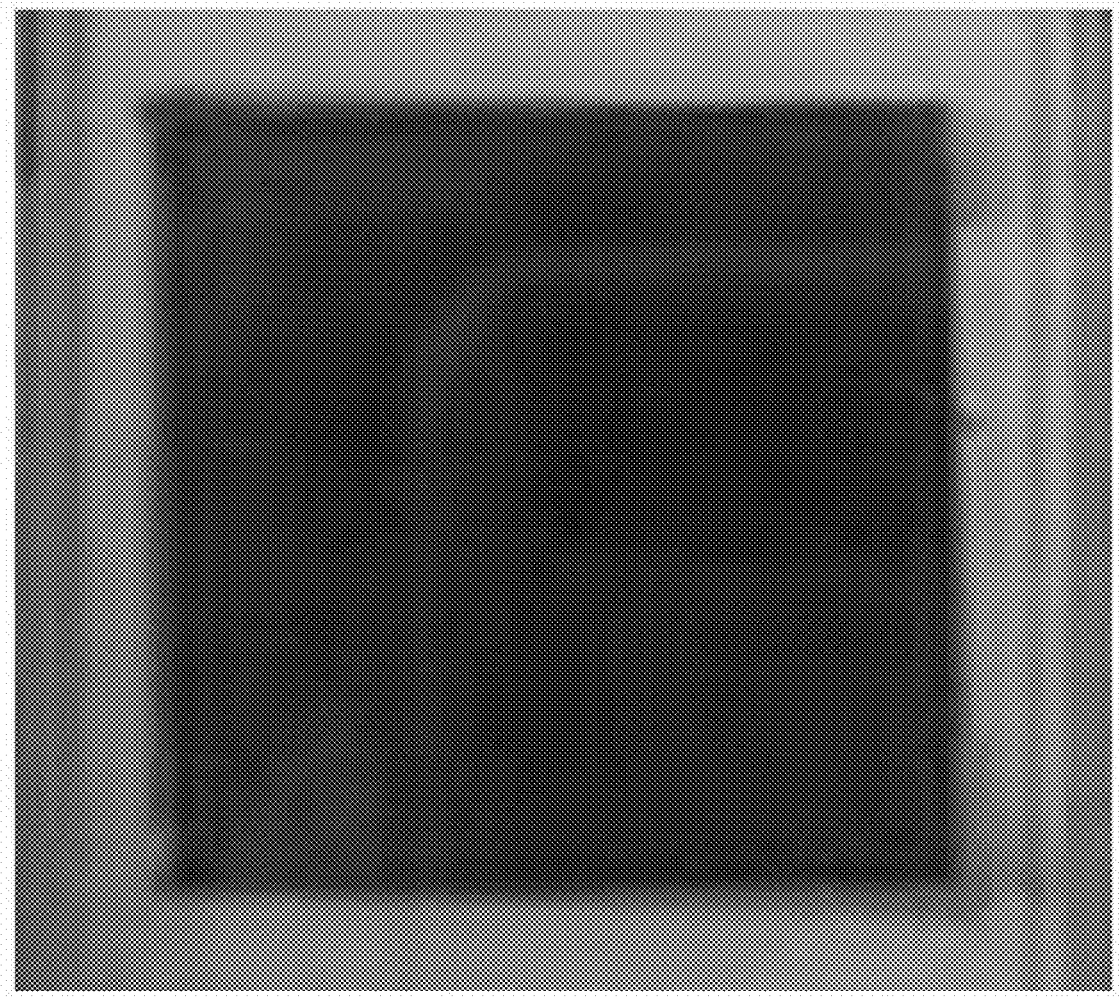

Referring to FIGS. 14B and 14C, the electrochromic device according to Example 14 has an operating voltage of about 0.5V, a potential window displaying green from about 0.5V to about 0.9V (FIG. 14B), and a potential window displaying red from about 1.0V to about 1.8V (FIG. 14C).

EXAMPLE 15

Synthesis of Chemical Formula 1O

Chemical Formula 1O

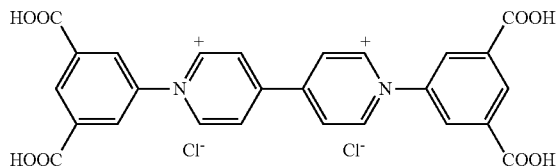

The compound of Chemical Formula 1O is synthesized according to the same method as in Example 14, except that 50 mmol (7.15 g) of 4-amino-(3,5-dicyano) benzene is used instead of 4-aminobenzonitrile.

The structure of the compound represented by chemical formula 1O is identified by its $^1$H NMR spectrum.

Fabrication of Electrochromic Device and Electrochromic Characteristic Identification An electrochromic device is fabricated according to the same method as in Example 1, except that the electrochromic material according to Example 15 is used. A voltage of 0V to 2.2V is applied to the electrochromic device, and the following electrochromic characteristics are observed.

Figure 15A:
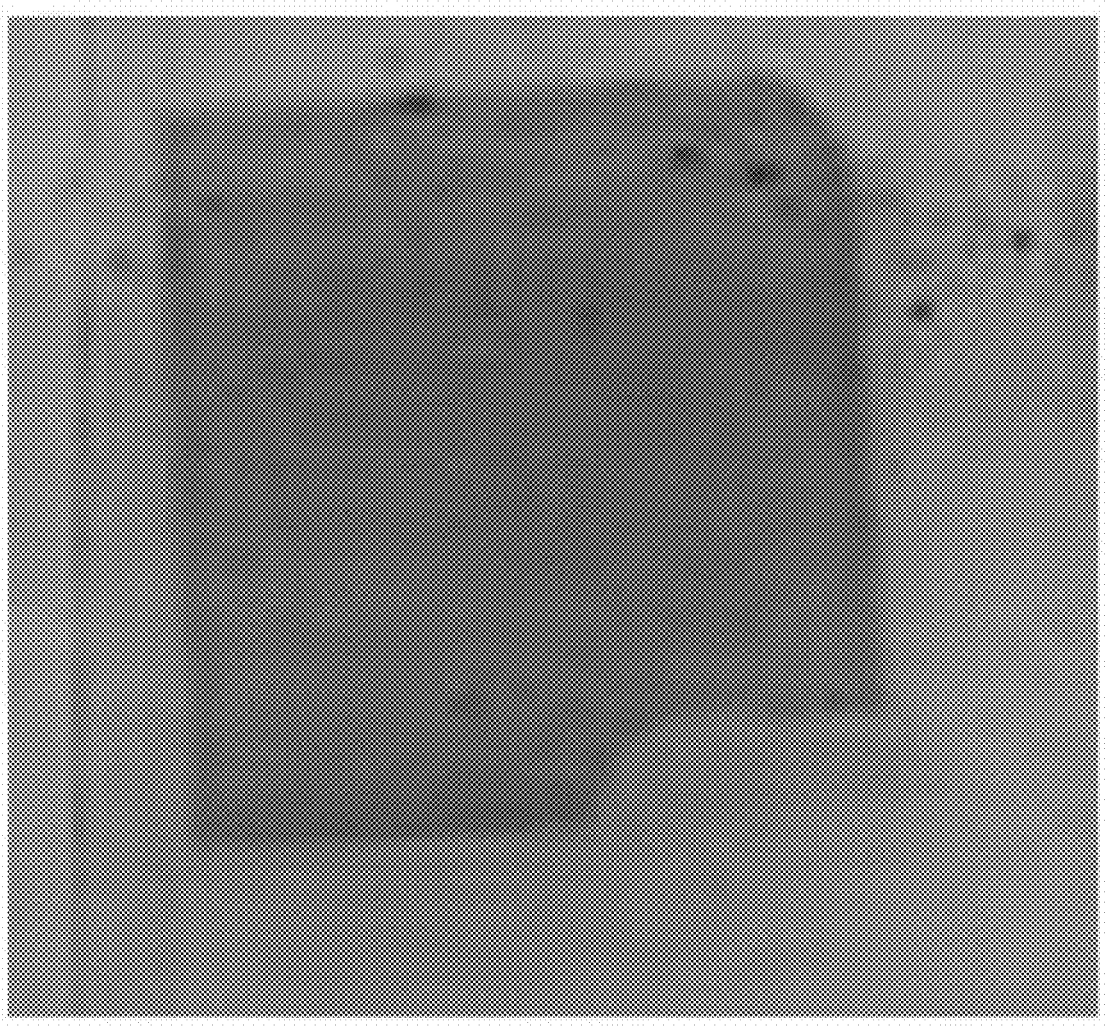
FIGS. 15A and 15B are respectively a photograph showing the color within a first voltage range, and a photograph showing the color within a second voltage range for the electrochromic material according to Example 15.
Figure 15B:
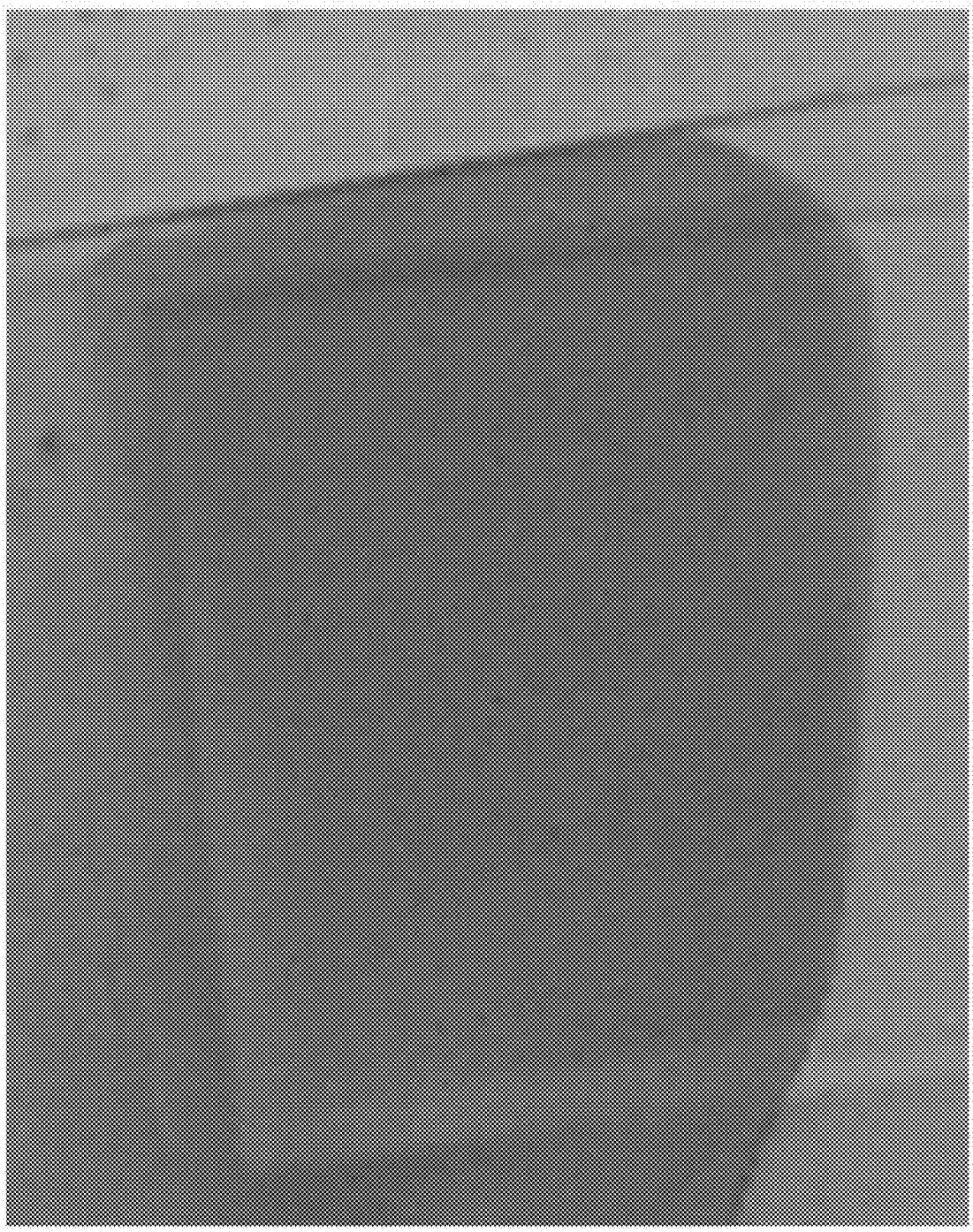

Referring to FIGS. 15B and 15C, the electrochromic device according to Example 15 has an operating voltage of about 0.5V, a potential window displaying greenish yellow from about 0.8V to about 1.5V (FIG. 15B), and a potential window displaying dark green from about 1.8V to about 2.4 V (FIG. 15C).

EXAMPLE 16

Synthesis of Chemical Formula 1P

Chemical Formula 1P

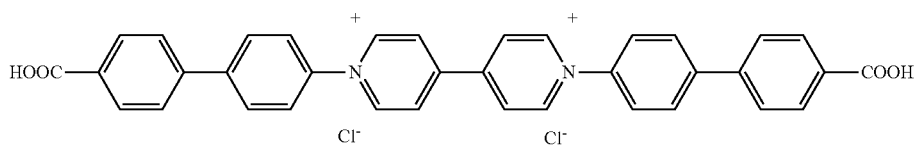

The compound of Chemical Formula 1P is synthesized according to the same method as in Example 14, except that 50 mmol (9.60 g) of 4-amino-4-cyanobiphenyl is used instead of 4-aminobenzonitrile.

Fabrication of Electrochromic Device and Electrochromic Characteristic Identification An electrochromic device is fabricated according to the same method as in Example 1, except that the electrochromic material according to Example 16 is used. A voltage of 0V to 2.2V is applied to the electrochromic device, and the following electrochromic characteristics are observed.

Figure 16A:
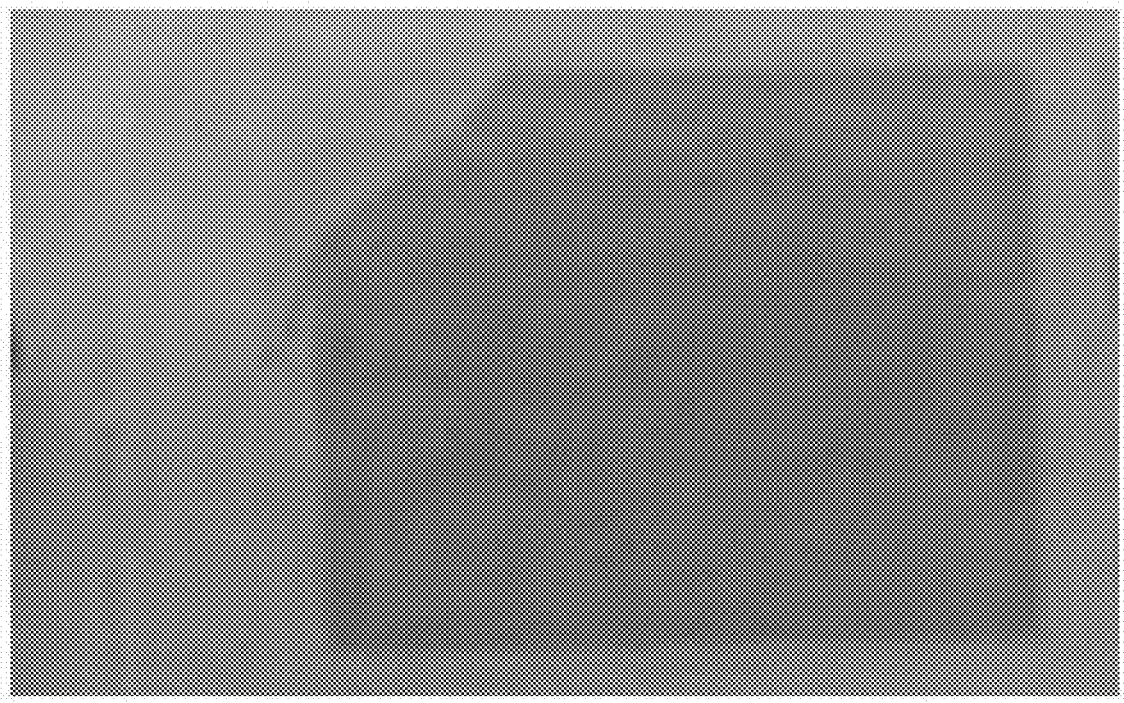
FIGS. 16A and 16B are respectively a photograph showing the color within a first voltage range, and a photograph showing the color within a second voltage range for the electrochromic material according to Example 16.
Figure 16B:
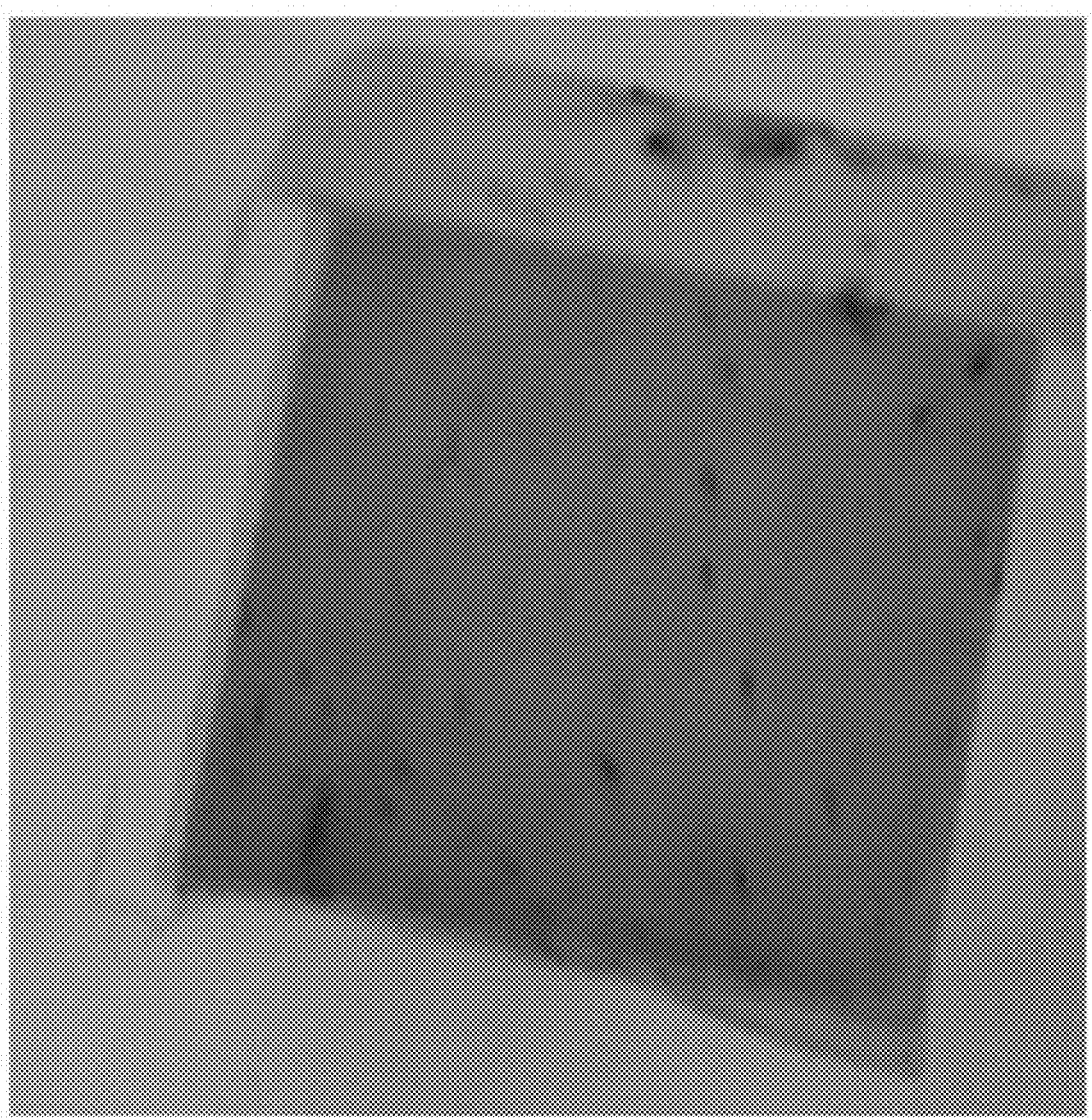

Referring to FIGS. 16B and 16C, the electrochromic device according to Example 16 has an operating voltage of about 0.5V, a potential window displaying greenish yellow from about 1.5 to about 2.0V (FIG. 16B), and a potential window displaying brown red from about 2.2 to about 2.8V (FIG. 16C).

EXAMPLE 17

Synthesis of Chemical Formula 1O

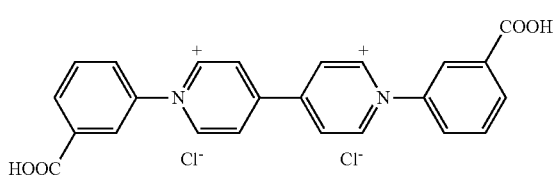

Chemical Formula 1Q

The compound of Chemical Formula 1O is synthesized according to the same method as in Example 14, except that 50 mmol (5.9 g) of 3-aminobenzonitrile is used instead of 4-aminobenzonitrile.

The structure of the compound represented by chemical formula 1Q is identified by its $^1$H NMR spectrum.

Fabrication of Electrochromic Device and Electrochromic Characteristic Identification An electrochromic device is fabricated according to the same method as in Example 1, except that the electrochromic material according to Example 17. A voltage of 0V to 2.2V is applied to the electrochromic device, and the following electrochromic characteristics.

Figure 17A:
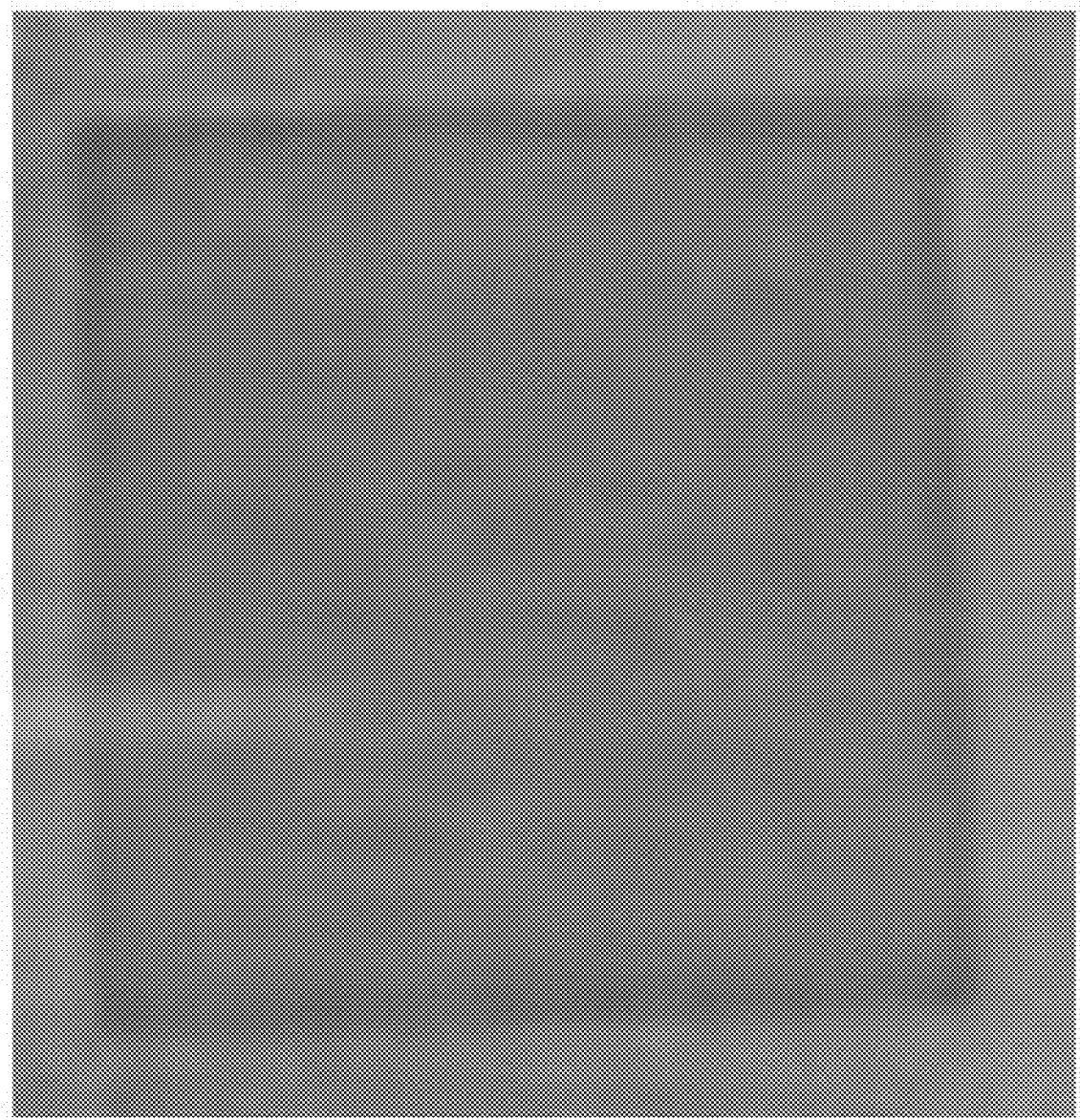
FIGS. 17A and 17B are respectively a photograph showing the color within a first voltage range, and a photograph showing the color within a second voltage range for the electrochromic material according to Example 17.
Figure 17B:
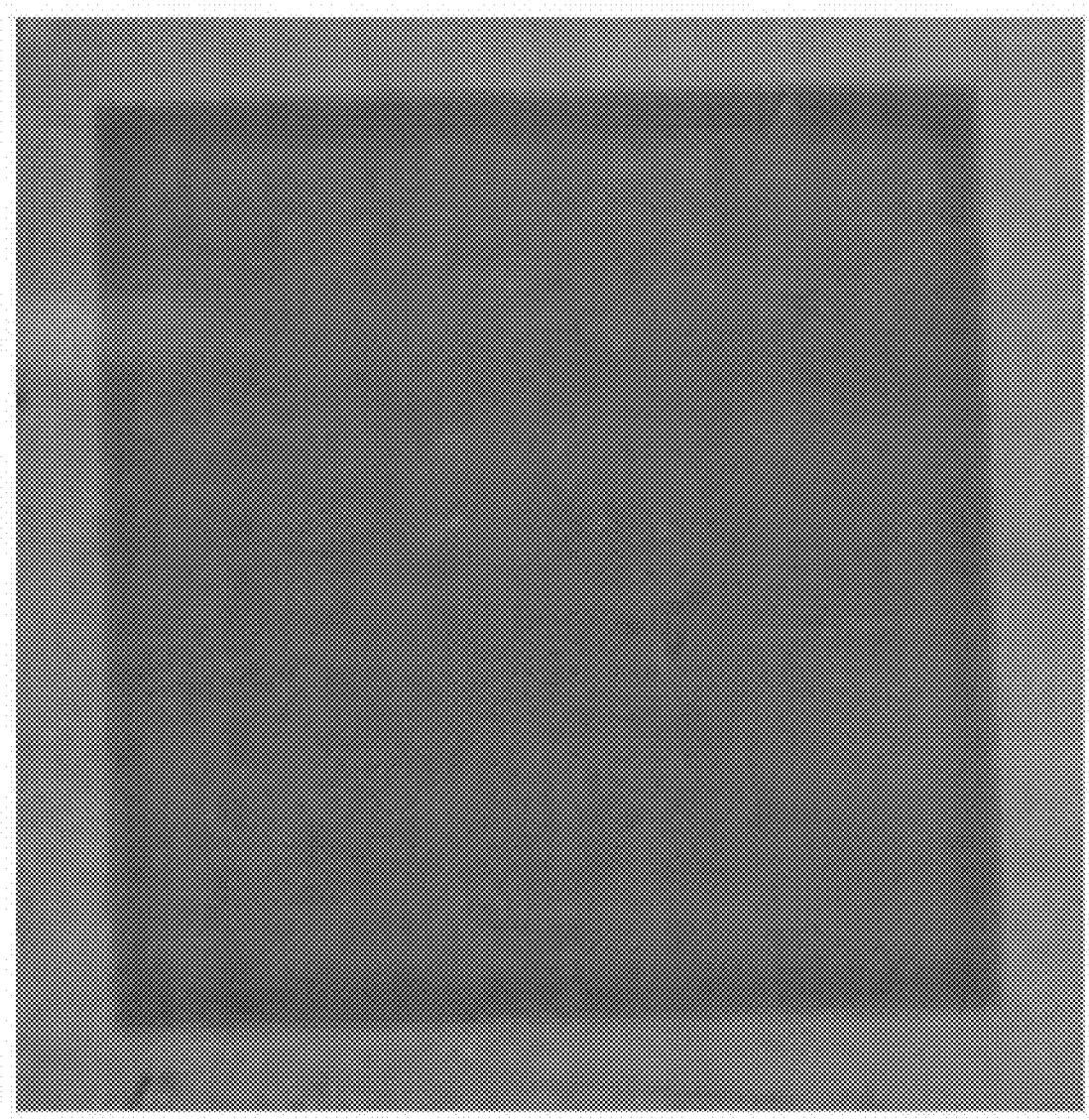

Referring to FIGS. 17B and 17C, the electrochromic device according to Example 17 has an operating voltage of about 0.5V, a potential window displaying greenish yellow from about 0.8 to about 1.3V (FIG. 17B), and a potential window displaying yellowish red from about 1.6 to about 2.5V (FIG. 17C).

EXAMPLE 18

Synthesis of Chemical Formula 1R Compound

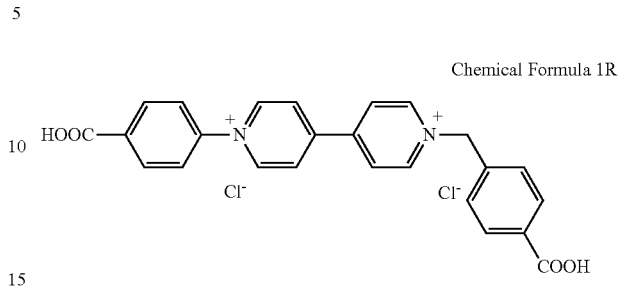

Chemical Formula 1R 1 mmol (0.118 g) of 4-aminobenzonitrile and 1 mmol (0.358 g) of 4-(2,4-dinitrophenyl)-4,4-dipyridylchloride are dissolved in 100 ml of ethanol. The mixture is heated at reflux for 2 days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven.

The obtained compound is dissolved in a minimum amount of acetonitrile, and heated at reflux for four days with 50 mmol (6.6 g) of 4-bromomethyl benzonitrile. The obtained nitrile compound is hydrolyzed in 50 ml of 37% (w/w) concentrated aqueous hydrochloric acid and then the solvent is removed. Next, acetone is added to the solution for reprecipitation, and it is then collected by filtration and dried, to provide a compound represented by Chemical Formula 1R. The yield is about 40%.

Fabrication of Electrochromic Device and Electrochromic Characteristic Identification An electrochromic device is fabricated according to the same method as in Example 1, except that the electrochromic material according to Example 18 is used. A voltage of 0V to 2.2V is applied to the electrochromic device, and the following electrochromic characteristics are observed.

Figure 18A:
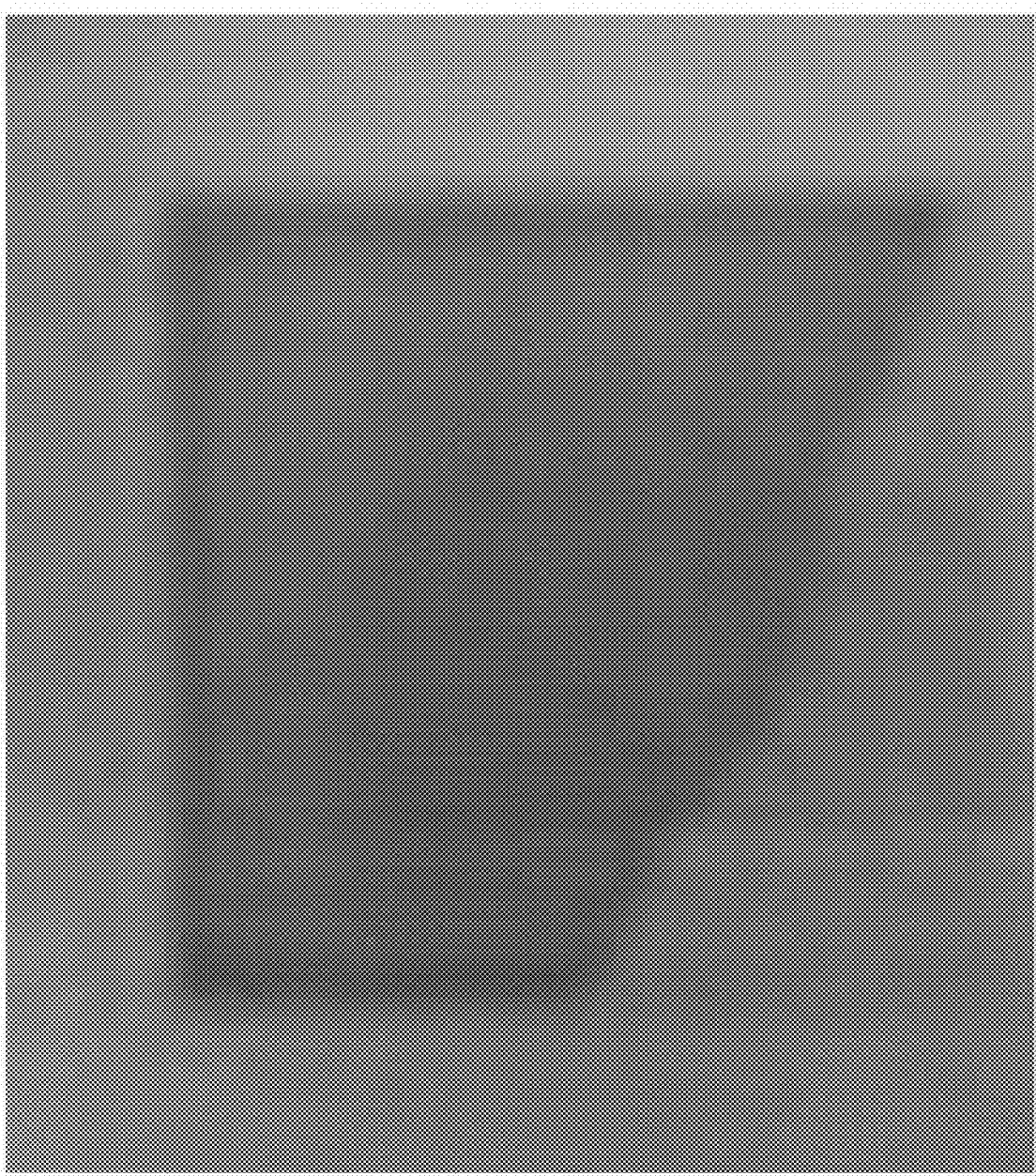
FIGS. 18A and 18B are respectively a photograph showing the color within a first voltage range, and a photograph showing the color within a second voltage range for the electrochromic material according to Example 18.
Figure 18B:
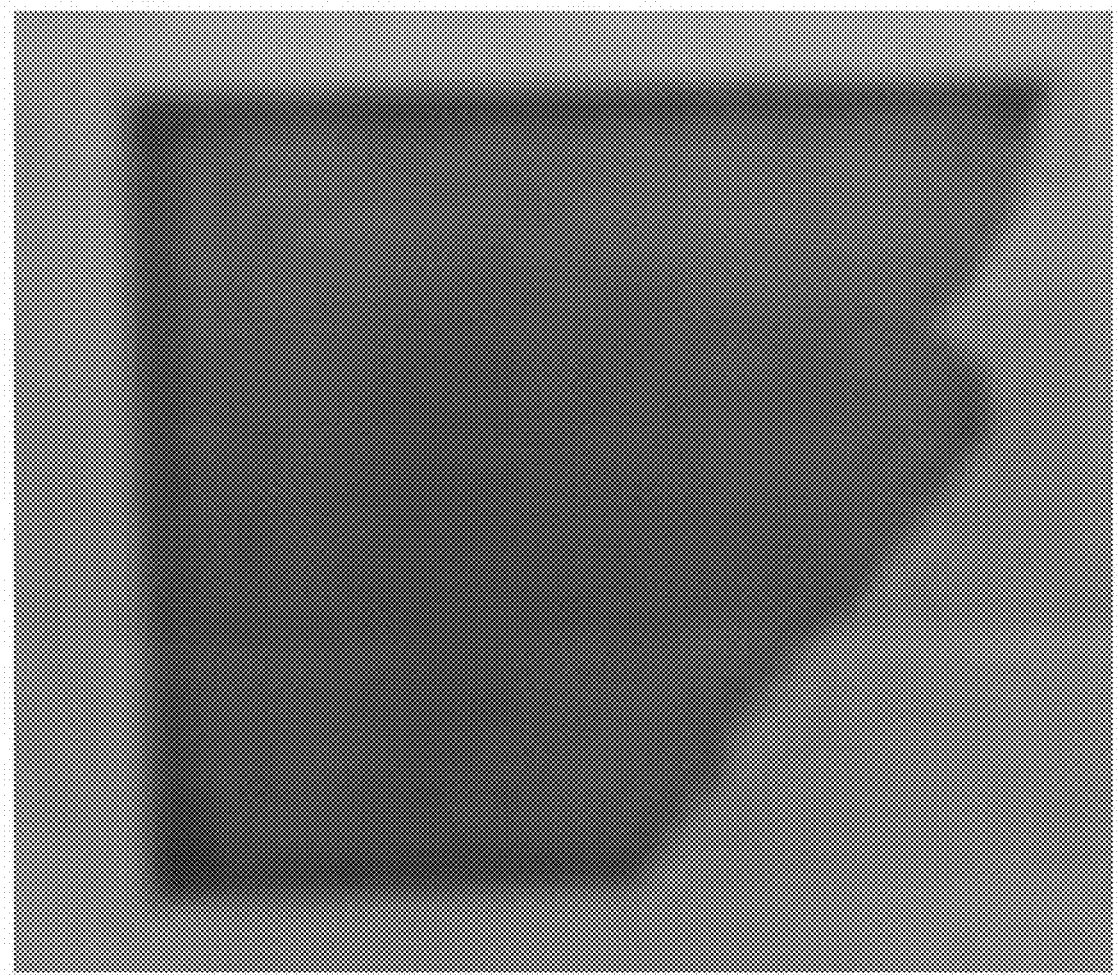

Referring to FIGS. 18B and 18C, the electrochromic device according to Example 18 has an operating voltage of about 0.5V, a potential window displaying greenish yellow from about 0.8 to about 1.3V (FIG. 18B), and a potential window displaying yellowish red from about 1.6 to about 2.5V (FIG. 18C).

EXAMPLE 19

Synthesis of Chemical Formula 1S Compound

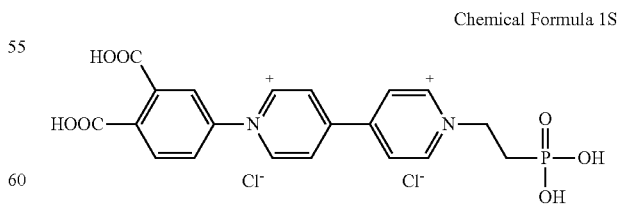

Chemical Formula 1S 1 mmol (0.143 g) of 4-aminophthalonitrile and 1 mmol (0.574 g) of 4-(2,4-dinitrophenyl)-4-diethylethyl phosphonate-4,4-dipyridyl chloride bromide are dissolved in 100 ml of ethanol. The mixture is heated at reflux for 2 days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven.

The thus-obtained compound is hydrolyzed in 50 ml of 37% (w/w) concentrated aqueous hydrochloric acid and then the solvent is removed. Next, acetone is added to the solution for reprecipitation, and it is then collected by filtration and dried, to provide a compound represented by Chemical Formula 1S. The yield is about 40%.

Fabrication of Electrochromic Device and Electrochromic Characteristic Identification An electrochromic device is fabricated according to the same method as in Example 1, except that the electrochromic material according to Example 19 is used. A voltage of 0V to 2.2V is applied to the electrochromic device, and the following electrochromic characteristics are observed.

Figure 19A:
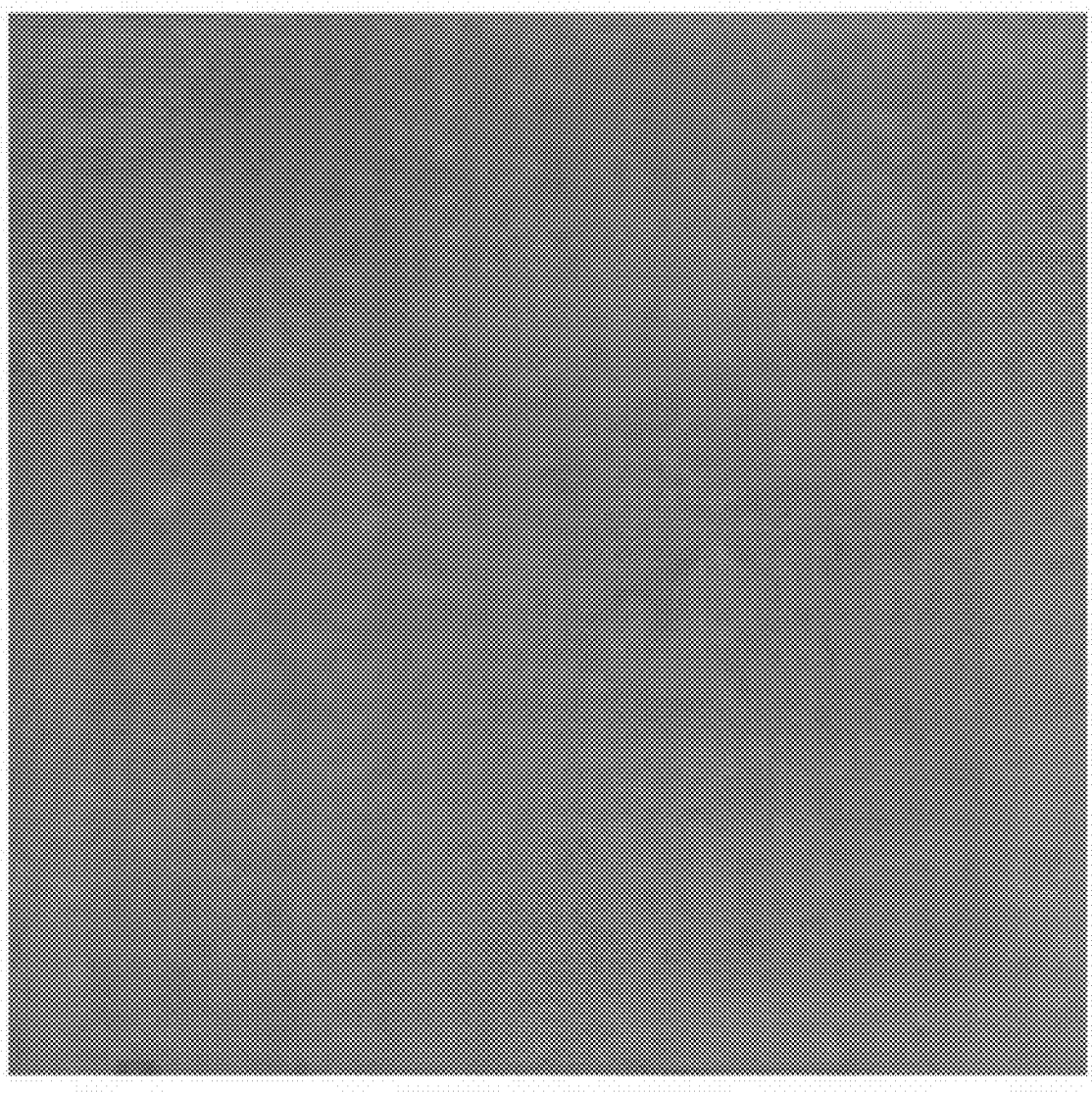
FIGS. 19A and 19B are respectively a photograph showing the color within a first voltage range, and a photograph showing the color within a second voltage range for the electrochromic material according to Example 19.
Figure 19B:
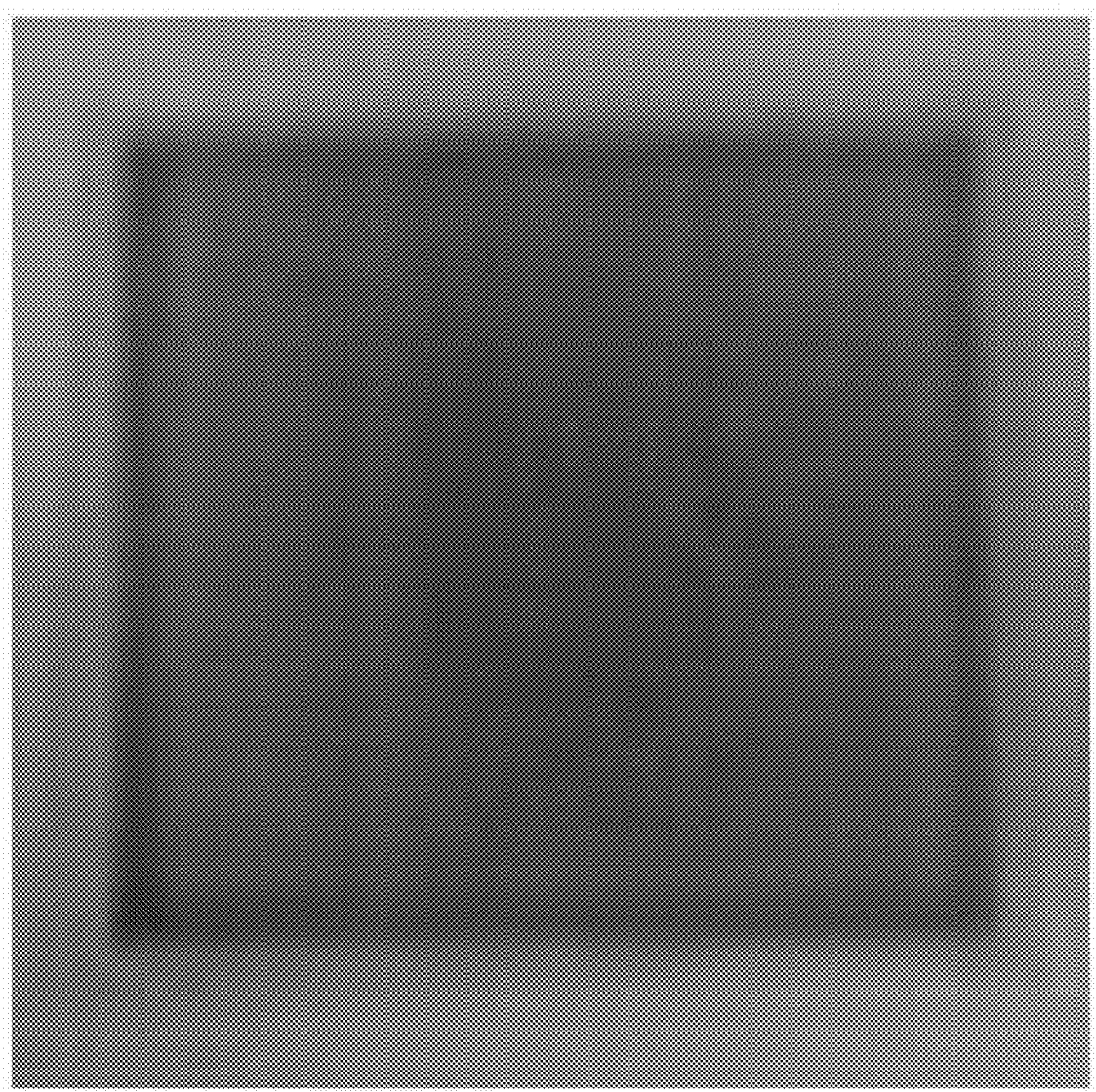

Referring to FIGS. 19B and 19C, the electrochromic device according to Example 19 has an operating voltage of about 0.5V, a potential window displaying greenish yellow from about 0.8 to about 1.1V (FIG. 19B), and a potential window displaying yellowish red from about 1.3 to about 2.1V (FIG. 19C).

EXAMPLE 20

Synthesis of Chemical Formula 1T Compound

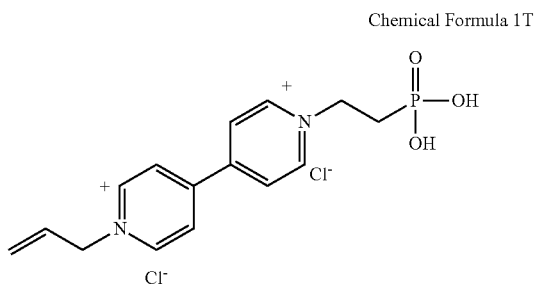

Chemical Formula 1T

The compound of Chemical Formula 1T is synthesized according to the same method as in Example 19, except that 50 mmol (2.5 g) of allylamine is used instead of 4-aminophthalonitrile.

The structure of the compound represented by chemical formula 1T is identified by its $^1$H NMR spectrum.

Fabrication of Electrochromic Device and Electrochromic Characteristic Identification An electrochromic device is fabricated according to the same method as in Example 1, except that the electrochromic material according to Example 20 is used. A voltage of 0V to 2.2V is applied to the electrochromic device, and the following electrochromic characteristics are observed.

Figure 20A:
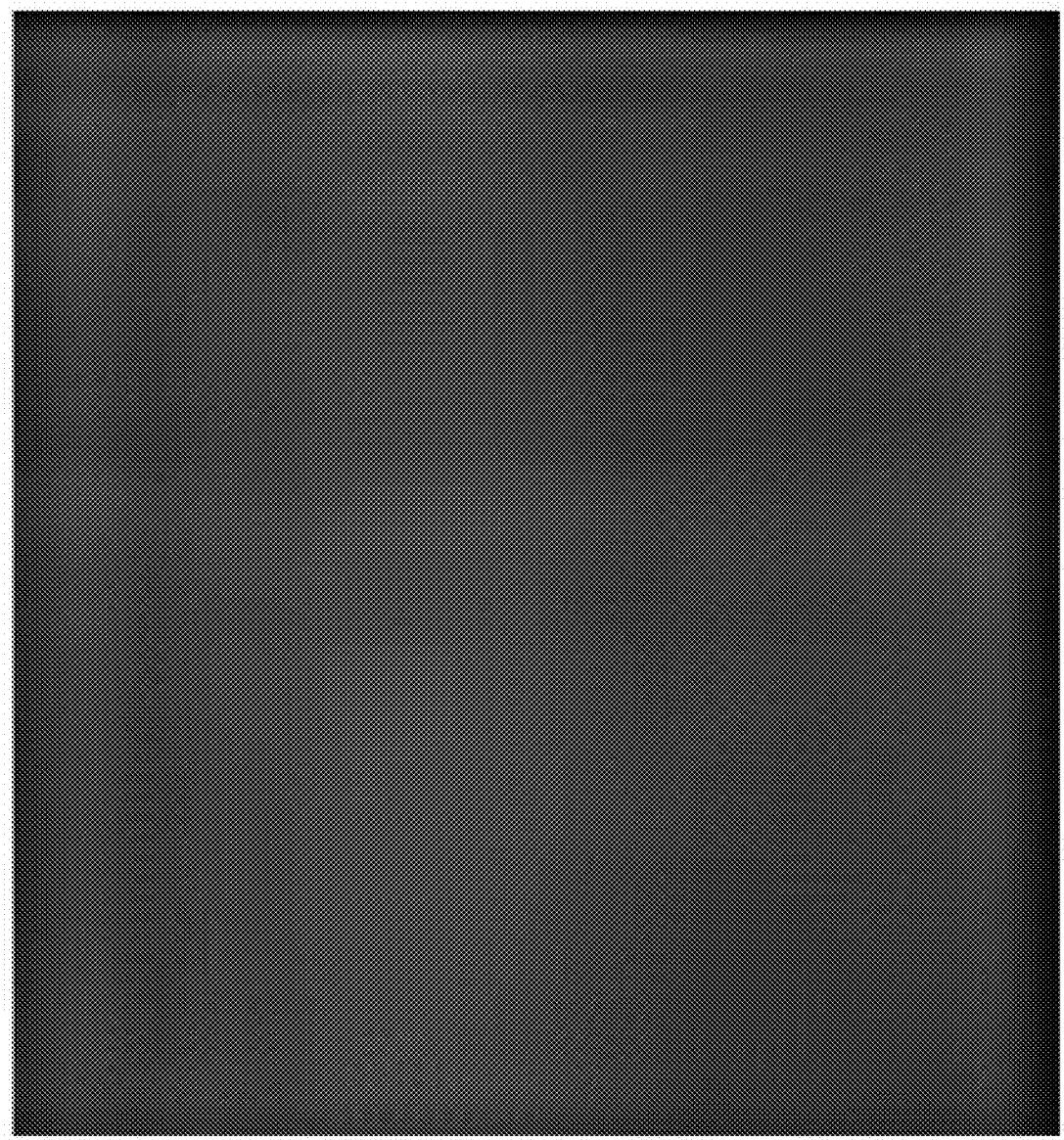
FIGS. 20A and 20B are respectively a photograph showing the color within a first voltage range, and a photograph showing the color within a second voltage range for the electrochromic material according to Example 20.
Figure 20B:
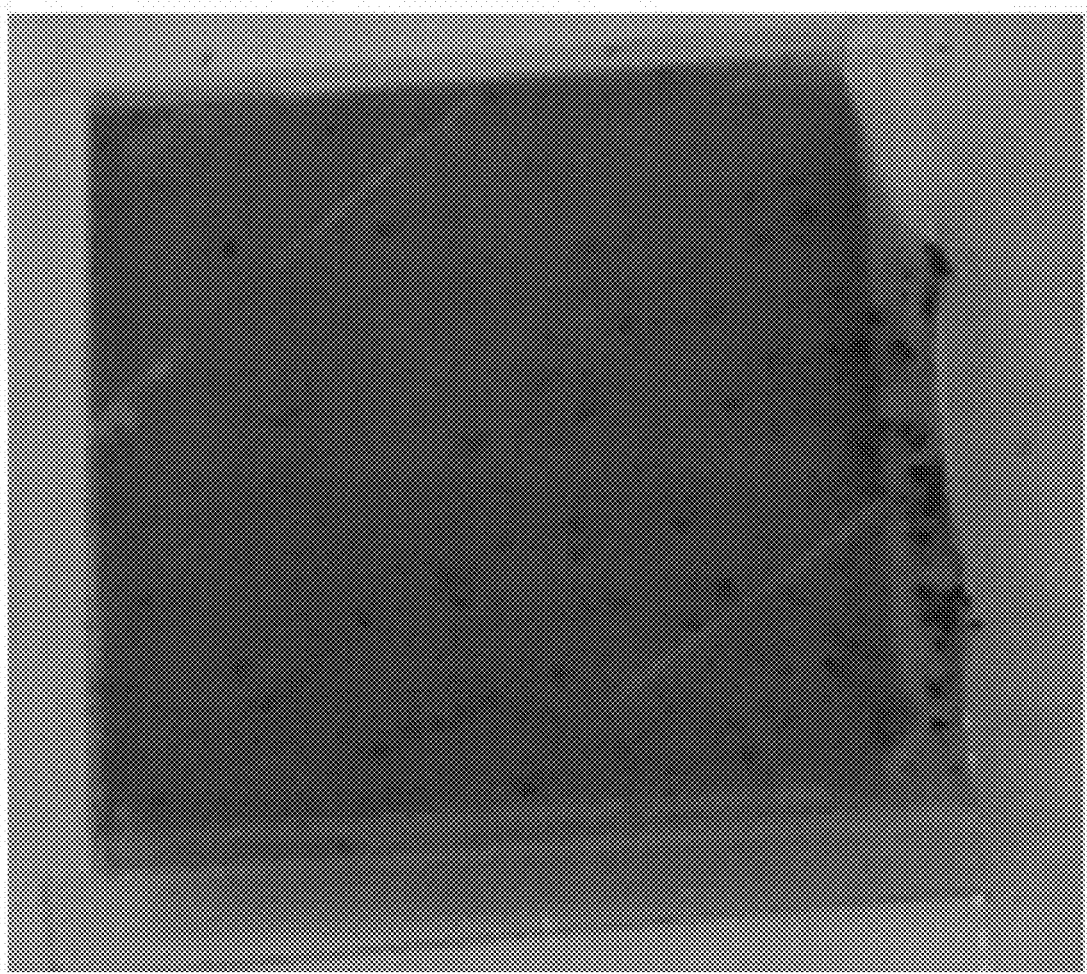

Referring to FIGS. 20B and 20C, the electrochromic device according to Example 20 has an operating voltage of about 0.5V, a potential window displaying dark blue from about 1.0V to about 1.5V (FIG. 20B), and a potential window displaying grayish green from about 1.6V to about 2.1V (FIG. 20C).

EXAMPLE 21

Synthesis of Chemical Formula 1U compound

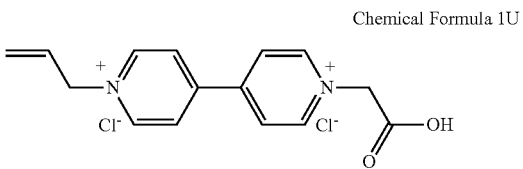

Chemical Formula 1U 1 mmol (0.120 g) of bromo acetnitrile and 1 mmol (0.358 g) of 4-(2,4-dinitrophenyl)-4,4-dipyridylchloride are dissolved in 100 ml of ethanol. The mixture is heated at reflux for 2 days. Then, the yellow solid obtained after removing the solvent is agitated in 500 ml of acetone and collected by filtration. The process is repeated five times. The precipitate is collected by filtration and rinsed several times with acetone. Then, the precipitate is dried in a 70° C. oven.

The thus-obtained compound is hydrolyzed in 50 ml of 37% (w/w) concentrated aqueous hydrochloric acid and then a solvent is removed. Next, acetone is added to the solution for reprecipitation, and it is then collected by filtration and dried, to provide a compound represented by Chemical Formula 1U. The yield is about 40%.

The structure of the compound represented by chemical formula 1U is identified by its $^1$H NMR spectrum.

Fabrication of Electrochromic Device and Electrochromic Characteristic Identification An electrochromic device is fabricated according to the same method as in Example 1, except that the electrochromic material according to Example 21 is used. A voltage of 0V to 2.2V is applied to the electrochromic device, and the following electrochromic characteristics are observed.

Figure 21A:
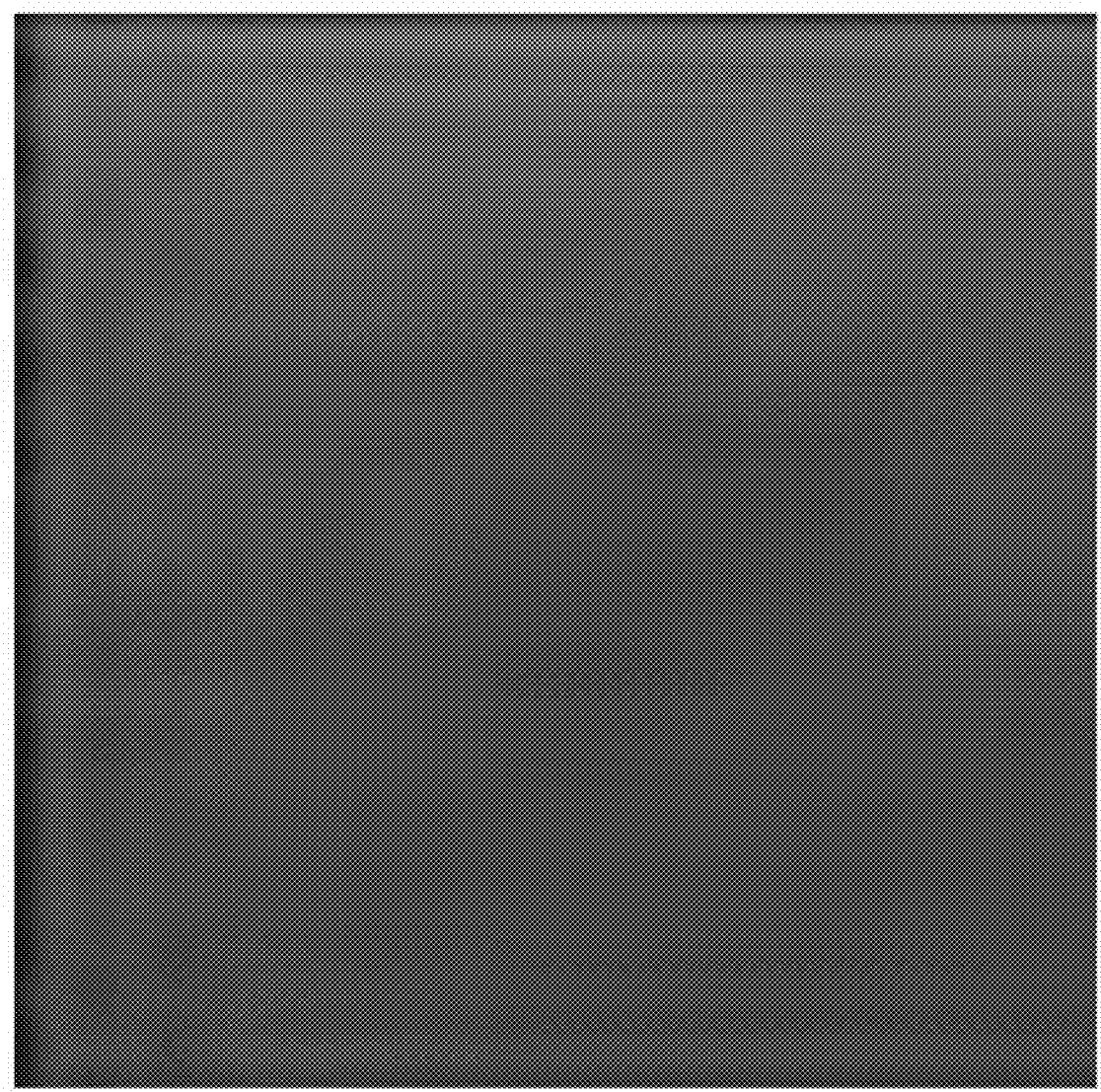
FIGS. 21A and 21B are respectively a photograph showing the color within a first voltage range, and a photograph showing the color within a second voltage range for the electrochromic material according to Example 21.
Figure 21B:
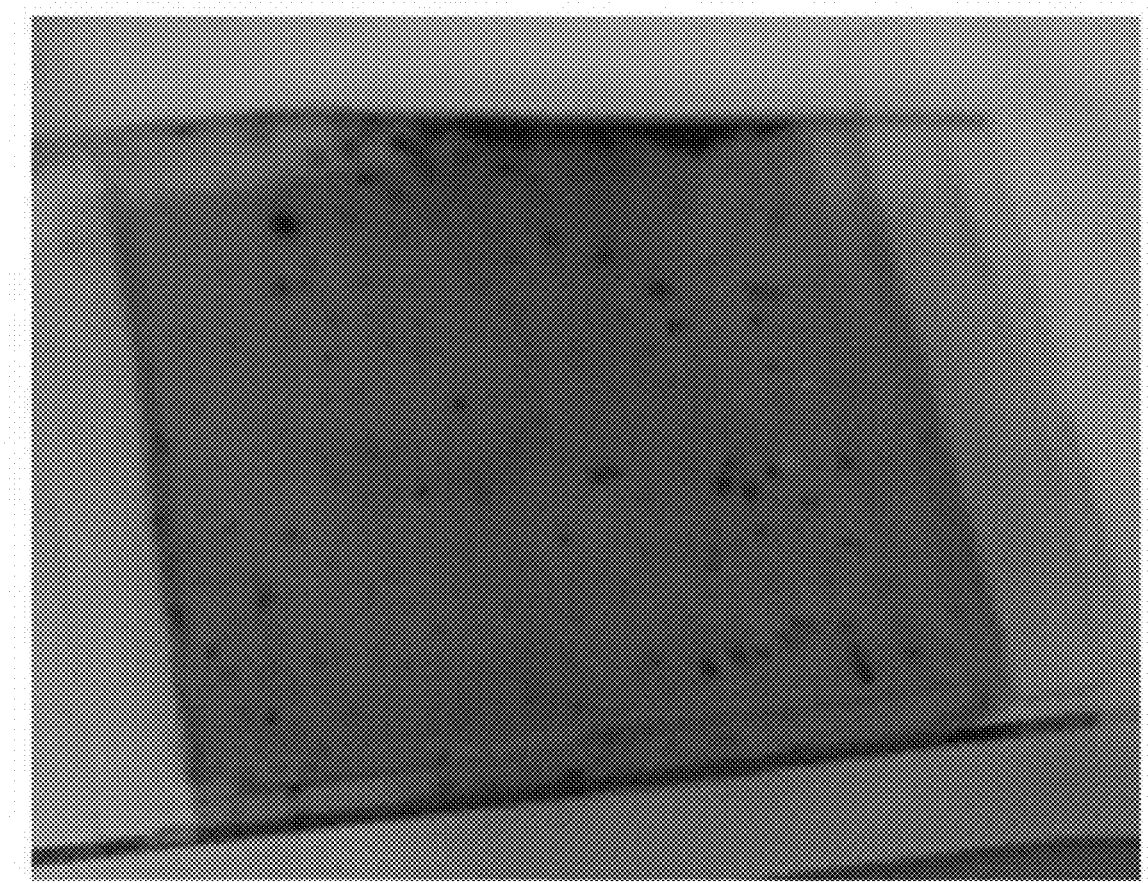

Referring to FIGS. 21B and 21C, the electrochromic device according to Example 21 has an operating voltage of about 0.5V, a potential window displaying dark blue from about 1.0 to about 1.5V (FIG. 21B), and a potential window displaying grayish green from about 1.6 to about 2.1V (FIG. 21C).

EXAMPLE 22

Synthesis of Chemical Formula 1X Compound

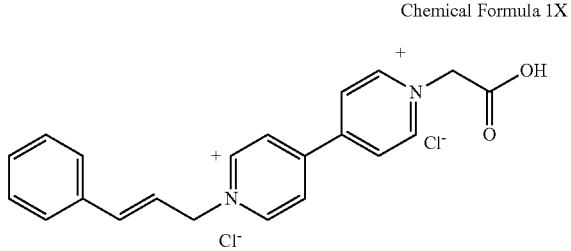

Chemical Formula 1X

The compound of Chemical Formula 1X is synthesized according to the same method as in Example 21, except that 50 mmol (6.0 g) of amino stilbene is used instead of allylamine.

The structure of the compound represented by chemical formula 1X is identified by $^1$H NMR spectrum.

Fabrication of Electrochromic Device and Electrochromic Characteristic Identification An electrochromic device is fabricated according to the same method as in Example 1, except that the electrochromic material according to Example 22 is used. A voltage of 0V to 2.2V is applied to the electrochromic device, and the following electrochromic characteristics are observed.

The electrochromic device according to Example 22 has an operating voltage of about 0.5V, a potential window displaying dark blue from about 1.0V to about 1.5V, and a potential window displaying yellowish green from about 1.6V to about 2.1V.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An electrochromic material represented by the following Chemical Formula 1:

Chemical Formula 1

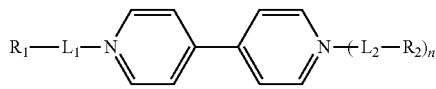

wherein, in Chemical Formula 1, $R_1$ is a substituted or unsubstituted imidazole, a substituted or unsubstituted oxazole, a substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group or combination comprising at least one of the foregoing, $R_2$ is a substituted or unsubstituted imidazole, substituted or unsubstituted oxazole, substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group; a phosphonium acid group; a carboxylic acid group; a sulfonic acid group; a hydroxy group; a substituted or unsubstituted C1 to C30 alkyl group, a substituted or unsubstituted C1 to C30 alkenyl group, a substituted or unsubstituted C3 to C30 cycloalkyl group, a substituted or unsubstituted C3 to C30 cycloalkenyl group, a substituted or unsubstituted C6 to C30 aryl group, a substituted or unsubstituted C7 to C30 aralkyl group, or a substituted or unsubstituted C2 to C30 heteroaryl group, substituted with a phosphonium acid group, a carboxylic acid group, a sulfonic acid group, or a hydroxy group; or a combination comprising at least one of the foregoing groups, $L_1$ and $L_2$ are each independently a single bond, a substituted or unsubstituted C1 to C30 alkylene group, a substituted or unsubstituted C3 to C30 cycloalkylene group, a substituted or unsubstituted C2 to C30 heterocycloalkylene group, a substituted or unsubstituted C6 to C30 arylene group, a substituted or unsubstituted C7 to C30 aralkylene group, a substituted or unsubstituted C2 to C30 heteroarylene group, a substituted or unsubstituted C3 to C30 heteroaralkylene group, a substituted or unsubstituted heterocycloalkylene group, a substituted or unsubstituted heterocycloalkenylene group, or a combination comprising at least one of the foregoing groups, and n is 0 or 1.

2. The electrochromic material of claim 1, wherein $R_1$ is one selected the following Chemical Formula 2:

Chemical Formula 2

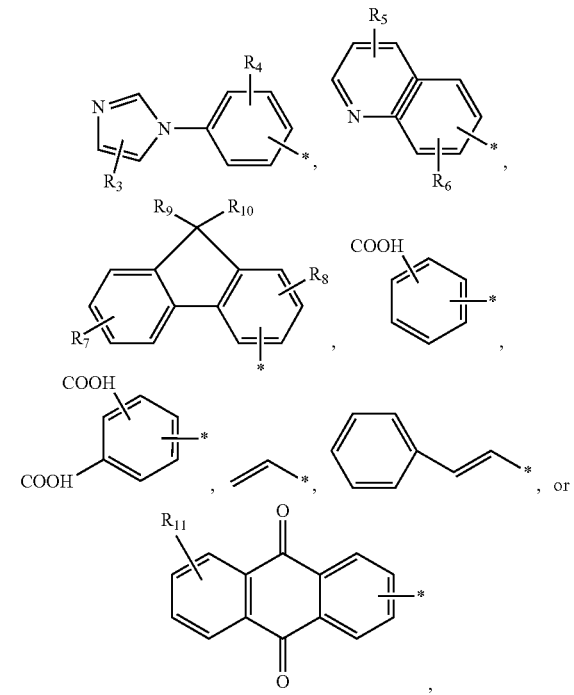

wherein, in Chemical Formula 2, $R_3$ to $R_{11}$ are each independently a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C7 to C30 aralkyl group, a substituted or unsubstituted C2 to C30 heteroaryl group, a substituted or unsubstituted C3 to C30 heteroaralkyl group, or a combination comprising at least one of the foregoing groups.

3. The electrochromic material of claim 1, wherein $R_2$ comprises a group selected from the groups represented by the following Chemical Formulae 2 and 3:

Chemical Formula 2

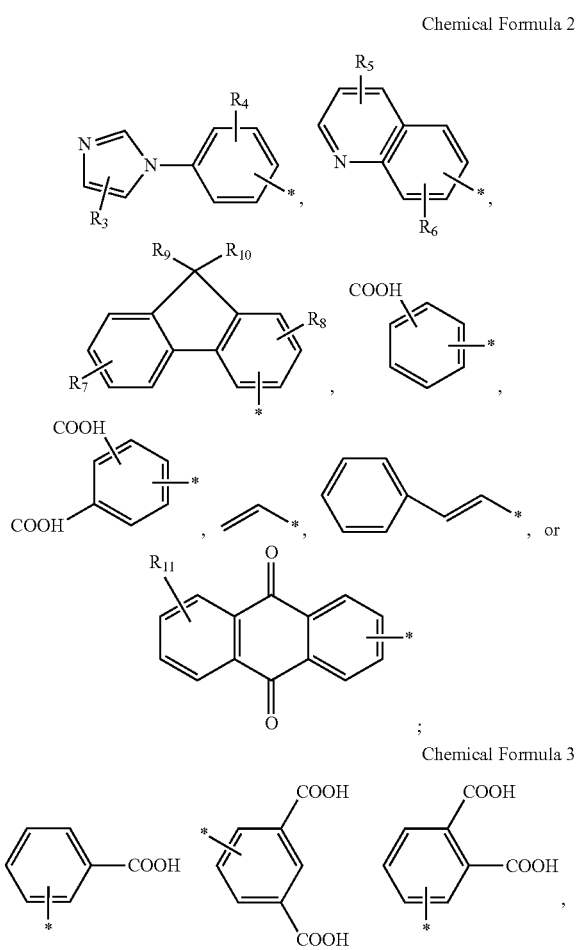

Chemical Formula 3

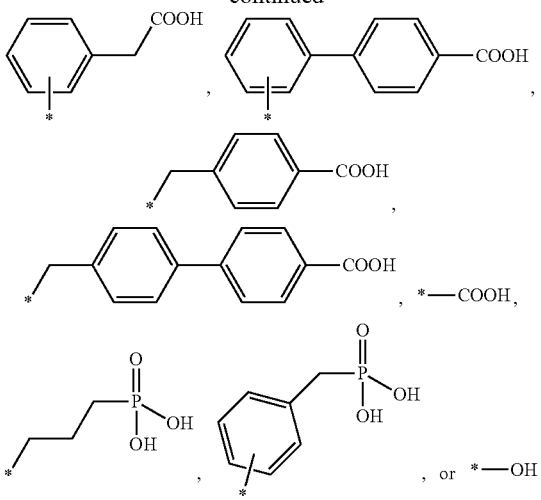

wherein, in Chemical Formula 2, $R_3$ to $R_{11}$ are each independently a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C7 to C30 aralkyl group, a substituted or unsubstituted C2 to C30 heteroaryl group, a substituted or unsubstituted C3 to C30 heteroaralkyl group, or a combination comprising at least one of the foregoing groups.

4. The electrochromic material of claim 1, wherein the electrochromic material displays different colors at different voltage ranges.

5. The electrochromic material of claim 4, wherein the electrochromic material displays green within a first voltage range, and red within a second voltage range.

6. The electrochromic material of claim 1, wherein the electrochromic material comprises at least one compound represented by the following Chemical Formulae 1A to 1X:

Chemical Formula 1A

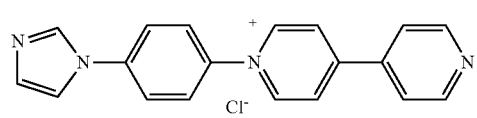

Chemical Formula 1B

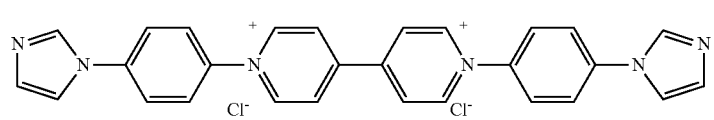

Chemical Formula 1C

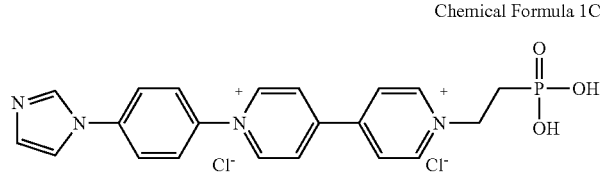

Chemical Formula 1D

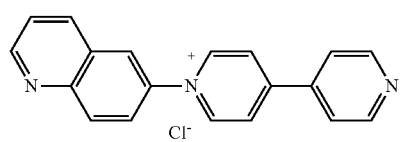

Chemical Formula 1E
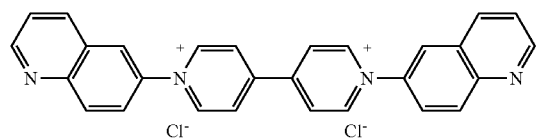
Chemical Formula 1F
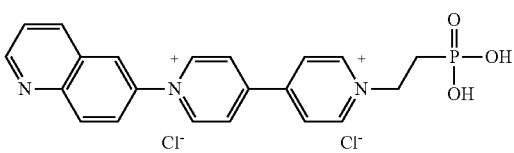
Chemical Formula 1G
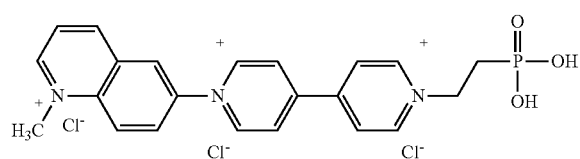
Chemical Formula 1H
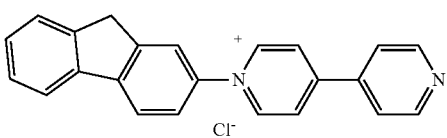
Chemical Formula 1I
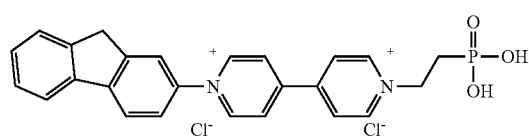
Chemical Formula 1J
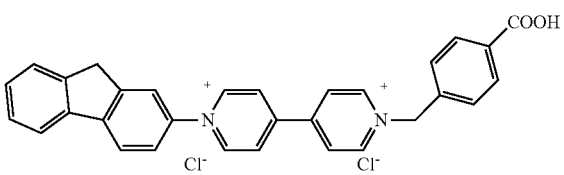
Chemical Formula 1K
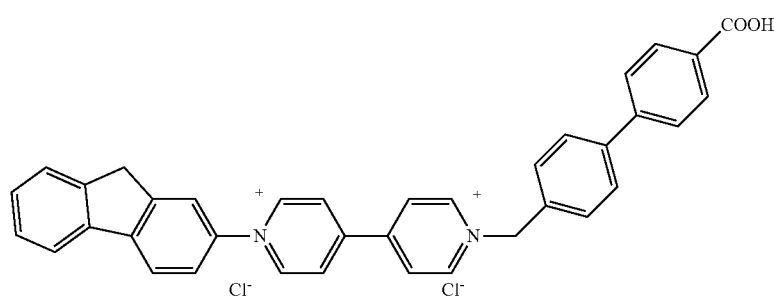
Chemical Formula 1L
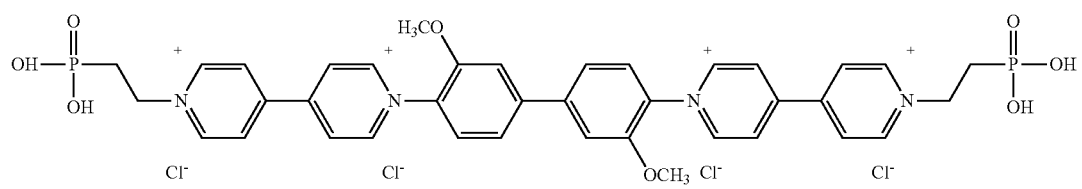
Chemical Formula 1M
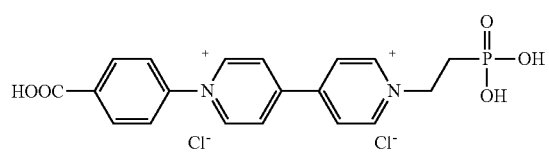
Chemical Formula 1N
Chemical Formula 1O
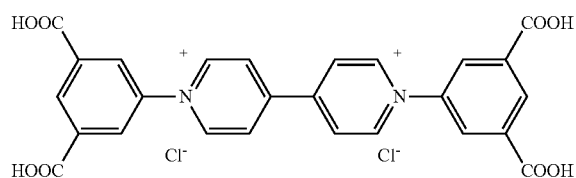
Chemical Formula 1P
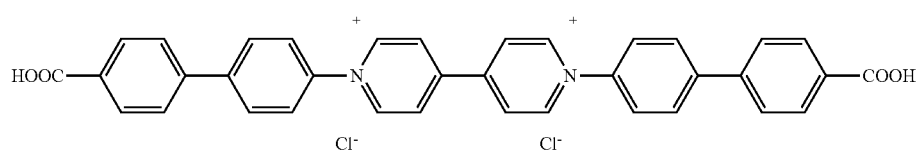

-continued

Chemical Formula 1Q
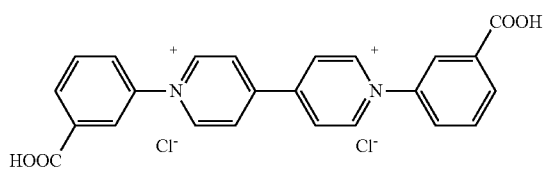

Chemical Formula 1R
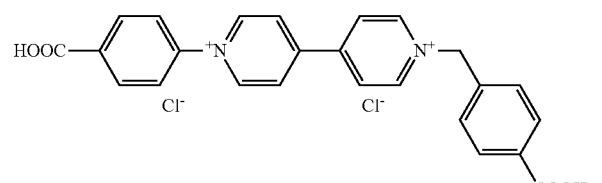

Chemical Formula 1S
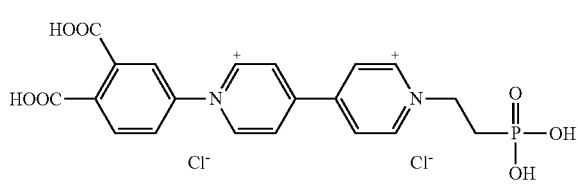

Chemical Formula 1T
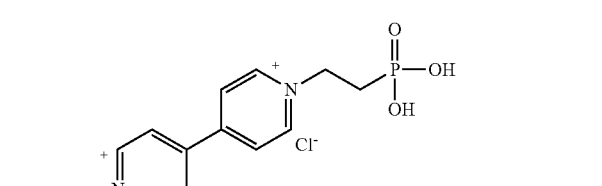

Chemical Formula 1U
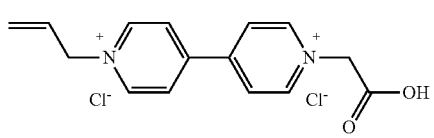

Chemical Formula 1V
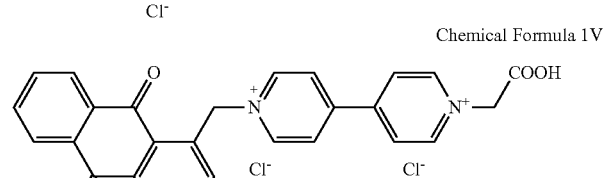

Chemical Formula 1W
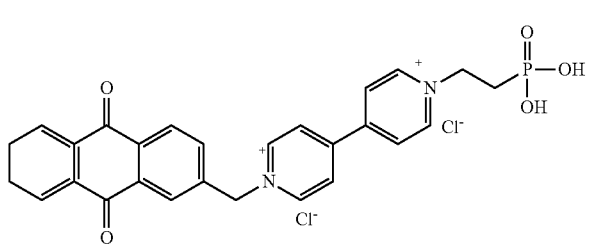

Chemical Formula 1X
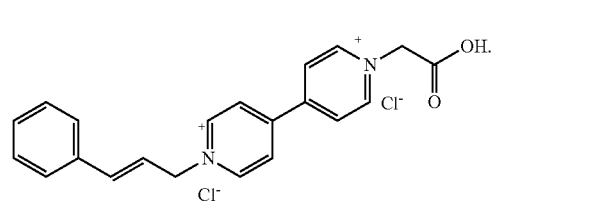

7. An electrochromic device comprising:
a first electrode and a second electrode;
an electrochromic material on either one of the first electrode and the second electrode; and
an electrolyte layer between the first electrode and the second electrode,
wherein the electrochromic material comprises a compound represented by Chemical Formula 1:

Chemical Formula 1
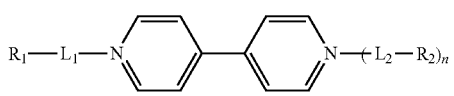

wherein, in Chemical Formula 1,
$R_1$ is a substituted or unsubstituted imidazole, a substituted or unsubstituted oxazole, a substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group, or a combination comprising at least one of the foregoing groups, $R_2$ is a substituted or unsubstituted imidazole, a substituted or unsubstituted oxazole, a substituted or unsubstituted thiazole, a substituted or unsubstituted pyrrole, a substituted or unsubstituted pyrrolidine, a substituted or unsubstituted pyridine, a substituted or unsubstituted quinoline, a substituted or unsubstituted fluorene, a substituted or unsubstituted phenyl, a substituted or unsubstituted biphenyl, a substituted or unsubstituted naphthyl, a substituted or unsubstituted anthracene, a substituted or unsubstituted phenanthrene, a substituted or unsubstituted benzoic acid, a substituted or unsubstituted phthalic acid, a substituted or unsubstituted benzenetricarboxylic acid, a substituted or unsubstituted benzene tetracarboxylic acid (mellitic acid), a substituted or unsubstituted naphthalene carboxylic acid, a substituted or unsubstituted naphthoquinone, a substituted or unsubstituted anthraquinone, a substituted or unsubstituted vinyl group, a fluorine-containing group; a phosphonium acid group; a carboxylic acid group; a sulfonic acid group; a hydroxy group; a phosphonium acid group, a carboxylic acid group, a sulfonic acid group, or a substituted or unsubstituted C1 to C30 alkyl group, a substituted or unsubstituted C3 to C30 cycloalkyl group, a substituted or unsubstituted C6 to C30 aryl group, or a substituted or unsubstituted C2 to C30 heteroaryl group substituted with a phosphonium acid group, a carboxylic acid group, a sulfonic acid group, or a hydroxy group; or a combination comprising at least one of the foregoing groups, $L_1$ and $L_2$ are each independently a single bond, a substituted or unsubstituted C1 to C30 alkylene group, a substituted or unsubstituted C3 to C30 cycloalkylene group, a substituted or unsubstituted C2 to C30 heterocycloalkylene group, a substituted or unsubstituted. C6 to C30 arylene group, a substituted or unsubstituted C7 to C30 aralkylene group, a substituted or unsubstituted C2 to C30 heteroarylene group, a substituted or unsubstituted C3 to C30 heteroaralkylene group, a substituted or unsubstituted heterocycloalkylene group, a substituted or unsubstituted heterocycloalkenylene group, or a combination comprising at least one of the foregoing groups, and n is 0 or 1.

8. The electrochromic device of claim 6, wherein $R_1$ in the Chemical Formula 1 is selected from the following Chemical Formula 2:

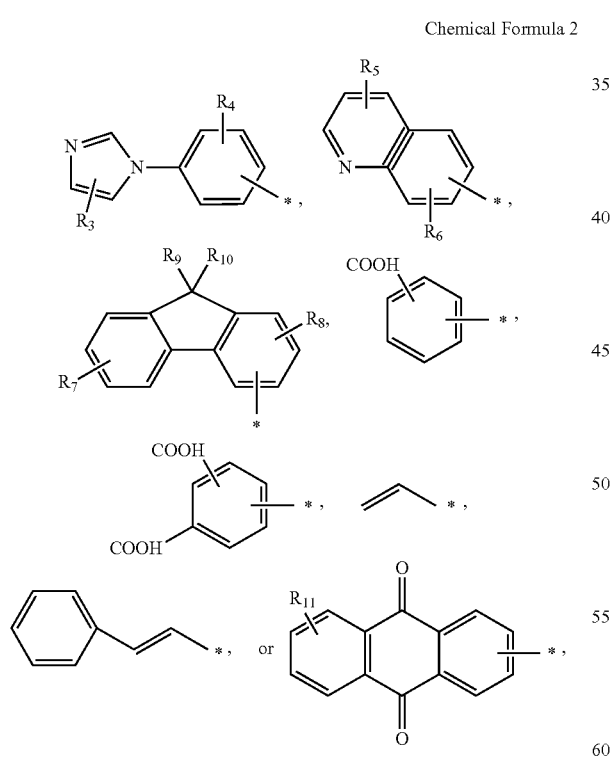

Chemical Formula 2 wherein, n Chemical Formula 2, $R_3$ to $R_{11}$ are each independently a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C7 to C30 aralkyl group, a substituted or unsubstituted C2 to C30 heteroaryl group, a substituted or unsubstituted C3 to C30 heteroaralkyl group, or a combination comprising at least one of the foregoing groups.

9. The electrochromic device of claim 7, wherein

In Chemical Formula 2, $R_2$ is one of the groups represented by the following Chemical Formulae 2 and 3:

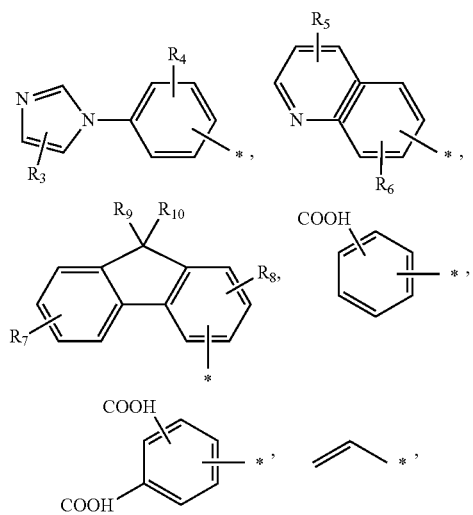

Chemical Formula 2

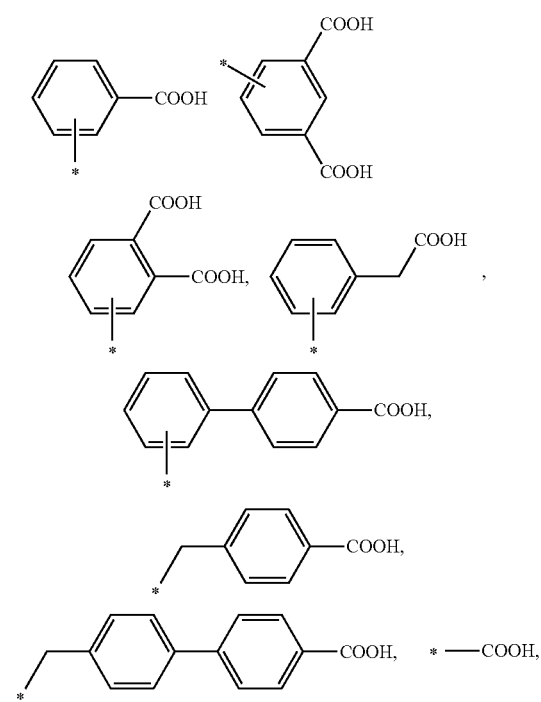

Chemical Formula 3

-continued

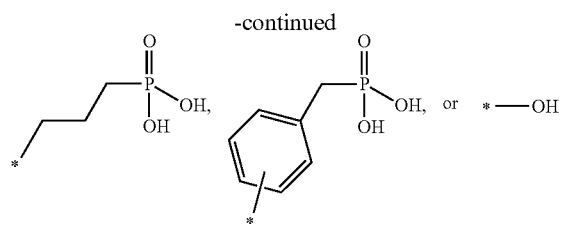

wherein, in Chemical Formula 2, $R_3$ to $R_{11}$ are each independently a substituted or unsubstituted C1 to C30 alkyl group, a substituted or unsubstituted C3 to C30 cycloalkyl group, a substituted or unsubstituted C2 to C30 heterocycloalkyl group, a substituted or unsubstituted C6 to C30 aryl group, a substituted or unsubstituted C7 to C30 aralkyl group, a substituted or unsubstituted C2 to C30 heteroaryl group, a substituted or unsubstituted C3 to C30 heteroaralkyl group, or a combination comprising at least one of the foregoing groups.

10. The electrochromic device of claim 7, wherein the electrochromic material is a multicolor electrochromic material that displays different colors at different voltage ranges.

11. The electrochromic device of claim 10, wherein the electrochromic material displays green within a first voltage range, and red within a second voltage range.

12. The electrochromic device of claim 7, wherein the electrochromic material comprises at least one compound represented by the following Chemical Formulae 1A to 1X:

Chemical Formula 1A

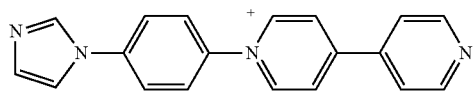

Chemical Formula 1B

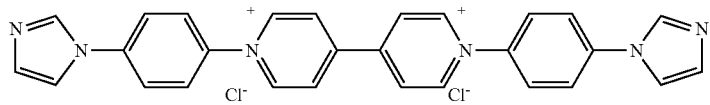

Chemical Formula 1C

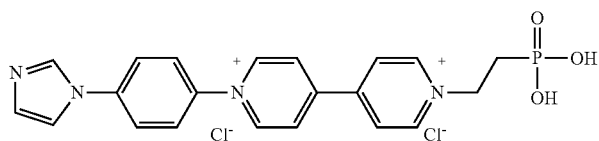

Chemical Formula 1D

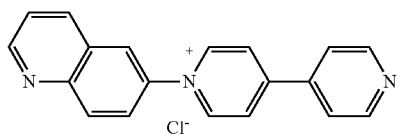

Chemical Formula 1E

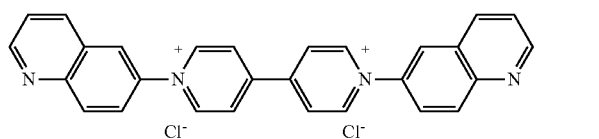

Chemical Formula 1F

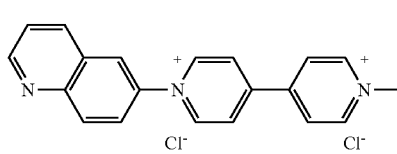

Chemical Formula 1G

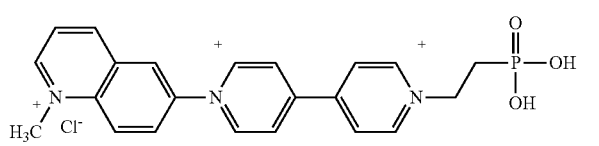

Chemical Formula 1H

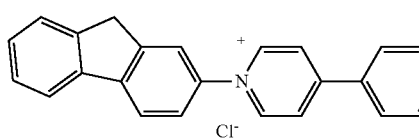

Chemical Formula 1I

Chemical Formula 1J

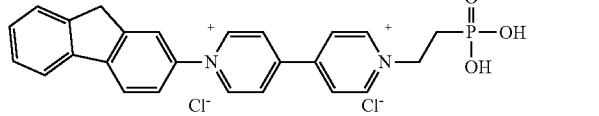

Chemical Formula 1K

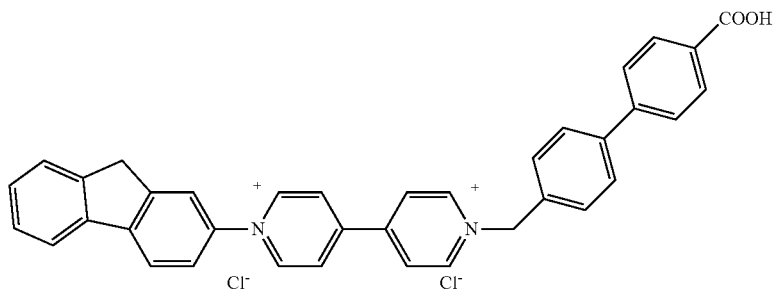

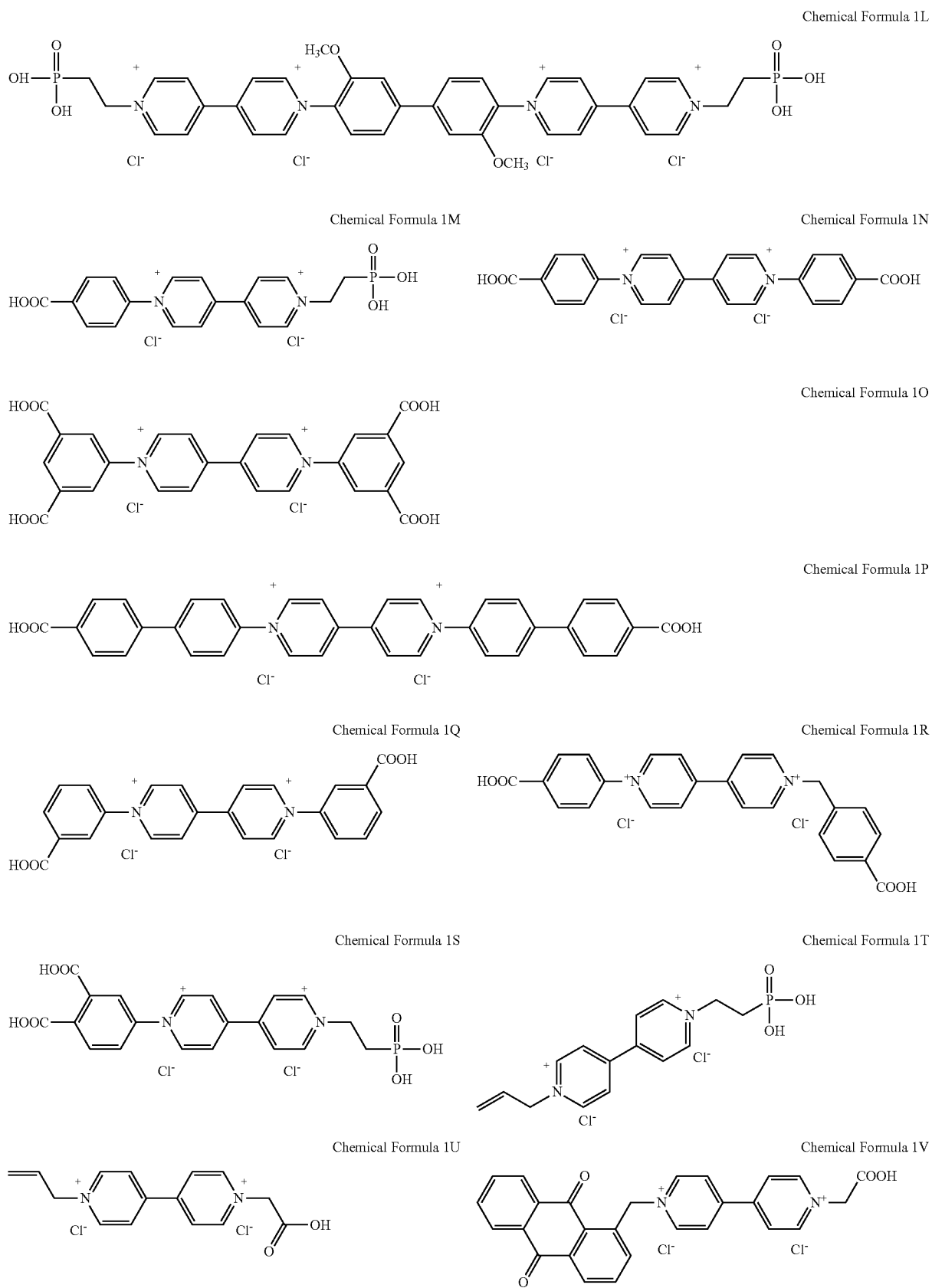

-continued
Chemical Formula 1W
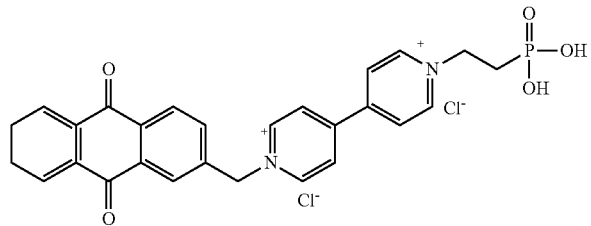
Chemical Formula 1X
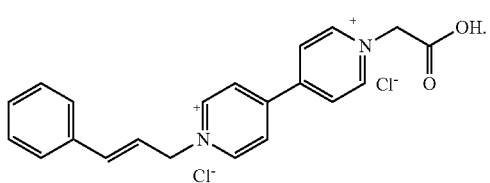
* * * * *